US011944690B2

(12) United States Patent
Holzschuh et al.

(10) Patent No.: US 11,944,690 B2
(45) Date of Patent: Apr. 2, 2024

(54) FORMULATION OF CONTRAST MEDIA AND PROCESS OF PREPARATION THEREOF

(71) Applicants: BAYER AKTIENGESELLSCHAFT, Leverkusen (DE); BAYER PHARMA AKTIENGESELLSCHAFT, Berlin (DE)

(72) Inventors: Stephan Holzschuh, Haan (DE); Thomas Frenzel, Berlin (DE); Gregor Jost, Berlin (DE); Jessica Lohrke, Berlin (DE); Wolfgang Ebert, Krefeld (DE); Thomas Brumby, Berlin (DE); Wolfgang Halfbrodt, Berlin (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 176 days.

(21) Appl. No.: 17/295,647

(22) PCT Filed: Nov. 21, 2019

(86) PCT No.: PCT/EP2019/082117
§ 371 (c)(1),
(2) Date: May 20, 2021

(87) PCT Pub. No.: WO2020/104602
PCT Pub. Date: May 28, 2020

(65) Prior Publication Data
US 2022/0008562 A1 Jan. 13, 2022

(30) Foreign Application Priority Data
Nov. 23, 2018 (EP) .................... 18208090

(51) Int. Cl.
A61K 49/10 (2006.01)
A61K 49/08 (2006.01)
A61K 49/12 (2006.01)

(52) U.S. Cl.
CPC .......... *A61K 49/108* (2013.01); *A61K 49/085* (2013.01); *A61K 49/124* (2013.01)

(58) Field of Classification Search
CPC ..... A61K 49/106; A61K 49/108; A61K 49/06
See application file for complete search history.

(56) References Cited

U.S. PATENT DOCUMENTS

| 4,485,237 A | 11/1984 | Willer |
| 4,647,447 A | 3/1987 | Gries et al. |
| 5,011,925 A | 4/1991 | Rajagopalan et al. |
| 5,039,512 A | 8/1991 | Kraft et al. |
| 5,141,740 A | 8/1992 | Rajagopalan et al. |
| 5,281,704 A | 1/1994 | Love et al. |
| 5,284,647 A | 2/1994 | Niedballa et al. |
| 5,403,572 A | 4/1995 | Gries et al. |
| 5,560,903 A | 10/1996 | Gries et al. |
| 5,650,133 A | 7/1997 | Carvalho et al. |
| 5,679,810 A | 10/1997 | Love et al. |
| 5,863,518 A | 1/1999 | Hashiguchi et al. |
| 5,866,562 A | 2/1999 | Schohe-Loop et al. |
| 5,876,695 A | 3/1999 | Gries et al. |
| 5,919,433 A | 7/1999 | Platzek et al. |
| 6,019,959 A | 2/2000 | Platzek et al. |
| 6,045,776 A | 4/2000 | Platzek et al. |
| 6,056,939 A | 5/2000 | Desreux et al. |
| 6,248,306 B1 | 6/2001 | Schmitt-Willich et al. |
| 6,440,956 B1 | 8/2002 | Port |
| 6,447,749 B1 | 9/2002 | Licha et al. |
| 6,511,649 B1 | 1/2003 | Harris et al. |
| 6,537,520 B1 | 3/2003 | Rajopadhye et al. |
| 6,693,190 B1 | 2/2004 | Ranganathan et al. |
| 7,294,615 B1 | 11/2007 | Bovin et al. |
| 8,545,813 B2 | 10/2013 | Song et al. |
| 11,021,451 B2 | 6/2021 | Lattuada et al. |
| 11,110,185 B2 | 9/2021 | Meijer et al. |
| 2002/0052354 A1 | 5/2002 | Platzek et al. |
| 2002/0077456 A1 | 6/2002 | Takano et al. |
| 2003/0004236 A1 | 1/2003 | Meade |
| 2003/0171561 A1 | 9/2003 | Pillai et al. |
| 2004/0170566 A1 | 9/2004 | Chang et al. |

(Continued)

FOREIGN PATENT DOCUMENTS

| CA | 2274132 A1 | 6/1998 |
| CN | 102442996 A | 5/2012 |

(Continued)

OTHER PUBLICATIONS

"International Preliminary Report on Patentability from PCT Application No. PCT/EP2019/082117", dated May 25, 2021.
Pikkemaat J.A., et al., "Dendritic PARACEST Contrast Agents for Magnetic Resonance Imaging," Contrast Media & Molecular Imaging, Sep.-Oct. 2007, vol. 2 (5), pp. 229-239.
Pittman C.U., et al., "Columns: Polymer Supports in Synthesis," Polymer News, 2005, vol. 30 (1), pp. 14-15.
Polyanichko K.V., et al., "Synthesis of Dendronized Polymeric Chelating Agents using Hydrazone Ligation Strategy," European Polymer Journal, Jul. 2017, vol. 92, pp. 117-125.
Preslar A.T., et al., "Correction to Gd(III)-Labeled Peptide Nanofibers for Reporting on Biomaterial Localization in Vivo," ACS Nano, Nov. 2015, vol. 9 (11), p. 11502.
Preslar A.T., et al., "Gd(III)-Labeled Peptide Nanofibers for Reporting on Biomaterial Localization in Vivo," ACS Nano, Jun. 2014, vol. 8 (7), pp. 7325-7332.

(Continued)

*Primary Examiner* — James W Rogers
(74) *Attorney, Agent, or Firm* — Joseph L. Kent; James R. Stevenson; David Schramm

(57) ABSTRACT

The present disclosure relates to a liquid pharmaceutical formulation comprising a DOSA-derived tetra-chelate of formula (I), in which M is an ion of a paramagnetic metal, preferably a $Gd^{3+}$ ion, and $R^1$, $R^2$, $R^3$, $R^4$ and $R^5$ are as defined in the claims, in a pharmaceutical acceptable solvent. The present disclosure also relates to a method of preparation of said liquid pharmaceutical formulation and to a method of imaging involving said liquid pharmaceutical formulation.

14 Claims, No Drawings

(56) References Cited

U.S. PATENT DOCUMENTS

| | | |
|---|---|---|
| 2006/0093554 A1 | 5/2006 | Platzek et al. |
| 2006/0104908 A1 | 5/2006 | Grimmond et al. |
| 2007/0202047 A1 | 8/2007 | Wolf et al. |
| 2009/0196829 A1 | 8/2009 | Song et al. |
| 2011/0081428 A1 | 4/2011 | Lithgow et al. |
| 2012/0244070 A1 | 9/2012 | Lu et al. |
| 2013/0302258 A1 | 11/2013 | Meade et al. |
| 2014/0363376 A1 | 12/2014 | Sun et al. |
| 2016/0101196 A1 | 4/2016 | Medina et al. |
| 2017/0293009 A1 | 10/2017 | Meade et al. |
| 2020/0017453 A1 | 1/2020 | Boi et al. |

FOREIGN PATENT DOCUMENTS

| | | | |
|---|---|---|---|
| CN | 102614531 A | 8/2012 | |
| CN | 102973955 A | 3/2013 | |
| CN | 103554185 A | 2/2014 | |
| CN | 103611171 A | 3/2014 | |
| DE | 19525924 A1 | 1/1997 | |
| DE | 19652386 A1 | 6/1998 | |
| DE | 19652387 A1 | 6/1998 | |
| DE | 102007058220 A1 | 6/2009 | |
| DE | 102009053171 A1 * | 5/2011 | ........... C07D 257/02 |
| EP | 0255471 A1 | 2/1988 | |
| EP | 0305320 A2 | 3/1989 | |
| EP | 0438206 A1 | 7/1991 | |
| EP | 0454078 A2 | 10/1991 | |
| EP | 0946525 A1 | 10/1999 | |
| EP | 0946526 A1 | 10/1999 | |
| EP | 1931673 A1 | 6/2008 | |
| EP | 2457594 A1 | 5/2012 | |
| EP | 2457914 A1 | 5/2012 | |
| EP | 3101012 A1 | 12/2016 | |
| EP | 3551614 B1 | 8/2021 | |
| JP | 2008012596 A | 1/2008 | |
| KR | 20130080245 A | 7/2013 | |
| KR | 20140021742 A | 2/2014 | |
| KR | 20140021743 A | 2/2014 | |
| WO | 9002652 A1 | 3/1990 | |
| WO | 9103200 A1 | 3/1991 | |
| WO | 9105762 A1 | 5/1991 | |
| WO | 9209527 A1 | 6/1992 | |
| WO | 9209884 A1 | 6/1992 | |
| WO | 9218536 A2 | 10/1992 | |
| WO | 9221017 A1 | 11/1992 | |
| WO | 9311120 A1 | 6/1993 | |
| WO | 9311800 A1 | 6/1993 | |
| WO | 9316375 A1 | 8/1993 | |
| WO | 9407894 A1 | 4/1994 | |
| WO | 9427644 A1 | 12/1994 | |
| WO | 9501966 A1 | 1/1995 | |
| WO | 9509848 A2 | 4/1995 | |
| WO | 9520353 A1 | 8/1995 | |
| WO | 9531444 A1 | 11/1995 | |
| WO | 9601655 A1 | 1/1996 | |
| WO | 9616677 A2 | 6/1996 | |
| WO | 9638184 A2 | 12/1996 | |
| WO | 9702051 A2 | 1/1997 | |
| WO | 9718231 A1 | 5/1997 | |
| WO | 9723245 A1 | 7/1997 | |
| WO | 9726017 A2 | 7/1997 | |
| WO | 9730969 A1 | 8/1997 | |
| WO | 9732862 A1 | 9/1997 | |
| WO | 9824775 A1 | 6/1998 | |
| WO | 9901161 A1 | 1/1999 | |
| WO | 9916757 A1 | 4/1999 | |
| WO | 9921592 A1 | 5/1999 | |
| WO | 0001698 A1 | 1/2000 | |
| WO | 0009169 A1 | 2/2000 | |
| WO | 0076616 A1 | 12/2000 | |
| WO | 0076760 A1 | 12/2000 | |
| WO | 0151095 A2 | 7/2001 | |
| WO | 0152906 A2 | 7/2001 | |
| WO | 0164708 A1 | 9/2001 | |
| WO | 0197848 A2 | 12/2001 | |
| WO | 0197860 A2 | 12/2001 | |
| WO | 0213874 A2 | 2/2002 | |
| WO | 0213875 A2 | 2/2002 | |
| WO | 0214309 A1 | 2/2002 | |
| WO | 02051854 A1 | 7/2002 | |
| WO | 03009874 A1 | 2/2003 | |
| WO | 03011115 A2 | 2/2003 | |
| WO | 03013617 A2 | 2/2003 | |
| WO | 03014157 A2 | 2/2003 | |
| WO | 03074523 A2 | 9/2003 | |
| WO | 03088823 A2 | 10/2003 | |
| WO | 2004006965 A2 | 1/2004 | |
| WO | 2004006979 A2 | 1/2004 | |
| WO | 2004065407 A2 | 8/2004 | |
| WO | 2004074267 A1 | 9/2004 | |
| WO | 2005001415 A2 | 1/2005 | |
| WO | 2005007200 A1 | 1/2005 | |
| WO | 2005108379 A1 | 11/2005 | |
| WO | 2005115997 A1 | 12/2005 | |
| WO | 2006002873 A2 | 1/2006 | |
| WO | 2006002874 A1 | 1/2006 | |
| WO | 2006014530 A2 | 2/2006 | |
| WO | 2006029560 A1 | 3/2006 | |
| WO | 2006080022 A2 | 8/2006 | |
| WO | 2006136460 A2 | 12/2006 | |
| WO | 2007042506 A1 | 4/2007 | |
| WO | 2007064226 A2 | 6/2007 | |
| WO | 2007064227 A1 | 6/2007 | |
| WO | 2007069909 A2 | 6/2007 | |
| WO | 2007084264 A2 | 7/2007 | |
| WO | 2007088129 A2 | 8/2007 | |
| WO | 2007100563 A2 | 9/2007 | |
| WO | 2007111514 A1 | 10/2007 | |
| WO | 2007111515 A1 | 10/2007 | |
| WO | 2007112100 A2 | 10/2007 | |
| WO | 2007128567 A1 | 11/2007 | |
| WO | 2007128873 A1 | 11/2007 | |
| WO | 2008017122 A1 | 2/2008 | |
| WO | 2008022263 A1 | 2/2008 | |
| WO | 2008087017 A2 | 7/2008 | |
| WO | 2008125594 A1 | 10/2008 | |
| WO | 2009013350 A2 | 1/2009 | |
| WO | 2009018332 A1 | 2/2009 | |
| WO | 2009027388 A2 | 3/2009 | |
| WO | 2009030735 A1 | 3/2009 | |
| WO | 2009047245 A1 | 4/2009 | |
| WO | 2009077575 A1 | 6/2009 | |
| WO | 2009080739 A1 | 7/2009 | |
| WO | 2009093082 A1 | 7/2009 | |
| WO | 2009098191 A2 | 8/2009 | |
| WO | 2009098192 A1 | 8/2009 | |
| WO | 2009103744 A2 | 8/2009 | |
| WO | 2009127715 A1 | 10/2009 | |
| WO | 2009143101 A2 | 11/2009 | |
| WO | 2010006755 A2 | 1/2010 | |
| WO | 2010039609 A2 | 4/2010 | |
| WO | 2010056590 A2 | 5/2010 | |
| WO | 2010066815 A2 | 6/2010 | |
| WO | 2010108125 A2 | 9/2010 | |
| WO | 2010147666 A1 | 12/2010 | |
| WO | 2011031740 A1 | 3/2011 | |
| WO | 2011073371 A1 | 6/2011 | |
| WO | 2011088193 A2 | 7/2011 | |
| WO | 2011124672 A1 | 10/2011 | |
| WO | 2011158189 A1 | 12/2011 | |
| WO | 2012059576 A1 | 5/2012 | |
| WO | 2012142702 A1 | 10/2012 | |
| WO | 2012143355 A1 | 10/2012 | |
| WO | 2013022797 A1 | 2/2013 | |
| WO | 2013087965 A1 | 6/2013 | |
| WO | 2014052471 A1 | 4/2014 | |
| WO | 2014075079 A1 | 5/2014 | |
| WO | 2014110372 A1 | 7/2014 | |
| WO | 2014124943 A1 | 8/2014 | |
| WO | 2014197763 A1 | 12/2014 | |
| WO | 2015071856 A1 | 5/2015 | |
| WO | 2015071857 A1 | 5/2015 | |
| WO | 2015171792 A1 | 11/2015 | |
| WO | 2016050210 A1 | 4/2016 | |

(56) References Cited

FOREIGN PATENT DOCUMENTS

| WO | 2016149363 A1 | 9/2016 |
|----|---------------|--------|
| WO | 2016193190 A1 | 12/2016 |
| WO | 2017004220 A1 | 1/2017 |
| WO | 2017030728 A1 | 2/2017 |
| WO | 2017098038 A1 | 6/2017 |
| WO | 2017098044 A1 | 6/2017 |
| WO | 2017178301 A1 | 10/2017 |
| WO | 2018096082 A1 | 5/2018 |
| WO | 2018108780 A1 | 6/2018 |

OTHER PUBLICATIONS

Ranganathan R.S., et al., "New Multimeric Magnetic Resonance Imaging Agents," Investigative Radiology, Nov. 1998, vol. 33 (11), pp. 779-797.

Raymond Kenneth N.; et al, "Next Generation, Hight Relaxivity Gadolinium MRI Agents", Bioconjugate Chem., 2005, vol. 16, Issue 1, 3-8.

Regueiro-Figueroa M., et al., "Structure and Dynamics of Lanthanide(III) Complexes with an N-Alkylated do3a Ligand (H3do3a = 1,4,7,10-Tetraazacyclododecane-1,4,7-triacetic Acid): A Combined Experimental and DFT Study," European Journal of Inorganic Chemistry, Aug. 2010, vol. 2010 (23), pp. 3586-3595.

Reichert D.E., et al., "Molecular Mechanics Investigation of Gadolinium(III) Complexes," Inorganic Chemistry, Nov. 1996, vol. 35 (24), pp. 7013-7020.

Revesz L., et al., "Synthesis of Novel Piperazine Based Building Blocks: 3,7,9-triazabicyclo[3.3.1]nonane, 3,6,8-riazabicyclo[3.2.2]nonane, 3-oxa-7,9-diazabicyclo[3.3.1]nonane and 3-oxa-6,8-diazabicyclo[3.2.2]nonane," Tetrahedron Letters, Aug. 2005, vol. 46 (33), pp. 5577-5580.

Riechers A., et al., "Binding of Phosphorylated Peptides and Inhibition of their Interaction with Disease-relevant Human Proteins by Synthetic Metal-chelate Receptors," Journal of Molecular Recognition, May-Jun. 2010, vol. 23 (3), pp. 329-334.

Rodriguez-Rodriguez A., et al., "Stable Mn2+, Cu2+ and Ln3+ Complexes with Cyclen-based Ligands Functionalized with Picolinate Pendant Arms," Dalton Transactions, 2015, vol. 44, pp. 5017-5031.

Rohrer M., et al., "Comparison of Magnetic Properties of MRI Contrast Media Solutions at Different Magnetic Field Strengths," Investigative Radiology, Nov. 2005, vol. 40 (11), pp. 715-724.

Roy O.; et al, "The tert-Butyl Side Chain: A Powerful Means to Lock Peptoid Amide Bonds in the Cis Conformation", Organic Letters, 2013, vol. 15, No. 9, 2246-2249.

Scarso A., et al., "Tripodal, Cooperative, and Allosteric Transphosphorylation Metallocatalysts," The Journal of Organic Chemistry, Jan. 2007, vol. 72 (2), pp. 376-385.

Schmidek H.H., et al., "Morphological Studies of Rat Brain Tumors Induced by N-nitrosomethylurea," Mar. 1971, vol. 34 (3), pp. 335-340.

Schuhle D.T., et al., "Calix[4]arenes as Molecular Platforms for Magnetic Resonance Imaging (MRI) Contrast Agents," Chemistry a European Journal, 2009, vol. 15 (13), pp. 3290-3296.

Schuhle D.T., et al., "Densely Packed Gd(III)-chelates with Fast Water Exchange on a Calix[4]arene Scaffold: a Potential MRI Contrast Agent," Dalton Transactions, Jan. 2010, vol. 39, pp. 185-191.

Schuhle D.T., et al., "Liposomes with Conjugates of a Calix[4]arene and a Gd-DOTA Derivative on the Outside Surface; an Efficient Potential Contrast Agent for MRI," Chemical Communications, 2010, vol. 46, pp. 4399-4401.

Schurink H.B., "Pentaerythrityl Bromide and Iodide," Organic Syntheses, 1937, vol. 17, p. 73.

Sherry A. Dean; et al, "Chemical Exchange Saturation Transfer Contrast Agents For Magnetic Resonance Imaging", Annu Rev. Biomed Eng., 2008, 10, 391-411.

Siegfried L., et al., "Homo- and Heteropolynuclear Ni2+ and Cu2+ Complexes of Polytopic Ligands, Consisting of a Tren Unit Substituted with Three 12-membered Tetraazamacrocycles," Dalton Transactions, Nov. 2007, pp. 4797-4810.

Song Y., et al., "Synthesis of Multimeric MR Contrast Agents for Cellular Imaging," Journal of the American Chemical Society, May 2008, vol. 130 (21), pp. 6662-6663.

Sorensen T.J., et al., "Preparation and Study of an f,f,f',f" Covalently Linked Tetranuclear Hetero-trimetallic Complex—a Europium, Terbium, Dysprosium Triad," Chemical Communications, 2013, vol. 49 (8), pp. 783-785.

Sorensen T.J., et al., "Triheterometallic Lanthanide Complexes Prepared from Kinetically Inert Lanthanide Building Blocks," European Journal of Inorganic Chemistry, Apr. 2017, vol. 2017 (15), pp. 2165-2172.

Suchy; et al, "A paramagnetic chemical exchange-based MRI probe metabolized by cathepsin D: design, synthesis and cellular uptake studies", Organic & Biomolecular Chemistry, Mar. 26, 2010, vol. 8, 2560-2566.

Suh John T.; et al, "Angiotensin-Convertin Enzyme Inhibitors. New Orally Active Antihypertensive (Mercaptoalkanoyl)- and [(Acylthio)alkanoyl]glycine Derivatives", Journal of Medicinal Chemistry, 1985, vol. 28, No. 1, 57-66.

Sung S., et al., "Multimetallic Complexes and Functionalized Gold Nanoparticles Based on a Combination of d- and f-Elements," Inorganic Chemistry, Feb. 2014, vol. 53 (4), pp. 1989-2005.

Sy M., et al., "Spectroscopic Properties of a Family of Mono- to Trinuclear Lanthanide Complexes," European Journal of Inorganic Chemistry, Apr. 2017, vol. 2017 (14), pp. 2122-2129.

Takemura H., et al., "Synthesis and Inclusion Properties of Pyridinophane-linked Macrocycles," Journal of the Chemical Society, Perkin Transactions 1, Jan. 1996, pp. 277-280.

Tamain C., et al., "Coordination of Tetravalent Actinides (An=ThIV, UIV, NpIV, PuIV) with DOTA: from Dimers to Hexamers," Chemistry a European Journal, May 2017, vol. 23 (28), pp. 6864-6875.

Tamain C., et al., "First Evidence of a Water-Soluble Plutonium(IV) Hexanuclear Cluster," European Journal of Inorganic Chemistry, Aug. 2016, vol. 2016 (22), pp. 3536-3540.

Tanaka T., et al., "11B NMR Probes of Copper(II): Finding and Implications of the Cu2+-Promoted Decomposition of ortho-Carborane Derivatives," European Journal of Inorganic Chemistry, Apr. 2016, vol. 2016 (12), pp. 1819-1834.

Tei L., et al., "Target Visualization by MRI Using the Avidin/Biotin Amplification Route: Synthesis and Testing of a Biotin-Gd-DOTA Monoamide Trimer," Chemistry a European Journal, Jul. 2010, vol. 16 (27), pp. 8080-8087.

Terreno E., et al., "Highly Shifted LIPOCEST Agents Based on the Encapsulation of Neutral Polynuclear Paramagnetic Shift Reagents," Chemical Communications, 2008, pp. 600-602.

Thompson M.K., et al., "Cooperative Processes Governing Formation of Small Pentanuclear Lanthanide(III) Nanoclusters and Energy Transport within and between Them," Inorganic Chemistry, Aug. 2001, vol. 40 (17), pp. 4332-4341.

Thompson M.K., et al., "Formation of Two Diverse Classes of Poly(amino-alkoxide) Chelates and their Mononuclear and Polynuclear Lanthanide(III) Complexes," Inorganic Chemistry, Jul. 2003, vol. 42 (16), pp. 4828-4841.

Tombach B., et al., "Value of 1.0-M Gadolinium Chelates: Review of Preclinical and Clinical Data on Gadobutrol," European Radiology, Jun. 2002, vol. 12 (6), pp. 1550-1556.

Toth E.; et al., "Chapter 2: Relaxivity of Gadolinium(III) Complexes: Theory and Mechanism", The Chemistry of Contrast Agents in Medical Magnetic Resonance Imaging, John Wiley & Sons, Ltd., 2013, Second Edition, 25-81.

Tremblay M.S., et al., "Synthesis of Luminescent Heterometallic Bis-Ianthanide Complexes via Selective, Sequential Metallation," Chemical Communications, Sep. 2006, pp. 4116-4118.

Tropiano M., et al., "Using Remote Substituents to Control Solution Structure and Anion Binding in Lanthanide Complexes," Chemistry a European Journal, Dec. 2013, vol. 19 (49), p. 16566-16571.

Van Alphen J., et al., "On Aliphatic Polyamines VII," 1938, vol. 57 (3), pp. 265-276.

Verwilst P., et al., "A Tripodal Ruthenium-Gadolinium Metallostar as a Potential alphavBeta3 Integrin Specific Bimodal Imaging Contrast Agent," Inorganic Chemistry, May 2012, vol. 51 (11), pp. 6405-6411.

(56) References Cited

OTHER PUBLICATIONS

Verwilst P., et al., "Recent Advances in Gd-chelate Based Bimodal Optical/MRI Contrast Agents," Chemical Society Reviews, Jan. 2015, vol. 44 (7), pp. 1791-1806.
Vetterlein K., et al., "Capillary Electrophoresis for the Characterization of the Complex Dendrimeric Contrast Agent Gadomer," Electrophoresis, Jun. 2006, vol. 27 (12), pp. 2400-2412.
Vetterlein K., et al., "Comprehensive Profiling of the Complex Dendrimeric Contrast Agent Gadomer Using a Combined Approach of CE, MS, and CE-MS," Electrophoresis, Aug. 2007, vol. 28 (17), pp. 3088-3099.
Wang J., et al., "Anion Separation and Preconcentration with Cyclen and Cyclen-Resorcinarene Derivatives," Journal of Chromatographic Science, Aug. 2009, vol. 47 (7), pp. 510-515.
Wang J., et al., "Multiple Anion Binding by a Zinc-containing Tetratopic Cyclen-resorcinarene," Journal of Inclusion Phenomena and Macrocyclic Chemistry, Jun. 2010, vol. 67 (1), pp. 55-61.
Wang J., et al., "Synthesis, Characterization, and Activity of Cyclotriphosphazene-Cyclene Conjugates," Phosphorus, Sulfur, and Silicon and the Related Elements, 2013, vol. 188 (1-3), pp. 54-58.
Wang L., et al., "A Multiple Gadolinium Complex Decorated Fullerene as a Highly Sensitive T(1) Contrast Agent," Chemical Communications, Mar. 2015, vol. 51 (21), pp. 4390-4393.
Hjelm L., "Optimization of Gadolinium-based MRI Contrast Agents for High Magnetic-field Applications," Future Medicinal Chemistry, Mar. 2010, vol. 2 (3), pp. 385-396.
Hermann P., et al., "Gadolinium(III) Complexes as MRI Contrast Agents: Ligand Design and Properties of the Complexes," Dalton Transactions, Jun. 2008, pp. 3027-3047.
Hill L.R., et al., "Ternary Self-assemblies in Water: Forming a Pentanuclear ReLn4 Assembly by Association of Binuclear Lanthanide Binding Pockets With Fac-Re(CO)3(Dinicotinate)2cl," Dalton Transactions, Aug. 2013, vol. 42, pp. 16255-16258.
Huang Z., et al., "A Fluorinated Dendrimer-Based Nanotechnology Platform: New Contrast Agents for High Field Imaging," Investigative Radiology, Oct. 2010, vol. 45 (10), pp. 641-654.
International Search Report and Written Opinion for Application No. PCT/EP2016/062105, dated Jul. 13, 2016, 10 pages.
"International Search Report and Written Opinion from PCT Application No. PCT/EP2017/080306", dated Mar. 6, 2018.
Iwaki S., et al., "A Design Strategy for Small Molecule-based Targeted MRI Contrast Agents: Their Application for Detection of Atherosclerotic Plaques," Organic & Biomolecular Chemistry, Nov. 2014, vol. 12 (43), pp. 8611-8618.
Jacques V., et al., "High-relaxivity Magnetic Resonance Imaging Contrast Agents. Part 2. Optimization of Inner- and Second-sphere Relaxivity," Investigative Radiology, Oct. 2010, vol. 45 (10), pp. 613-624.
Jacques V., et al., Synthesis of MRI Contrast Agents II. Macrocyclic Ligands, Table of Contents.
Jagadish B.; et al, "On the synthesis of 1,4,7-tris(tert-butoxycarbonylmethyl)-1,4,7,10-tetraazacyclododecane", Tetrahedron Letters, 2011, 52, 2058-2061.
Jebasingh B., et al., "Synthesis and Relaxivity Studies of a Tetranuclear Gadolinium(III) Complex of DO3A as a Contrast-Enhancing Agent for MRI," Inorganic Chemistry, Nov. 2005, vol. 44 (25), pp. 9434-9443.
Kimura E., et al., "A Tris(ZnII-1,4,7,10-tetraazacyclododecane) Complex as a New Receptor for Phosphate Dianions n Aqueous Solution," Journal of the American Chemical Society, Apr. 1997, vol. 119 (13), pp. 3068-3076.
Kimura E., et al., "Selective and Efficient Recognition of Thymidylylthymidine (TpT) by Bis(ZnII-cyclen) and Thymidylylthymidylylthymidine (TpTpT) by Tris(ZnII-cyclen) at Neutral pH in Aqueous Solution," Chemistry a European Journal, Nov. 1999, vol. 5 (11), pp. 3113-3123.
Kobelev S.M., et al., "Macrobicycles Based on Cyclen and Cyclam Containing 1,3-disubstituted Adamantane Moieties," Archive for Organic Chemistry, Sep. 2012, vol. 2012 (7), pp. 196-209.
Kobelev S.M., et al., "Synthesis of Macrobi- and Macrotricyclic Compounds Comprising Pyrimidyl Substituted Cyclen and Cyclam," Heterocycles, 2011, vol. 82 (2), pp. 1447-1476.
Konig B., et al., "Synthesis of Functionalized Aza-macrocycles and the Application of their Metal Complexes in Binding Processes," Journal of Inclusion Phenomena and Macrocyclic Chemistry, May 2000, vol. 37 (1-4), pp. 39-57.
Kriemen E., et al., "Synthesis and Structural Analysis of 1,4,7,10-Tetraazacyclododecane-1,4,7,10-tetraazidoethylacetic Acid (DOTAZA) Complexes," European Journal of Inorganic Chemistry, Nov. 2015, vol. 2015 (32), pp. 5368-5378.
Kriemen E., et al., "Synthesis of 1,4,7,10-Tetra-azacyclododecan-1,4,7,10-tetra-azidoethylacetic Acid (DOTAZA) and Related "Clickable" DOTA Derivatives," Chemistry an Asian Journal, Aug. 2014, vol. 9 (8), pp. 2197-2204.
Krishan Kumar., et al., "Synthesis, Stability, and Crystal Structure Studies of Some Ca2+, Cu2+, and Zn2+ Complexes of Macrocyclic Polyamino Carboxylates," Inorganic Chemistry, Dec. 1995, vol. 34 (26), pp. 6472-6480.
Kumar A., et al., "Molecular Platform for Design and Synthesis of Targeted Dual-Modality Imaging Probes," Bioconjugate Chemistry, Jan. 2015, vol. 26 (3), pp. 549-558.
Laurent S., et al., "Stability of MRI Paramagnetic Contrast Media: a Proton Relaxometric Protocol for Transmetallation Assessment," Investigative Radiology, Feb. 2001, vol. 36 (2), pp. 115-122.
Leich V., et al., "Formation of a Cationic Calcium Hydride Cluster with a "Naked" Triphenylsilyl Anion by Hydrogenolysis of Bis(triphenylsilyl)calcium," Inorganic Chemistry, May 2015, vol. 54 (10), pp. 4927-4933.
Li C., et al., "Multimodal Image-Guided Enzyme/Prodrug Cancer Therapy," Journal of the American Chemical Society, Nov. 2006, vol. 128 (47), pp. 15072-15073.
Li N., et al., "Cation Separation and Preconcentration Using Columns Containing Cyclen and Cyclen-resorcinarene Derivatives," Journal of Chromatography, Jul. 2012, vol. 1245 (2012), pp. 83-89.
Li W.S., et al., "A Gd3Al Tetranuclear Complex as a Potential Bimodal MRI/optical Imaging Agent," Dalton Transactions, Aug. 2012, vol. 41 (31), pp. 9405-9410.
Liu J., et al., "Molecular Engineering of Aqueous Soluble Triarylboron-Compound-Based Two-Photon Fluorescent Probe for Mitochondria H2S with Analyte-Induced Finite Aggregation and Excellent Membrane Permeability," Analytical Chemistry, 2016, vol. 88 (1), pp. 1052-1057.
Lopez-Martinez L.M., et al., "Synthesis, Characterization, and Cu2+ Coordination Studies of a 3-Hydroxy-4-pyridinone Aza Scorpiand Derivative," Inorganic Chemistry, Jul. 2016, vol. 55 (15), pp. 7564-7575.
Maindron N., et al., "Near-Infrared-Emitting BODIPY-trisDOTA(111) in as a Monomolecular Multifunctional Imaging Probe: from Synthesis to In Vivo Investigations," Chemistry a European Journal, Aug. 2016, vol. 22 (36), pp. 12670-12674.
Mamedov I., et al., "Structure-related Variable Responses of Calcium Sensitive MRI Probes," Organic & Biomolecular Chemistry, Aug. 2011, vol. 9 (16), pp. 5816-5824.
Martin D., et al., "Discrete Magnesium Hydride Aggregates: A Cationic Mg13H18 Cluster Stabilized by NNNN-Type Macrocycles," Angewandte Chemie, Mar. 2015, vol. 54 (13), pp. 4115-4118.
Martin D., et al., "Hydrido and Allyl/Hydrido Complexes of Early Lanthanides Supported by an NNNN-Type Macrocyclic Ligand," European Journal of Inorganic Chemistry, Aug. 2013, vol. 2013 (22-23), pp. 3987-3992.
Martinez G.V., et al., "Demonstration of a Sucrose-derived Contrast Agent for Magnetic Resonance Imaging of the GI Tract," Bioorganic & Medicinal Chemistry Letters, Apr. 2013, vol. 23 (7), pp. 2061-2064.
Mastarone D.J., et al., "A Modular System for the Synthesis of Multiplexed Magnetic Resonance Probes," Journal of the American Chemical Society, Mar. 2011, vol. 133 (14), pp. 5329-5337.
Merbach; Andre et al, "The Chemistry of Contrast Agents in Medical Magnetic Resonance Imaging, 2nd Edition", John Wiley & Sons Ltd., 2013, 31-32, 194.

(56) References Cited

OTHER PUBLICATIONS

Merbach A.E., et al., "Chapter II: Relaxivity of Gadolinium(III) Complexes: Theory and Mechanism" in: The Chemistry of Contrast Agents in Medical Magnetic Resonance Imaging, 2nd Edition, 2013, Table of Contents.

Mier W., et al., "Synthesis of Peptide Conjugated Chelator Oligomers for Endoradiotherapy and MRT Imaging," Tetrahedron Letters, Jul. 2004, vol. 45 (28), pp. 5453-5455.

Mieville P., et al., "Synthesis, Complexation and NMR Relaxation Properties of Gd3+ Complexes of Mes(DO3A)3," Dalton Transactions, Mar. 2011, vol. 40, pp. 4260-4267.

Mishra A., et al., "Facile Synthesis and Relaxation Properties of Novel Bispolyazamacrocyclic Gd3+ Complexes: an Attempt Towards Calcium-sensitive MRI Contrast Agents," Inorganic Chemistry, Feb. 2008, vol. 47 (8), p. 3460.

Montalbetti C.A., et al., "Amide Bond Formation and Peptide Coupling," Tetrahedron, 2005, vol. 61, pp. 10827-10852.

Morcos; S.K., "Extracellular gadolinium contrast agents: Differences in stability", European Journal of Radiology, May 2008, vol. 66/Issue 2, 175-179.

Muller A., et al., "Preparation of Luminescent Chemosensors by Post-functionalization of Vesicle Surfaces," Organic & Biomolecular Chemistry, 2015, vol. 13 (6), pp. 1690-1699.

Napolitano R., et al., "Synthesis and Relaxometric Characterization of a MRI Gd-Based Probe Responsive to Glutamic Acid Decarboxylase Enzymatic Activity," Journal of Medical Chemistry, Mar. 2013, vol. 56 (6), pp. 2466-2477.

Niedbalski P., et al., "13C Dynamic Nuclear Polarization Using a Trimeric Gd3+ Complex as an Additive," The Journal of Physical Chemistry, Jul. 2017, vol. 121 (27), pp. 5127-5135.

Nithyakumar A., et al., "Tri- and Tetranuclear RuII-GdIII2 and RuII-GdIII3 d-f Heterometallic Complexes as Potential Bimodal Imaging Probes for MRI and Optical Imaging," New Journal of Chemistry, Mar. 2016, vol. 40, pp. 4606-4616.

Notni J., et al., "Convenient Synthesis of 68Ga-Labeled Gadolinium(III) Complexes: Towards Bimodal Responsive Probes for Functional Imaging with PET/MRI," Chemistry a European Journal, Sep. 2013, vol. 19 (38), pp. 12602-12606.

Olga Capasso "Letter accompanying Notice of Opposition Against EP 3303307B1" and "Notice of Opposition Against EP 3303307B1", submitted to European Patent Office, Jun. 4, 2020.

Oltmanns D., et al., "Zn(II)-bis(cyclen) Complexes and the Imaging of Apoptosis/Necrosis," Bioconjugate Chemistry, Oct. 2011, vol. 22 (12), pp. 2611-2624.

Overoye-Chan K., et al., "EP-2104R: A Fibrin-Specific Gadolinium-Based MRI Contrast Agent for Detection of Thrombus," Journal of the American Chemical Society, May 2008, vol. 130 (18), pp. 6025-6039.

Pang X., et al., "Bimetallic Schiff-base Aluminum Complexes Based on Pentaerythrityl Tetramine and their Stereoselective Polymerization of Racemic Lactide," RSC Advances, May 2014, vol. 4, pp. 22561-22566.

Paris J., et al., "Auto-assembling of Ditopic Macrocyclic Lanthanide Chelates with Transition-metal Ions. Rigid Multimetallic High Relaxivity Contrast Agents for Magnetic Resonance Imaging," Inorganic Chemistry, Jun. 2006, vol. 45 (13), pp. 5092-5102.

Aime S., et al., "Biodistribution of Gadolinium-Based Contrast Agents, Including Gadolinium Deposition," Journal of Magnetic Resonance Imaging, Dec. 2009, vol. 30 (6), pp. 1259-1267.

Averin A.D., et al., "Synthesis of a New Family of bi- and Polycyclic Compounds via Pd-catalyzed Amination of 1,7-di(3-bromobenzyl)cyclen," Tetrahedron Letters, Jun. 2008, vol. 49 (24), pp. 3950-3954.

Banerjee S.R., et al., "Synthesis and Evaluation of Gd(III)-Based Magnetic Resonance Contrast Agents for Molecular Imaging of Prostate-Specific Membrane Antigen," Angewandte Chemie, Sep. 2015, vol. 54 (37), pp. 10778-10782.

Bazzicalupi C., et al., "Tren-based Tris-macrocycles as Anion Hosts. Encapsulation of Benzenetricarboxylate Anions within Bowl-shaped Polyammonium Receptors," The Journal of Organic Chemistry, May 2005, vol. 70 (11), pp. 4257-4266.

Bazzicalupi C., et al., "Synthesis of New Tren-based Tris-macrocycles. Anion Cluster Assembling Inside the Cavity Generated by a Bowl-shaped Receptor," The Journal of Organic Chemistry, Dec. 2002, vol. 67 (25), pp. 9107-9110.

Bazzicalupi C., et al., "Zn(II) Coordination to Tren-based Tris-macrocycles. Activity of their Trinuclear Zn(II) Complexes in Carboxy- and Phosphate-ester Hydrolysis," Dalton Transactions, Aug. 2003, pp. 3574-3580.

Becker S., et al., "Application of Gadolinium-Based Contrast Agents and Prevalence of Nephrogenic Systemic Fibrosis in a Cohort of End-Stage Renal Disease Patients on Hemodialysis," Nephron Clinical Practice, Nov. 2012, vol. 121 (1-2), pp. C91-C94.

Bencini A., et al., "A Tris-Macrocycle with Proton Sponge Characteristics as Efficient Receptor for Inorganic Phosphate and Nucleotide Anions," European Journal of Organic Chemistry, Nov. 2009, vol. 2009 (32), pp. 5610-5621.

Bencini A., et al., "Proton and Cu(II) Binding to Tren-based Tris-macrocycles. Affinity Towards Nucleic Acids and Nuclease Activity," Dalton Transactions, Feb. 2003, pp. 793-800.

Berge S.M., et al., "Pharmaceutical Salts," Journal of Pharmaceutical Sciences, Jan. 1977, vol. 66 (1), pp. 1-19.

Besenius P., et al., "Controlling the Growth and Shape of Chiral Supramolecular Polymers in Water," Proceedings of the National Academy of Sciences of the United States of America, Oct. 2010, vol. 107 (42), pp. 17888-17893.

Besenius P., et al., "Peptide Functionalised Discotic Amphiphiles and their Self-assembly into Supramolecular Nanofibres," Soft Matter, 2011, vol. 7, pp. 7980-7983.

Bhuniya S., et al., "Uridine-based Paramagnetic Supramolecular Nanoaggregate with High Relaxivity Capable of Detecting Primitive Liver Tumor Lesions," Biomaterials, Sep. 2011, vol. 32 (27), pp. 6533-6540.

Bhuyan M., et al., "BiomaterialsRigid Luminescent Bis-Zinc(II)-Bis-Cyclen Complexes for the Detection of Phosphate Anions and Non-Covalent Protein Labeling in Aqueous Solution," European Journal of Organic Chemistry, May 2011, vol. 2011(15), pp. 2807-2817.

Boldrini V., et al., "Expeditious N-monoalkylation of 1,4,7,10-tetraazacyclododecane (Cyclen) via Formamido Protection," Tetrahedron Letters, Aug. 2000, vol. 41 (33), pp. 6527-6530.

Boros E., et al., "Gd(DOTAla): A Single Amino Acid Gd-complex as a Modular Tool for High Relaxivity MR Contrast Agent Development," Journal of the American Chemical Society, Dec. 2012, vol. 134 (48), pp. 19858-19868.

Bruckner K., et al., "Solid Phase Synthesis of Short Peptide-Based Multimetal Tags for Biomolecule Labeling," Bioconjugate Chemistry, May 2014, vol. 25 (6), pp. 1069-1077.

Bumb et al;, "Macromolecular and Dendrimer Based Magnetic Resonance Contrast Agents", Acta Radiol., Sep. 2010, vol. 51/Issue 7, 751-767.

Caravan P., "Strategies for Increasing the Sensitivity of Gadolinium Based Mri Contrast Agents," Chemical Society Reviews, Jun. 2006, vol. 35 (6), pp. 512-523.

Carney C.E., et al., "Cell Labeling via Membrane-Anchored Lipophilic MR Contrast Agents," Bioconjugate Chemistry, May 2014, vol. 25 (5), pp. 945-954.

Carney C.E., et al., "Nanodiscs as a Modular Platform for Multimodal MR-Optical Imaginga," Bioconjugate Chemistry, May 2015, vol. 26 (5), pp. 899-905.

Chang C.A., et al., "Synthesis, Characterization, and Crystal Structures of M(D03A) (M=Fe, Gd) and Na[M(DOTA)] (M=Fe, Y, Gd)," Inorganic Chemistry, Aug. 1993, vol. 32 (16), pp. 3501-3508.

Chen Liu Qi; et al., "Evaluating pH in the Extracellular Tumor Microenvironment Using CEST MRI and Other Imaging Methods", Adv. Radiol., 2015, 1-39.

Chen Z., et al., "Fullerenes Cn 36 (n = 0, 2+, 2−) and their B- and N-doped Analogues," Chemical Physics Letters, Oct. 2000, vol. 329 (2000), pp. 47-51.

Coderre J.A., et al., "Selective Delivery of Boron by the Melanin Precursor Analogue p-Boronophenylalanine to Tumors Other Than Melanoma," Cancer Research, Jan. 1990, vol. 50, pp. 138-141.

(56) References Cited

OTHER PUBLICATIONS

Cross L.C., et al., "IUPAC Commission on Nomenclature of Organic Chemistry, Rules for Nomenclature of Organic Chemistry Section E: Stereochemistry, ," Pure and Applied Chemistry, 1976, vol. 45, pp. 11-30.
Cui P., et al., "An Ion Pair Scandium Hydride Supported by a Dianionic (NNNN)-type Macrocycle Ligand," Chemical Communications, 2014, vol. 50, pp. 424-426.
Cui P., et al., "Dehydrogenation of Amine-borane Me2NH—BH3 Catalyzed by a Lanthanum-hydride Complex," Chemistry a European Journal, Sep. 2013, vol. 19 (40), pp. 13437-13444.
Cui P., et al., "Heterometallic Potassium Rare-Earth-Metal Allyl and Hydrido Complexes Stabilized by a Dianionic (NNNN)-Type Macrocyclic Ancillary Ligand," Organometallics, 2013, vol. 32 (5), pp. 1176-1182.
Cvrtila I., et al., "Redox Control over Acyl Hydrazone Photoswitches," Journal of the American Chemical Society, Jul. 2017, vol. 139 (36), pp. 12459-12465.
Delepine A., et al., "Selective Mono-n-alkylation of Triethylenetetraamine. A New Versatile Route to Polylinear Aza-ligands," Tetrahedron Letters, May 2009, vol. 50 (21), pp. 2521-2524.
Delepine A., et al., "From Flexible to Constrained Tris(tetraamine) Ligands: Synthesis, Acid-Base Properties, and Structural Effect on the Coordination Process with Nucleotides," European Journal of Organic Chemistry, Oct. 2010, vol. 2010 (28), pp. 5380-5390.
Di; Gregorio et al, "Gd loading by hypotonic swelling: an efficient and safe route for cellular labeling", Contrast Media & Molecular Imaging, 2013, vol. 8, 475-486.
Di Gregorio E., et al., "Gd Loading by Hypotonic Swelling: an Efficient and Safe Route for Cellular Labeling," Contrast Media & Molecular Imaging, Nov.-Dec. 2013, vol. 8 (6), pp. 475-486.
Eggenspiller A., et al., "Design of Porphyrin-dota-Like Scaffolds as All-in-One Multimodal Heterometallic Complexes for Medical Imaging," European Journal of Organic Chemistry, Oct. 2013, vol. 2013 (29), pp. 6629-6643.
European Search Report for Application No. EP15170658.7, dated Dec. 4, 2015, 6 pages.
Faulkner S., et al., "Lanthanide-Sensitized Lanthanide Luminescence: Terbium-Sensitized Ytterbium Luminescence in a Trinuclear Complex," Journal of the American Chemical Society, Aug. 2003, vol. 125 (35), pp. 10526-10527.
Fisher M.J., et al., "Trivalent Gd-DOTA Reagents for Modification of Proteins," RSC Advances, Dec. 2015, vol. 5 (116), pp. 96194-96200.
Fleischer E.B., et al., "Conversion of Aliphatic and Alicyclic Polyalcohols to the Corresponding Primary Polyamines," The Journal of Organic Chemistry, Oct. 1971, vol. 36 (20), pp. 3042-3044.
Frenzel T., et al., "Stability of Gadolinium-Based Magnetic Resonance Imaging Contrast Agents in Human Serum at 37°C," Investigative Radiology, Dec. 2008, vol. 43 (12), pp. 817-828.
Fries Peter; MD, et al, "P03277—A New Approach to Achieve High-Contrast Enhancement", Investigative Radiology, Dec. 2015, vol. 50 No. 12, 835-842.
Galibert M., et al., "RGD-cyclam Conjugate: Synthesis and Potential Application for Positron Emission Tomography," Bioorganic & Medicinal Chemistry Letters, Sep. 2010, vol. 20 (18), pp. 5422-5425.
Ganb A., et al., "Synthesis and Structural Characterization of a Cyclen-Derived Molecular Cage," Organic Letters, Nov. 2015, vol. 17 (23), pp. 5850-5853.
Giesel F.L., et al., "High-relaxivity Contrast-enhanced Magnetic Resonance Neuroimaging: a Review," European Radiology, Oct. 2010, vol. 20 (10), pp. 2461-2474.
Grauer A., et al., "Synthetic Receptors for the Differentiation of Phosphorylated Peptides with Nanomolar Affinities," Chemistry a European Journal, Oct. 2008, vol. 14 (29), pp. 8922-8927.
Greene; And Wuts., "Chapter 7: Protection For The Amino Group", Protective Groups in Organic Synthesis, John Wiley & Sons, Inc., 1999, Third Edition, 494-653.

Grunberg J., et al., "DOTA-Functionalized Polylysine: A High Number of DOTA Chelates Positively Influences the Biodistribution of Enzymatic Conjugated Anti-Tumor Antibody chCE7agl," PLoS One, 2013, vol. 8 (4), pp. 1-11.
Harrison V.S.R., et al., "A Multimeric MR-optical Contrast Agent for Multimodal Imaging," Chemical Communications, Aug. 2014, vol. 50, pp. 11469-11471.
Harrison V.S.R., et al., "Multimeric Near IR-MR Contrast Agent for Multimodal In Vivo Imaging," Journal of the American Chemical Society, Jul. 2015, vol. 137 (28), pp. 9108-9116.
Hayes W., et al., "One-pot Synthesis of Multivalent Arrays of Mannose Monoand Disaccharides," Tetrahedron, Sep. 2003, vol. 59 (40), pp. 7983-7996.
Wang L., et al., "Catalytic Cooperativity, Nuclearity, and O2/H2O2 Specificity of Multi-Copper(II) Complexes of Cyclen-Tethered Cyclotriphosphazene Ligands in Aqueous Media," European Journal of Inorganic Chemistry, Nov. 2017, vol. 2017 (42), pp. 4899-4908.
Wang Y., et al., "Incidence of Nephrogenic Systemic Fibrosis After Adoption of Restrictive Gadolinium-based Contrast Agent Guidelines," Radiology, Jul. 2011, vol. 260 (1), pp. 105-111.
Wangler C., et al., "Antibody-dendrimer Conjugates: the Number, Not the Size of the Dendrimers, Determines the Immunoreactivity," Bioconjugate Chemistry, Apr. 2008, vol. 19 (4), pp. 813-820.
Wangler C., et al., "Improved Syntheses and Applicability of Different DOTA Building Blocks for Multiply Derivatized Scaffolds," Bioorganic & Medicinal Chemistry, Mar. 2008, vol. 16 (5), pp. 2606-2616.
Werner E.J., et al., "High-Relaxivity MRI Contrast Agents: Where Coordination Chemistry Meets Medical Imaging," Angewandte Chemie, 2008, vol. 47 (45), pp. 8568-8580.
Wischnjow A., et al., "Renal Targeting: Peptide-Based Drug Delivery to Proximal Tubule Cells," Bioconjugate Chemistry, Apr. 2016, vol. 27 (4), pp. 1050-1057.
Wu X., et al., "Synthesis and Evaluation of a Peptide Targeted Small Molecular Gd-DOTA Monoamide Conjugate for MR Molecular Imaging of Prostate Cancer," Bioconjugate Chemistry, Aug. 2012, vol. 23 (8), pp. 1548-1556.
Xiao; Yu-Dong et al, "MRI contrast agents: Classification and application (Review)", International Journal of Molecular Medicine, 2016, 38, 1319-1326.
Xu H., et al., "Tetraphenylethene Based Zinc Complexes as Fluorescent Chemosensors for Pyrophosphate Sensing," Chinese Chemical Letters, Jul. 2015, vol. 26 (7), pp. 877-880.
Yang L., et al., "Nephrogenic Systemic Fibrosis and Class Labeling of Gadolinium-based Contrast Agents by the Food and Drug Administration," Radiology, Oct. 2012, vol. 265 (1), pp. 248-253.
Yang X., et al., "Synthesis and Characterization of Side Group-Modified Tetradentate Cyclotriphosphazene Derivatives," Phosphorus, Sulfur, and Silicon and the Related Elements, 2012, vol. 187 (6), pp. 722-727.
Yoo C.E., et al., "Degradation of Myoglobin by Polymeric Artificial Metalloproteases Containing Catalytic Modules with Various Catalytic Group Densities: Site Selectivity in Peptide Bond Cleavage," Journal of the American Chemical Society, Nov. 2003, vol. 125 (47), pp. 14580-14589.
Zhang W., et al., "A Tetranuclear Gadolinium(III) Macrocyclic Complex: Towards High Relaxivity with the Rigid Linkers for Magnetic Resonance Imaging Contrast Agent," Zeitschrift Fur Anorganische Und Allgemeine Chemie, Mar. 2015, vol. 641 (3-4), pp. 578-585.
Zhang Y., et al., "Small Cyclenylmidazolium-Containing Molecules and Their Interactions with DNA," Chemistry & Biodiversity, 2014, vol. 11, pp. 233-244.
Zhao G., et al., "Two Multinuclear GdIII Macrocyclic Complexes as Contrast Agents with High Relaxivity and Stability Using Rigid Linkers," Inorganica Chimica Acta, Sep. 2013, vol. 406, pp. 146-152.
Zhou Z., et al., "Peptide Targeted Tripod Macrocyclic Gd(III) Chelates for Cancer Molecular MRI," Biomaterials, Oct. 2013, vol. 34 (31), pp. 7683-7693.
Zompa L.J., et al., "Equilibrium Studies of Polynucleating Ligands. I. The Interaction of Tetrakis(aminomethyl)methane with Cop-

(56) References Cited

OTHER PUBLICATIONS per(II) and Hydrogen Ions," Journal of the American Chemical Society, Nov. 1966, vol. 88 (22), pp. 5186-5191.

Zulkefeli M., et al., "Design and Synthesis of a Stable Supramolecular Trigonal Prism Formed by the Self-assembly of a Linear Tetrakis(Zn2+-cyclen) Complex and Trianionic Trithiocyanuric Acid in Aqueous Solution and its Complexation with DNA (Cyclen = 1,4,7,10-tetraazacyclododecane)," Inorganic Chemistry, Oct. 2009, vol. 48 (19), pp. 9567-9578.

"Decision of the Opposition Division on EP3303307B1", Dec. 20, 2021.

"Declaration by Dr. Markus Berger, Senior Scientist and Dr. Thomas Frenzel, Senior Scientist, Bayer AG", Jul. 2, 2021.

Fischer; Gunter, "Chemical aspects of peptide bond isomerisation", The Royal Society of Chemistry, Chem Soc Rev, 2000, 29, 119-127.

Kompp; Kompakt., "Basislexikon Chemie", 1999, 2586.

Livramento; et al, "A benzene-core trinuclear GdIII complex: towards the optimization of relaxivity for MRI contrast agent applications at hight magnetic field", The Royal Society of Chemistry 2008, 2008, 1195-1202.

"NMRD measurements—final report and Sample characteristics of the samples used in the experimental report", dated Dec. 19, 2014.

Rinck; et al, "Field strength and dose dependence of contrast enhancement by gadolinium-based MR contrast agents", European Radiology, 1999, vol. 9, 998-1004.

Rompp; Kompakt., "Basislexikon Chemie", 1998, 1213-1214.

Rompp; Kompakt., "Basislexikon Chemie", 1999, 2436.

\* cited by examiner

FORMULATION OF CONTRAST MEDIA AND PROCESS OF PREPARATION THEREOF

CROSS REFERENCE TO RELATED APPLICATIONS

The present application is a U.S. national stage filing under 35 U.S.C. § 371 of International Application No. PCT/EP2019/082117, filed 21 Nov. 2019, which claims priority to European Patent Application No. EP 18208090.3, filed 23 Nov. 2018, the disclosures of each of which are incorporated in their entirety herein by this reference.

The present invention relates to formulations of contrast agents, in particular of paramagnetic metal ion chelates, in particular for magnetic resonance imaging, and to industrially applicable processes for obtaining said formulations.

BACKGROUND

Various contrast agents based on lanthanide (paramagnetic metal) chelates, in particular gadolinium chelates, described for example in document U.S. Pat. No. 4,647,447, are known. These products are termed GBCAs (Gadolinium-based Contrast Agents). Several GBCAs have been approved for clinical use and are commercially available: in particular linear Gd-chelates, such as gadopentetate dimeglumine (Magnevist®, based on DTPA), gadodiamide (Omniscan®, based on DTPA-BMA), gadoversetamide (OptiMARK®, based on DTPA-BMEA) and in particular macrocyclic Gd-chelates, gadoterate meglumine (Dotarem®, based on DOTA), gadoteridol (ProHance®, based on HP-DO3A), gadobutrol (Gadovist®, based on BT-DO3A, Butrol), gadoxetic acid (Primovist®, based on EOB-DTPA) and gadobenate dimeglumine (MultiHance®, based on BOPTA).

These compounds will, in the remainder of the text, be referred to without distinction as "Gd-chelates" or "chelates" and their ligands as "chelating ligands".

Some GBCAs are described in the following documents U.S. Pat. Nos. 6,440,956, 5,403,572, EP 0 438 206, WO 93/011800.

Magnetic resonance imaging (MRI) contrast agents may be characterized by their longitudinal ($r_1$) and transverse ($r_2$) relaxivities. Relaxivity is the degree to which the agent can enhance the longitudinal or transverse water relaxation rate constant ($R_1=1/T_1$ or $R_2=1/T_2$, respectively) normalized to the concentration of the contrast agent. Relaxivity is a measure of the efficacy of the contrast agent (Jacques V. et al. Invest. Radiol. 2010 October; 45(10): 613-624). The various GBCAs differ, for example, in their relaxivities which are dependent on factors such as magnetic field strengths, temperature, and different intrinsic factors of the metal chelates. The intrinsic relaxivity influencing parameters are mainly the number of water molecules directly bound to the gadolinium (so-called inner-sphere water, q), the mean residence time of the inner sphere water molecules ($\tau m$), the number and residence times of water molecules in the second hydration sphere (so-called second sphere water), and the rotational diffusion ($\tau r$) (Helm L. et. al., Future Med. Chem. 2010; 2: 385-396). In terms of their relaxivity, commercially available GBCAs are similar to each other and falling within a range of 4 to 7 L mmol$^{-1}$s$^{-1}$.

A further characteristic of GBCAs is the complex stability of the Gd-chelate.

In certain GBCAs, small amounts of free gadolinium ions may be released after administration to the patient or decomplexation may occur during storage/shipping. This has led to a search for technical solutions to limit free metal ion exposure in order to safely solve the complex technical problem of tolerance in the patient. For example since 2006, a pathological condition known as NSF (Nephrogenic Systemic Fibrosis) has been at least partly linked to the administration of GBCAs and subsequent presence of gadolinium in the body. This disease has resulted in a warning by health authorities with respect to specific GBCAs used in patients with reduced or no kidney function. Another example is the accumulation of gadolinium in the brain, which has been observed after multiple administration of certain linear GBCAs. As the administration of contrast agents is often repeated during the patient's treatment cycle for guiding and monitoring the effectiveness of a therapeutic treatment, the risk of patient exposure to the free gadolinium ions increases.

The complex problem of the tolerance of new GBCAs must always be considered.

As described herein, development of new high relaxivity contrast agents with higher efficacy can lead to a significant reduction in the administered dose and thus reduces the risk of accumulation of Gd in the body.

Another strategy for limiting this risk is the selection of lanthanide chelates which have the highest possible thermodynamic stabilities and kinetic inertness. This is because the higher the stability and inertness of the chelate, the amount of lanthanide released over time is reduced.

Several strategies for improving Gd-chelate tolerance are described, for example, in U.S. Pat. No. 5,876,695 and WO 2009/103744, which disclose formulations comprising an excess of free chelating ligand, intended to inhibit an unwanted accumulation of gadolinium, by complexing any released gadolinium. U.S. Pat. No. 5,876,695 describes an excess of linear chelating ligand, in particular of free DTPA. This formulation strategy has been used for commercial products such as Magnevist®. WO 2009/103744 describes a similar formulation strategy, based on the addition of free chelating ligand, in particular of free DOTA, so as to have a very small excess of said free chelating ligand to complex any released metal, resulting in a zero concentration of free gadolinium. However, certain chelating ligands may also have a toxicity profile that limits the amount of free ligand that can be added to the formulation.

US 2004/0170566, EP 0 454 078 and U.S. Pat. No. 5,876,695 describe fomulations containing "weak" complexes or salts of chelating ligands and transition metals or alkaline-earth metals with much lower thermodynamic stability than the corresponding Gd-chelate. These "weak" complexes (e.g. Ca-, Zn-, Na- or Mg-complexes) undergo transmetallation in the presense of free lanthanide as they are thermodynamically more stable.

US 2016/0101196A1 describes a formulation composition comprising a PCTA derived mono-Gd-complex and also comprising a calcium complex of 1,4,7,10-tetraazacyclodo-decane-1,4,7,10-tetraacetic acid (Ca-DOTA).

BRIEF DESCRIPTION

The Applicant has carried out studies on the specific case of the DO3A-derived tetra-chelates as described in WO 2016/193190 and WO 2018/096082. The strategies described above have been developed only for monomeric Gd-chelates and not for the DO3A-derived tetra-chelates as described herein.

It has now been found, as described herein, that the various embodiments of the formulations of the present disclosure have surprising and advantageous properties.

Pharmaceutical formulations described herein which comprise DO3A-derived tetra-chelates of lanthanide ions, disclosed in WO 2016/193190 and WO 2018/096082, displaying high relaxivity as well as other useful properties for use as a contrast agent in medical imaging procedures, for example in magnetic resonance imaging (MRI) procedures are described.

According to one embodiment, formulations comprising small amounts of a lanthanide ion scavenging agent, such as a scavenging agent comprising a chelating ligand that forms a strong complex with the free lanthanide ion, are described. The scavenging agent may comprise the free form of the chelating ligand (i.e., the ligand in an uncomplexed form) and/or the ligand as a complex with a weakly binding metal ion, such as ions of the alkali metals or the alkaline earth metals or weakly binding transition metal ions.

According to certain embodiments, the Applicant has discovered that the addition of small amounts of the calcium complex of 10-[2,3-dihydroxy-1-(hydroxymethyl)propyl]-1,4,7,10-tetraazacyclododecane-1,4,7-triacetic acid (Ca-BT-DO3A, Calcobutrol) to a formulation comprising a DO3A-derived tetra-chelate described herein, such as a $Gd_4$-DO3A-derived tetra-chelate, ensures the absence of free paramagnetic metal ion in the formulation, in particular in the injectable solution, while preserving the performance levels as a contrast medium in medical imaging procedures.

According to other embodiments, similar effects may be achieved, when the formulation comprises a poly-chelate, which is a chelate having more than one metal chelating site, i.e. having 2-64 metal chelating sites, and includes amounts of ligand chelate with sub-stoichiometric amounts of paramagnetic metal ions which provide sufficient chelating activity to bind any free paramagnetic metal ions in the formulation.

According to other embodiments, similar effects may be achieved, when the formulation comprises a DO3A-derived tetra-chelate, such as a $Gd_4$-DO3A-derived tetra-chelate, and includes amounts of ligand chelate with sub-stoichiometric amounts of paramagnetic metal ions (i.e. 0, 1, 2 or 3 paramagnetic metal ions) which provide sufficient chelating activity to bind any free paramagnetic metal ions in the formulation. In other embodiments, the amount of ligand chelate with sub-stoichiometric amounts of paramagnetic metal ion may have a corresponding amount of one to four weakly binding metal ions, as described herein.

The pharmaceutical formulations of certain embodiments have a concentration of free paramagnetic metal of less than or equal to 5 ppm (m/v), i.e. in the range of 0 to 5 ppm (m/v) (inclusive), and in certain embodiments less than or equal to 2 ppm (m/v), i.e. in the range of 0 to 2 ppm (m/v) (inclusive), and in certain embodiments less than or equal to 0.5 ppm (m/v), i.e. in the range of 0 to 0.5 ppm (m/v) (inclusive).

According to various embodiments, the viscosity of the pharmaceutical formulations of the current disclosure has been found to be only slightly higher than for isotonic sodium chloride solution. According to certain embodiments, the pharmaceutical formulations described herein may have a lower viscosity compared to conventional contrast formulations. The low viscosity leads to a good local tolerance of the intravenous bolus application and allows a convenient and reproducible application through a long and thin catheter during hand injection (less pressure required) and/or avoids fluid flow rate changes during fluid transitions from contrast to saline injection during injections with powered injection systems.

In contrast to the available market products, in several embodiments of the pharmaceutical formulation of the present disclosure, the formulation is isotonic with blood plasma, which also increases the tolerability at the site of injection when compared with the hyperosmolar formulations of commercially available imaging contrast formulations.

DETAILED DESCRIPTION

One subject of the present disclosure therefor relates to a liquid pharmaceutical formulation comprising a DO3A-derived tetra-chelate.

Another subject of the present disclosure relates to a liquid pharmaceutical formulation comprising a DO3A-derived tetra-chelate, and further comprising one or more scavenging agents, which are defined as compounds capable of forming a complex with free paramagnetic metal ion M.

Another subject of the present disclosure relates to a liquid pharmaceutical formulation comprising a DO3A-derived tetra-chelate and a calcium complex of 10-[2,3-dihydroxy-1-(hydroxymethyl)propyl]-1,4,7,10-tetraazacyclododecane-1,4,7-triacetic acid (Ca-BT-DO3A, Calcobutrol).

Another subject of the present disclosure relates to a liquid pharmaceutical formulation comprising a DO3A-derived tetra-chelate and DO3A-derived tetra-chelates with sub-stoichiometric amounts of paramagnetic metal ions.

Another subject of the disclosure relates to a contrast medium for medical imaging, such as magnetic resonance imaging, comprising said liquid pharmaceutical formulation.

Another subject of the present disclosure relates to a process for preparing said liquid pharmaceutical formulation.

The present disclosure also relates to said liquid pharmaceutical formulation or said contrast medium for use thereof in a diagnostic method, such as a magnetic resonance imaging diagnostic method.

As described herein, a chelate of general formula (I), which is a chelate between a chelating ligand of general formula (II) and four paramagnetic metal ions, will be referred to as "DO3A-derived tetra-chelate". More specifically and unless otherwise indicated, the complex between the chelating ligand of general formula (II) and gadolinium ($Gd^{3+}$) ions will be referred to as "$Gd_4$-DO3A-derived tetra-chelate".

The chelating ligand of general formula (II) is the free ligand (i.e., no complexed metal ion) and will be referred to as "DO3A-derived tetra-ligand".

DO3A-derived tetra-chelates with sub-stoichiometric amounts of paramagnetic metal ions are compositions containing DO3A-derived tetra-chelates and further including one or more chelates between a DO3A-derived tetra-ligand of general formula (II) and sub-stoichiometric amounts of paramagnetic metal ions, such as one, two or three paramagnetic metal ions, and/or containing the DO3A-derived tetra-ligand of general formula (II), or mixtures thereof. In various embodiments, the DO3A-derived tetra-ligand comprising sub-stoichiometric amounts of paramagnetic metal ions may include sub-stoichiometric amounts of one or more weak binding metal ions. As used herein, the term "weak binding metal ions" include metal ions for the alkali metals, alkaline earth metals, and transition metals that have a binding affinity for the DO3A-derived tetra-chelate that is less than the binding affinity of the DO3A-derived tetra-chelate and the lanthanide metal ion. In various embodiments, the weak binding metal ions may include lithium, calcium, sodium, zinc, potassium, or magnesium ions.

Gd$_4$-DO3A-derived tetra-chelates with sub-stoichiometric amounts of paramagnetic gadolinium ions are compositions containing Gd$_4$-DO3A-derived tetra-chelates and further including chelates between a DO3A-derived tetra-ligand of general formula (II) and one, two or three Gd$^{3+}$ ions, and/or containing the DO3A-derived tetra-ligand of general formula (II) as a free ligand, or mixtures thereof. In various embodiments, the Gd$_4$-DO3A-derived tetra-ligand comprising sub-stoichiometric amounts of paramagnetic gadolinium ions and/or the free DO3A-derived tetra-ligand may include sub-stoichiometric or stoichiometric amounts, respectively, of one or more weak binding metal ions in the gadolinium-free ligating sites.

A sub-stoichiometric chelate between a DO3A-derived tetra-ligand of general formula (II) and three paramagnetic metal ions will be referred to as "M$_3$-DO3A-derived chelate". A sub-stoichiometric chelate between a DO3A-derived tetra-ligand of general formula (II) and two paramagnetic metal ions will be referred to as "M$_2$-DO3A-derived chelate". A sub-stoichiometric chelate between a DO3A-derived tetra-ligand of general formula (II) and one paramagnetic metal ion will be referred to as "M-DO3A-derived chelate". According to various embodiments, these sub-stoichiometric chelates as well as the DO3A-derived tetra-ligand of general formula (II), which also is a sub-stoichiometric chelate, can be present in the formulation.

More specifically and unless otherwise indicated, a sub-stoichiometric chelate between a DO3A-derived tetra-ligand of general formula (II) and three Gd$^{3+}$ ions will be referred to as "Gd$_3$-DO3A-derived chelate", a sub-stoichiometric chelate between a DO3A-derived tetra-ligand of general formula (II) and two Gd$^{3+}$ ions will be referred to as "Gd$_2$-DO3A-derived chelate", and a sub-stoichiometric chelate between a DO3A-derived tetra-ligand of general formula (II) and one Gd$^{3+}$ ion will be referred to as "Gd-DO3A-derived chelate".

In general, one aspect of the present disclosure includes pharmaceutical formulations of poly-ligands of paramagnetic metal ions, such as lanthanide metal ions, having two or more metal chelating sites, such as from 2-64 metal chelating sites, wherein each of the metal chelating sites has a paramagnetic metal ion bound thereto, wherein the formulation further comprises amounts of the poly-ligand having a sub-stoichiometric amount of the paramagnetic metal ions bound thereto.

According to these embodiments, the chelating sites of the poly-ligand having sub-stoichiometric amounts of paramagnetic metal ions may be free (i.e., no bound metal) or may have a weak metal ion bound thereto. Further, according to these embodiments, one or more of the chelating sites of the poly-ligand having sub-stoichiometric amounts of paramagnetic metal ions may be free (i.e., no bound metal) or may have a weak metal ion bound thereto. Pharmaceutical formulations such as these will have incorporated therein a metal scavenging moiety that is capable of binding to any released paramagnetic metal ion that may be released during storage, shipping, or during an injection protocol, thereby preventing its release into a patient's blood stream or organs.

The complex between 10-[2,3-dihydroxy-1-(hydroxymethyl)propyl]-1,4,7,10-tetraazacyclo-dodecane-1,4,7-triacetic acid (Butrol) and calcium ions, which is known as Calcobutrol, will be referred to as "Ca-BT-DO3A".

In accordance with a first aspect, the present disclosure covers a liquid pharmaceutical formulation comprising a DO3A-derived tetra-chelate of general formula (I):

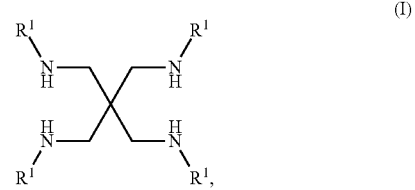

in which
R$^1$ represents a group selected from:

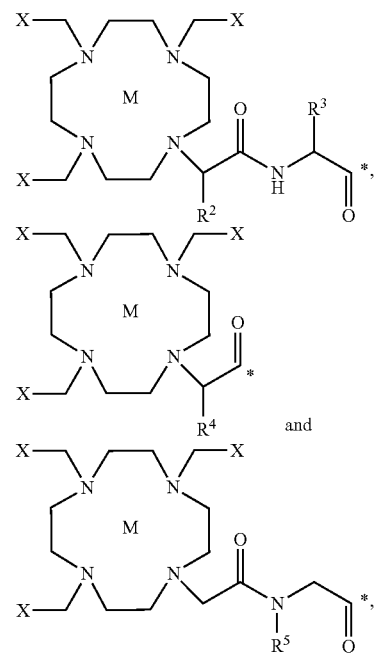

in which group * indicates the point of attachment of said group with the rest of the molecule, R$^2$, R$^3$, and R$^4$ independently of each other represents a hydrogen atom or a group selected from:
C$_1$-C$_6$-alkyl, C$_3$-C$_6$-cycloalkyl, (C$_1$-C$_2$-alkoxy)-(C$_2$-C$_3$-alkyl)-, and phenyl,
wherein said C$_1$-C$_6$-alkyl group is optionally substituted, identically or differently, with a phenyl substituent, which phenyl substituent is optionally substituted, one, two or three times, identically or differently, with a halogen atom or a group selected from:
C$_1$-C$_3$-alkyl, C$_1$-C$_3$-haloalkyl, and C$_1$-C$_3$-alkoxy, and
wherein said phenyl group is optionally substituted, one, two or three times, identically or differently, with a halogen atom or a group selected from:
C$_1$-C$_3$-alkyl, C$_1$-C$_3$-haloalkyl, and C$_1$-C$_3$-alkoxy, R$^5$ represents a group selected from:
C$_1$-C$_6$-alkyl, C$_3$-C$_6$-cycloalkyl, (C$_1$-C$_2$-alkoxy)-(C$_2$-C$_3$-alkyl)- and phenyl,
wherein said C$_1$-C$_6$-alkyl group is optionally substituted, identically or differently, with a phenyl substituent, which phenyl substituent is optionally substituted, one, two or three times, identically or differently, with a halogen atom or a group selected from:

$C_1$-$C_3$-alkyl, $C_1$-$C_3$-haloalkyl, and $C_1$-$C_3$-alkoxy, and wherein said phenyl group is optionally substituted, one, two, or three times, identically or differently, with a halogen atom or a group selected from:

$C_1$-$C_3$-alkyl, $C_1$-$C_3$-haloalkyl, and $C_1$-$C_3$-alkoxy,

X represents a group C(=O)OH or C(=O)O$^-$, and

M represents an ion of a paramagnetic metal, or a stereoisomer, a tautomer or a salt thereof, or a mixture of same, said formulation comprising
a pharmaceutically acceptable solvent,
and optionally comprising a buffer,
wherein the DO3A-derived tetra-chelate has a concentration in the formulation in a range of 1 to 1000 mmol paramagnetic metal ion/L (inclusive), wherein the ion of the paramagnetic metal is not Gd$^{3+}$, and in a range of 60 to 750 mmol paramagnetic metal ion/L (inclusive) wherein the ion of the paramagnetic metal can also be Gd$^{3+}$, particularly in a range of 70 to 700 mmol paramagnetic metal ion/L (inclusive), particularly in a range of 80 to 650 mmol paramagnetic metal ion/L (inclusive), particularly in a range of 90 to 600 mmol paramagnetic metal ion/L (inclusive), particularly in a range of 100 to 500 mmol paramagnetic metal ion/L (inclusive), particularly in a range of 150 to 450 mmol paramagnetic metal ion ion/L (inclusive), more particularly in a range of 200 to 400 mmol paramagnetic metal ion/L (inclusive), and even more particularly in a range of 250 to 350 mmol paramagnetic metal ion/L (inclusive).

Definitions

All concentrations or dosings references related to the various contrast formulations of this disclosure, unless otherwise noted, refer to concentration of the paramagnetic metal ion. This is important, because the tetrameric complexes carry 4 paramagnetic metal ions per molecule. Thus, a formulation comprising Gd$_4$-DO3A-derived tetra-chelate having a 1 mmol/L concentration of the ligand/metal chelate would have a concentration of 4 mmol/L of the Gd$^{3+}$ ion.

The terms "formulation" and "pharmaceutical formulation" mean, according to the disclosure, a solution comprising at least a DO3A-derived tetra-chelate of formula (I), supra, in a "pharmaceutically acceptable solvent", wherein the term "pharmaceutically acceptable solvent" is intended to mean a solvent that is suitable with parenteral application, i.e., water, an aqueous solution, or one or more compounds selected from the list of solvents herein, that is capable of substantially solubilizing the DO3A-derived tetra-chelate, which solution optionally comprises further one or more pharmaceutically suitable excipients.

Pharmaceutically suitable excipients include, inter alia,
solvents (for example water, ethanol, isopropanol, glycerol, propylene glycol and liquid polyethylene glycols),
buffers, acids, and/or bases (for example buffers comprising phosphates, carbonates, citrate, ascorbates, acetate, succinate, malate, maleate, lactate, tartrate, trometamol (TRIS, 2-amino-2-(hydroxymethyl)propane-1,3-diol), triethanolamine, HEPES (2-[4-(2-hydroxyethyl)-1-piperazine]ethanesulfonic acid), MES (2-morpholinoethanesulfonic acid), and sodium hydroxide, and hydrochloric acid),
isotonicity agents (for example glucose, sodium chloride, d-mannitol, sorbitol, sucrose, trehalose, and propylene glycol),
stabilisers (for example antioxidants such as, for example, ascorbic acid, ascorbyl palmitate, and sodium ascorbate),
preservatives (for example sorbic acid).

The term "buffer solution" means, according to the disclosure, a solution in a pharmaceutically acceptable solvent which comprises a buffer, which buffer is chosen from citrate, lactate, acetate, tartrate, malate, maleate, phosphate, succinate, ascorbate, carbonate, trometamol (TRIS, 2-amino-2-(hydroxymethyl)propane-1,3-diol), HEPES (2-[4-(2-hydroxyethyl)-1-piperazine]ethanesulfonic acid) and MES (2-morpholinoethanesulfonic acid) and mixtures of any thereof.

The term "substituted" means that one or more hydrogen atoms on the designated atom or group are replaced with a selection from the indicated group, provided that the designated atoms normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing any hydrogen atom with a non-hydrogen substituent on any available carbon atom.

Should a composite substituent be composed of more than one part, e.g. ($C_1$-$C_2$-alkoxy)-($C_2$-$C_3$-alkyl)-, it is possible for a given part to be attached at any suitable position of said composite substituent, e.g. it is possible for the $C_1$-$C_2$-alkoxy part to be attached to any suitable carbon atom of the $C_2$-$C_3$-alkyl part of said ($C_1$-$C_2$-alkoxy)-($C_2$-$C_3$-alkyl)- group. A hyphen at the beginning or at the end of such a composite substituent indicates the point of attachment of said composite substituent to the rest of the molecule.

The term "comprising" when used in the specification includes "consisting essentially of" and "consisting of".

The terms as mentioned in the present text have the following meanings:

The term "halogen atom" means a fluorine, chlorine, bromine or iodine atom, particularly a fluorine, chlorine, or bromine atom.

The term "$C_1$-$C_6$-alkyl" means a linear or branched, saturated, monovalent hydrocarbon group having 1, 2, 3, 4, 5 or 6 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group, or an isomer thereof. Particularly, said group has 1, 2, 3 or 4 carbon atoms ("$C_1$-$C_4$-alkyl"), e.g. a methyl, ethyl, propyl, isopropyl, butyl, sec-butyl isobutyl, or tert-butyl group, more particularly 1, 2 or 3 carbon atoms ("$C_1$-$C_3$-alkyl"), e.g. a methyl, ethyl, n-propyl or isopropyl group.

The term "$C_1$-$C_3$-alkyl" means a linear or branched, saturated, monovalent hydrocarbon group having 1, 2 or 3 carbon atoms, e.g., a methyl, ethyl, propyl, or isopropyl group.

The term "$C_2$-$C_3$-alkyl" means a linear or branched, saturated, monovalent hydrocarbon group having 2 or 3 carbon atoms, e.g., an ethyl, propyl, or isopropyl group.

The term "$C_1$-$C_2$-alkyl" means a linear, saturated, monovalent hydrocarbon group having 1 or 2 carbon atoms, e.g., a methyl or ethyl group.

The term "$C_3$-$C_6$-cycloalkyl" means a saturated, monovalent, monocyclic hydrocarbon ring which contains 3, 4, 5, or 6 carbon atoms. Said $C_3$-$C_6$-cycloalkyl group is, for example, a cyclopropyl, cyclobutyl, cyclopentyl, or cyclohexyl group.

The term "$C_1$-$C_3$-haloalkyl" means a linear or branched, saturated, monovalent hydrocarbon group in which the term "$C_1$-$C_3$-alkyl" is as defined supra, and in which one or more of the hydrogen atoms are replaced, identically or differently, with a halogen atom as defined supra. Particularly, said halogen atom is a fluorine atom. Said $C_1$-$C_3$-haloalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl, or 1,3-difluoropropan-2-yl.

The term "$C_1$-$C_3$-alkoxy" means a linear or branched, saturated, monovalent group of formula ($C_1$-$C_3$-alkyl)-O—, in which the term "$C_1$-$C_3$-alkyl" is as defined supra, e.g., a methoxy, ethoxy, n-propoxy, or isopropoxy group.

The term "$C_1$-$C_2$-alkoxy" means a linear saturated, monovalent group of formula ($C_1$-$C_2$-alkyl)-O—, in which the term "$C_1$-$C_2$-alkyl" is as defined supra, e.g., a methoxy or ethoxy group.

When a range of values is given, said range encompasses each terminal value and any sub-range within said range.

For example:

"$C_1$-$C_6$" encompasses $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_1$-$C_4$" encompasses $C_1$, $C_2$, $C_3$, $C_4$, $C_1$-$C_4$, $C_1$-$C_3$, $C_1$-$C_2$, $C_2$-$C_4$, $C_2$-$C_3$, and $C_3$-$C_4$;

"$C_1$-$C_3$" encompasses $C_1$, $C_2$, $C_3$, $C_1$-$C_3$, $C_1$-$C_2$, and $C_2$-$C_3$;

"$C_3$-$C_6$" encompasses $C_3$, $C_4$, $C_5$, $C_6$, $C_3$-$C_5$, $C_3$-$C_6$, $C_3$-$C_4$, $C_4$-$C_5$, $C_4$-$C_6$, and $C_5$-$C_6$.

It is possible for the compounds of general formulae (I) and (II) to exist as isotopic variants. The disclosure therefor may also include one or more isotopic variant(s) of the compounds of general formulae (I), (I-a), (I-b), (I-c), (II), (II-a), (II-b) and (II-c), and of any of the compounds having sub-stoichiometric amounts of paramagnetic metal ion, as described herein, such as deuterium-containing compounds of general formulae (I), (I-a), (I-b), (I-c), (II), (II-a), (II-b) and (II-c), and of any of the compounds having sub-stoichiometric amounts of paramagnetic metal ion, as described herein, where one or more $^1$H atoms has been replaced with a $^2$H atom.

The term "isotopic variant" of a compound is defined as a compound exhibiting an unnatural proportion of one or more of the isotopes that constitute such a compound.

The term "isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

It is possible for the compounds of general formula (I) to exist as stereochemical variants. The disclosure therefor also covers all stereochemical variants or combinations of compounds possessing one or more chiral centers as described herein, such as, compounds of general formulae (I), (I-a), (II), and (II-a), and any of the compounds having sub-stoichiometric amounts of paramagnetic metal ion, as described herein. The term "stereochemical variant" means that any chiral carbon center in the compound may exist in either the R or S stereochemical format and that compounds having more than one chiral carbon center may exist as any combination of enantiomers and diastereomers where the chiral centers may be any combination having either R or S stereochemistry at each chiral carbon center. The compound of general formula (I), (I-a), (II), and (II-a), and the compounds having sub-stoichiometric amounts of paramagnetic metal ion, i.e. the compounds of general formula (Gd$_3$-II-a), (Gd$_2$-II-a), (Gd-II-a), as described herein, may exist in enantiomerically or diastereomerically pure form, may be a mixture of enantiomers (such as a racemic mixture of enantiomers or a mixture that is enantiomerically enriched in the amount of one enantiomer relative to the other enantiomer), may be a mixture of diastereomers (such as a random mixture of two or more diastereoisomers or a mixture of two or more diastereoisomers wherein the mixture is enriched in the amount of one or more diastereoisomer relative to the amount of the one or more other diastereoisomers in the mixture).

The term "sub-stoichiometric amount" means less than the stoichiometric amount. When used in reference to a chelate having one or more chelating sites for a metal ion, sub-stoichiometric amounts of a metal ion means a molar amount of the metal ion that is less than the molar amount of available chelating sites capable of chelating to a metal ion.

The term "sub-stoichiometric chelate" means a chelate between a ligand and a sub-stoichiometric number of ions of a paramagnetic metal, i.e. a chelate between a tetra-ligand and 0, 1, 2 or 3 ions of a paramagnetic metal.

In accordance with a second embodiment of the first aspect, the present disclosure covers a liquid pharmaceutical formulation, supra, comprising a DO3A-derived tetra-chelate of general formula (I), supra, in which:

$R^2$ represents a hydrogen atom or a methyl group, $R^3$ and $R^4$ each represent a hydrogen atom, and $R^5$ represents a group selected from:

methyl, ethyl, isopropyl, 2-methylpropyl, benzyl, cyclopropyl, cyclopentyl, cyclohexyl, 2-methoxyethyl, 2-ethoxyethyl, and phenyl.

In accordance with a third embodiment of the first aspect, the present disclosure covers a liquid pharmaceutical formulation, supra, wherein the DO3A-derived tetra-chelate of formula (I) is selected from the chelates of formulae (I-a), (I-b), and (I-c) having structures as follows:

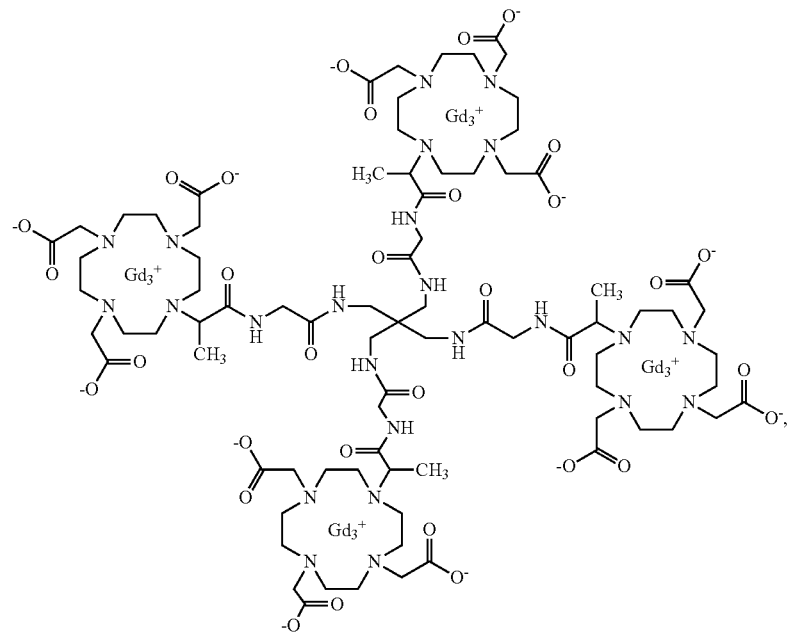
(I-a)
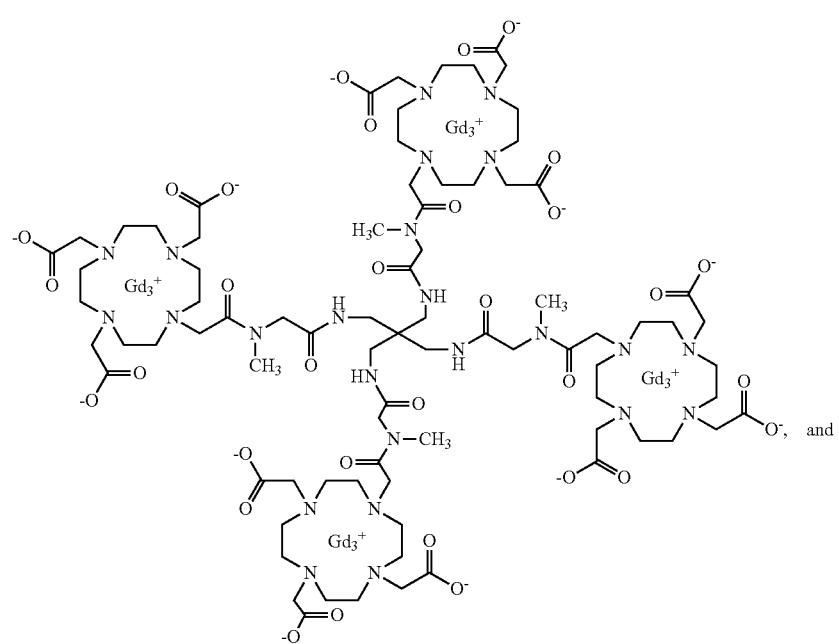
(I-b)
and

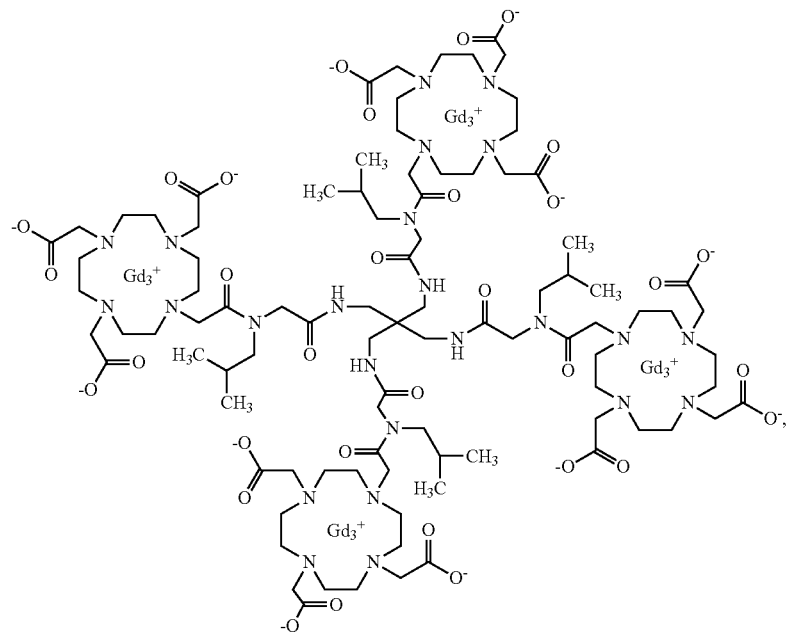

(I-c)

or a stereoisomer, a tautomer or a salt thereof, or a mixture of same.

In accordance with a fourth embodiment of the first aspect, the present disclosure covers a liquid pharmaceutical formulation, supra, wherein the DO3A-derived tetra-chelate of formula (I) has the formula (I-a) as follows:

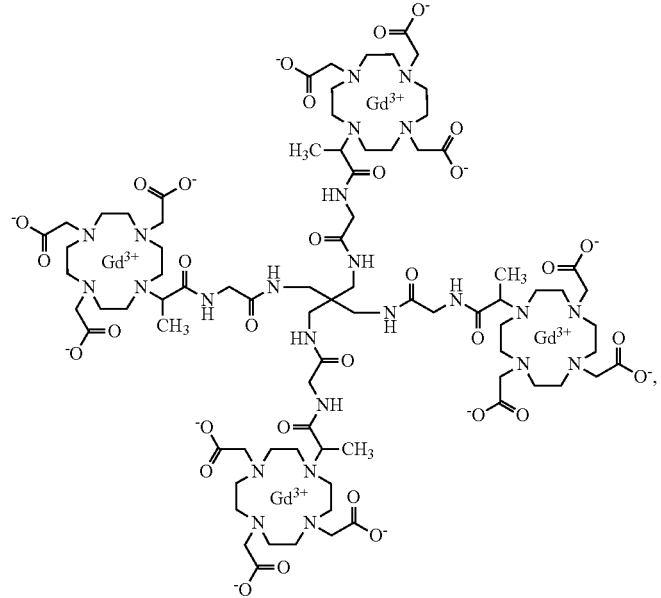

(I-a)

or a stereoisomer, a tautomer or a salt thereof, or a mixture of same.

In accordance with an fifth embodiment of the first aspect, the formulation according to the disclosure has a concentration of the $Gd_4$-DO3A-derived tetra-chelate of general formula (I), supra, in a range of 60 to 750 mmol $Gd^{3+}$/L (inclusive), particularly in a range of 70 to 700 mmol $Gd^{3+}$/L (inclusive), particularly in a range of 80 to 650 mmol $Gd^{3+}$/L (inclusive), particularly in a range of 90 to 600 mmol $Gd^{3+}$/L (inclusive), particularly in a range of 100 to 500 mmol $Gd^{3+}$/L (inclusive), particularly in a range of 150 to 450 mmol $Gd^{3+}$/L (inclusive), more particularly in a range of 200 to 400 mmol $Gd^{3+}$/L (inclusive), and even more particularly in a range of 250 to 350 mmol $Gd^{3+}$/L (inclusive).

In accordance with a sixth embodiment of the first aspect, the present disclosure covers a liquid pharmaceutical formulation, supra, comprising a DO3A-derived tetra-chelate of general formula (I), supra, characterized in that the DO3A-derived tetra-chelate of general formula (I) is a complex between
a DO3A-derived tetra-ligand of general formula (II):

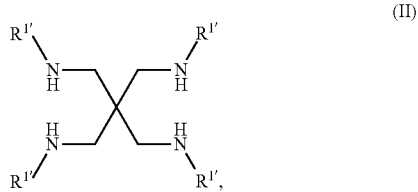

in which
$R^{1'}$ represents a group selected from:

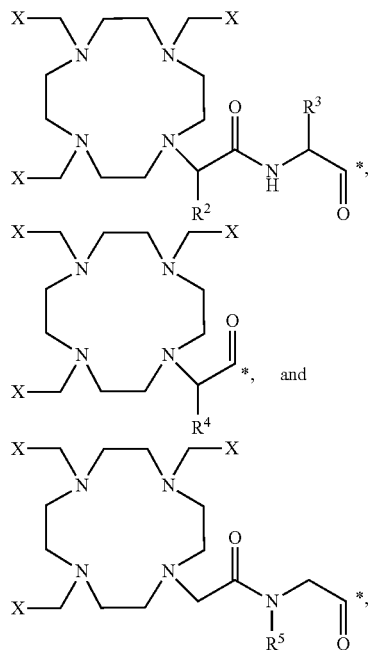

in which group * indicates the point of attachment of said group with the rest of the molecule,
$R^2$, $R^3$, and $R^4$ independently of each other represents a hydrogen atom or a group selected from:
$C_1$-$C_6$-alkyl, $C_3$-$C_6$-cycloalkyl, ($C_1$-$C_2$-alkoxy)-($C_2$-$C_3$-alkyl)-, and phenyl,
  wherein said $C_1$-$C_6$-alkyl group is optionally substituted, identically or differently, with a phenyl substituent, which phenyl substituent is optionally substituted, one, two, or three times, identically or differently, with a halogen atom or a group selected from:
    $C_1$-$C_3$-alkyl, $C_1$-$C_3$-haloalkyl, and $C_1$-$C_3$-alkoxy, and
  wherein said phenyl group is optionally substituted, one, two or three times, identically or differently, with a halogen atom or a group selected from:
    $C_1$-$C_3$-alkyl, $C_1$-$C_3$-haloalkyl, and $C_1$-$C_3$-alkoxy,
$R^5$ represents a group selected from:
$C_1$-$C_6$-alkyl, $C_3$-$C_6$-cycloalkyl, ($C_1$-$C_2$-alkoxy)-($C_2$-$C_3$-alkyl)-, and phenyl,
  wherein said $C_1$-$C_6$-alkyl group is optionally substituted, identically or differently, with a phenyl substituent, which phenyl substituent is optionally substituted, one, two, or three times, identically or differently, with a halogen atom or a group selected from:
    $C_1$-$C_3$-alkyl, $C_1$-$C_3$-haloalkyl, and $C_1$-$C_3$-alkoxy, and
  wherein said phenyl group is optionally substituted, one, two or three times, identically or differently, with a halogen atom or a group selected from:
    $C_1$-$C_3$-alkyl, $C_1$-$C_3$-haloalkyl, and $C_1$-$C_3$-alkoxy, and
X represents a group C(=O)OH or C(=O)O$^-$,
or a stereoisomer, a tautomer or a salt thereof, or a mixture of same,
and ions of a paramagnetic metal M.

In accordance with a seventh embodiment of the first aspect, the present disclosure covers a liquid pharmaceutical formulation, supra, comprising a DO3A-derived tetra-chelate of general formula (I), supra, characterized in that the DO3A-derived tetra-chelate of general formula (I) is a complex between
a DO3A-derived tetra-ligand of general formula (II):

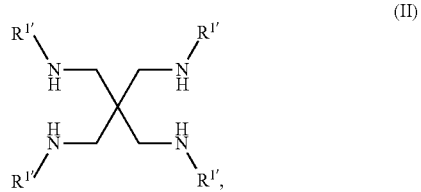

in which
$R^{1'}$ represents a group selected from:

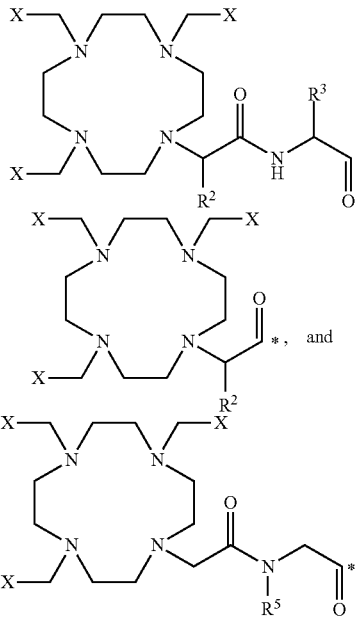

in which group * indicates the point of attachment of said group with the rest of the molecule,
$R^2$, $R^3$, and $R^4$ independently of each other represents a hydrogen atom or a group selected from:

C$_1$-C$_6$-alkyl, C$_3$-C$_6$-cycloalkyl, (C$_1$-C$_2$-alkoxy)-(C$_2$-C$_3$-alkyl)-, and phenyl, wherein said C$_1$-C$_6$-alkyl group is optionally substituted, identically or differently, with a phenyl substituent, which phenyl substituent is optionally substituted, one, two, or three times, identically or differently, with a halogen atom or a group selected from:

C$_1$-C$_3$-alkyl, C$_1$-C$_3$-haloalkyl, and C$_1$-C$_3$-alkoxy, and wherein said phenyl group is optionally substituted, one, two, or three times, identically or differently, with a halogen atom or a group selected from:

C$_1$-C$_3$-alkyl, C$_1$-C$_3$-haloalkyl, and C$_1$-C$_3$-alkoxy,

R$^5$ represents a group selected from:

C$_1$-C$_6$-alkyl, C$_3$-C$_6$-cycloalkyl, (C$_1$-C$_2$-alkoxy)-(C$_2$-C$_3$-alkyl)-, and phenyl, wherein said C$_1$-C$_6$-alkyl group is optionally substituted, identically or differently, with a phenyl substituent, which phenyl substituent is optionally substituted, one, two, or three times, identically or differently, with a halogen atom or a group selected from:

C$_1$-C$_3$-alkyl, C$_1$-C$_3$-haloalkyl, and C$_1$-C$_3$-alkoxy, and wherein said phenyl group is optionally substituted, one, two or three times, identically or differently, with a halogen atom or a group selected from:

C$_1$-C$_3$-alkyl, C$_1$-C$_3$-haloalkyl, and C$_1$-C$_3$-alkoxy, and

X represents a group C(=O)OH or C(=O)O$^-$, or a stereoisomer, a tautomer or a salt thereof, or a mixture of same, and one, two or three ions of a paramagnetic metal M.

In accordance with an eighth embodiment of the first aspect, the present disclosure covers a liquid pharmaceutical formulation, supra, comprising a DO3A-derived tetra-chelate of general formula (I), supra, characterized in that the DO3A-derived tetra-chelate of general formula (I) is a complex between a DO3A-derived tetra-ligand of general formula (II):

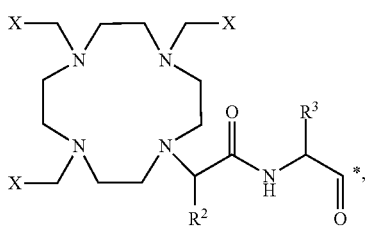
(II)

in which
R$^{1'}$ represents a group selected from:

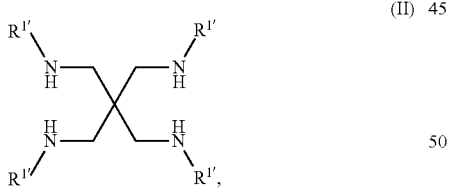

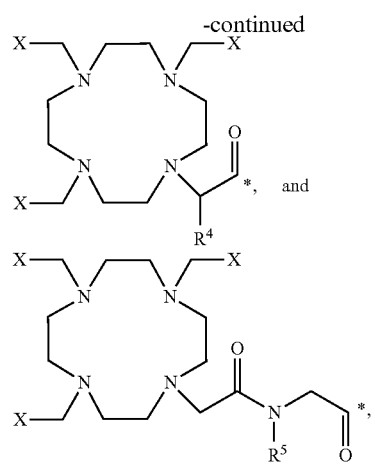

in which group * indicates the point of attachment of said group with the rest of the molecule, R$^2$, R$^3$, and R$^4$ independently of each other represents a hydrogen atom or a group selected from:

C$_1$-C$_6$-alkyl, C$_3$-C$_6$-cycloalkyl, (C$_1$-C$_2$-alkoxy)-(C$_2$-C$_3$-alkyl)-, and phenyl, wherein said C$_1$-C$_6$-alkyl group is optionally substituted, identically or differently, with a phenyl substituent, which phenyl substituent is optionally substituted, one, two, or three times, identically or differently, with a halogen atom or a group selected from:

C$_1$-C$_3$-alkyl, C$_1$-C$_3$-haloalkyl, and C$_1$-C$_3$-alkoxy, and wherein said phenyl group is optionally substituted, one, two, or three times, identically or differently, with a halogen atom or a group selected from:

C$_1$-C$_3$-alkyl, C$_1$-C$_3$-haloalkyl, and C$_1$-C$_3$-alkoxy,

R$^5$ represents a group selected from:

C$_1$-C$_6$-alkyl, C$_3$-C$_6$-cycloalkyl, (C$_1$-C$_2$-alkoxy)-(C$_2$-C$_3$-alkyl)-, and phenyl, wherein said C$_1$-C$_6$-alkyl group is optionally substituted, identically or differently, with a phenyl substituent, which phenyl substituent is optionally substituted, one, two, or three times, identically or differently, with a halogen atom or a group selected from:

C$_1$-C$_3$-alkyl, C$_1$-C$_3$-haloalkyl, and C$_1$-C$_3$-alkoxy, and wherein said phenyl group is optionally substituted, one, two or three times, identically or differently, with a halogen atom or a group selected from:

C$_1$-C$_3$-alkyl, C$_1$-C$_3$-haloalkyl, and C$_1$-C$_3$-alkoxy, and

X represents a group C(=O)OH or C(=O)O$^-$, or a stereoisomer, a tautomer or a salt thereof, or a mixture of same, and one, two or three Gd$^{3+}$ ions.

In accordance with a ninth embodiment of the first aspect, the present disclosure covers a liquid pharmaceutical formulation, supra, comprising a DO3A-derived tetra-chelate of formula (I), supra, characterized in that the DO3A-derived tetra-chelate of formula (I) is selected from the complex between a DO3A-derived tetra-ligand of formula (II-a), (II-b), or (II-c) having structures as follows:

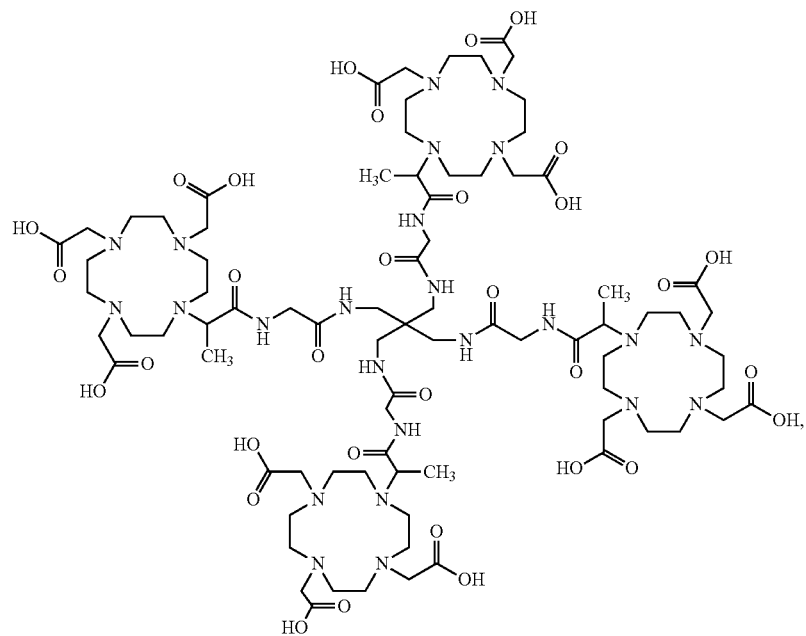
(II-a)
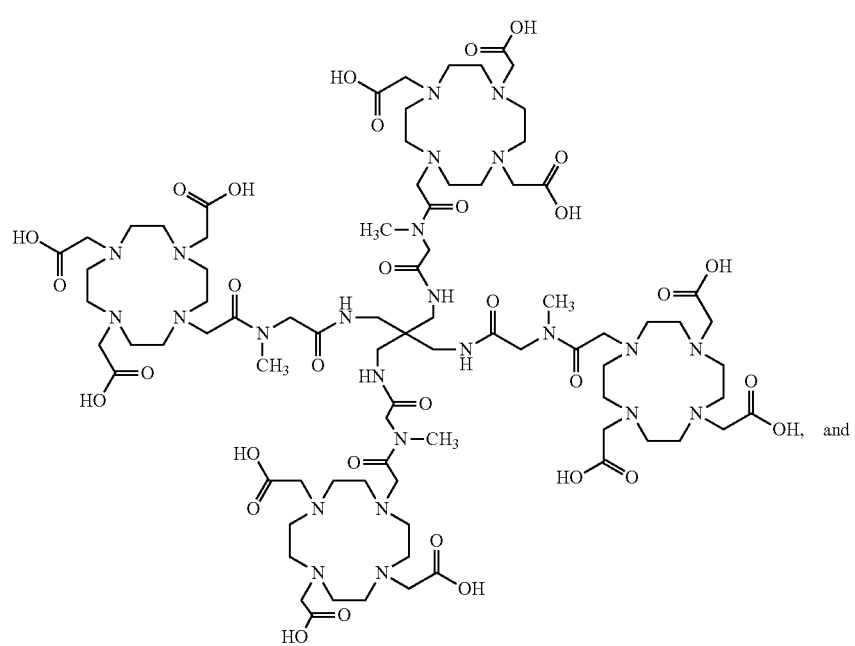
(II-b)
and

-continued (II-c)

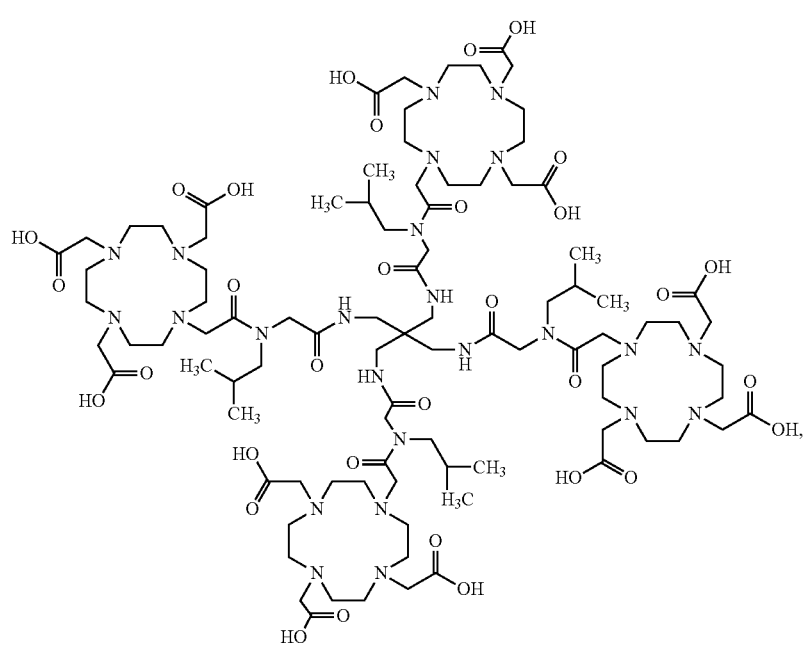

or a stereoisomer, a tautomer or a salt thereof, or a mixture of same,
and ions of a paramagnetic metal M.

The paramagnetic metal ion M is chosen from the ions of a paramagnetic metal having an atomic number of 24-29, or 59-70, i.e., chromium (Cr), manganese (Mn), iron (Fe), cobalt (Co), nickel (Ni) or copper (Cu) ions or praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm) or ytterbium (Yb) ions. The present listing of metals is intended to include all common oxidation states of the metal ion which exhibit paramagnetism, for example, if the metal is iron, ferrous ($Fe^{2+}$) and ferric ($Fe^{3+}$) ions would be included within the scope. The paramagnetic metal ion M is particularly chosen from manganese, iron, and lanthanide ions, more particularly chosen from the ions $Mn^{2+}$, $Fe^{3+}$, and $Gd^{3+}$ and even more particularly the paramagnetic metal ion M is $Gd^{3+}$.

In accordance with an tenth embodiment of the first aspect, the present disclosure covers a liquid pharmaceutical formulation, supra, comprising a DO3A-derived tetra-chelate of general formula (I), supra, in which the paramagnetic metal ion M is chosen from the ions of a paramagnetic metal having an atomic number of 24-29 or 59-70.

In accordance with a eleventh embodiment of the first aspect, the present disclosure covers a liquid pharmaceutical formulation, supra, comprising a DO3A-derived tetra-chelate of general formula (I), supra, in which the paramagnetic metal ion M is chosen from a lanthanide metal ion.

In accordance with a twelth embodiment of the first aspect, the present disclosure covers a liquid pharmaceutical formulation, supra, comprising a DO3A-derived tetra-chelate of general formula (I), supra, in which the paramagnetic metal ion M is chosen from the ions $Mn^{2+}$, $Fe^{3+}$, and $Gd^{3+}$ and even more particularly the paramagnetic metal ion M is a $Gd^{3+}$ ion.

The liquid pharmaceutical formulation of the present disclosure may comprise besides the DO3A-derived tetra chelate of general formula (I), supra, the corresponding $M_3$-DO3A-derived chelate, the corresponding $M_2$-DO3A-derived chelate, the corresponding M-DO3A-derived chelate and the corresponding DO3A-derived tetra-ligand of general formula (II), and stereoisomers, tautomers, or salts thereof, or mixtures thereof.

The liquid pharmaceutical formulation of the present disclosure may comprise besides the DO3A-derived tetra chelate of general formula (I), supra, one or more of the corresponding $M_3$-DO3A-derived chelate, the corresponding $M_2$-DO3A-derived chelate, the corresponding M-DO3A-derived chelate and the corresponding DO3A-derived tetra-ligand of general formula (II), and stereoisomers, tautomers, or salts thereof, or mixtures thereof.

In accordance with an thirteenth embodiment of the first aspect, the present disclosure covers a liquid pharmaceutical formulation, supra, comprising a DO3A-derived tetra-chelate of general formula (I), supra, the corresponding $M_3$-DO3A-derived chelate, the corresponding $M_2$-DO3A-derived chelate, the corresponding M-DO3A-derived chelate and the corresponding DO3A-derived tetra-ligand of general formula (II), and stereoisomers, tautomers, or salts thereof, or mixtures thereof.

In accordance with a fourteenth embodiment of the first aspect, the present disclosure covers a liquid pharmaceutical formulation, supra, comprising a $Gd_4$-DO3A-derived tetra-chelate of general formula (I), supra, the corresponding $Gd_3$-DO3A-derived chelate, the corresponding $Gd_2$-DO3A-derived chelate, the corresponding Gd-DO3A-derived chelate and the corresponding DO3A-derived tetra-ligand of general formula (II), and stereoisomers, tautomers, or salts thereof, or mixtures thereof.

In accordance with a fifteenth embodiment of the first aspect, the present disclosure covers a liquid pharmaceutical formulation, supra, comprising a DO3A-derived tetra-chelate of general formula (I), supra, one or more of the corresponding $M_3$-DO3A-derived chelate, the corresponding $M_2$-DO3A-derived chelate, the corresponding M-DO3A-derived chelate and the corresponding DO3A- derived tetra-ligand of general formula (II), and stereoisomers, tautomers, or salts thereof, or mixtures thereof.

In accordance with a sixteenth embodiment of the first aspect, the present disclosure covers a liquid pharmaceutical formulation, supra, comprising a $Gd_4$-DO3A-derived tetra-chelate of general formula (I), supra, one or more of the corresponding $Gd_3$-DO3A-derived chelate, the corresponding $Gd_2$-DO3A-derived chelate, the corresponding Gd-DO3A-derived chelate and the corresponding DO3A-derived tetra-ligand of general formula (II), and stereoisomers, tautomers, or salts thereof, or mixtures thereof.

DO3A-derived tetra-chelates with sub-stoichiometric amounts of paramagnetic metal ions are compositions containing DO3A-derived tetra-chelates and further including chelates between a DO3A-derived tetra-ligand of general formula (II) and sub-stoichiometric amounts of paramagnetic metal ions, such as one, two or three paramagnetic metal ions, and/or containing the DO3A-derived tetra-ligand of general formula (II), or mixtures thereof. In various embodiments, the DO3A-derived tetra-ligand comprising sub-stoichiometric amounts of paramagnetic metal ions may include sub-stoichiometric amounts of one or more weak binding metal ions. As used herein, the term "weak binding metal ions" include metal ions for the alkali metals, alkaline earth metals, and transition metals that have a binding affinity for the DO3A-derived tetra-chelate that is less than the binding affinity of the DO3A-derived tetra-chelate and the lanthanide metal ion. In various embodiments, the weak binding metal ions may include lithium, calcium, sodium, zinc, potassium, or magnesium ions. According to various embodiments, the DO3A-derived tetra-chelates with sub-stoichiometric amounts of paramagnetic metal ions may contain 3.95 to 3.9996 mole of paramagnetic metal ion relative to 1.000 mole of DO3A-derived tetra-ligand of general formula (II). This results in a paramagnetic metal scavenging capacity of 0.01 to 1.25% mol/mol (relative to the total concentration of the paramagnetic metal).

Without intending to be bound by any theory, it is believed that sub-stoichiometric chelates, having sub-stoichiometric amounts of paramagnetic metal ions which are contained in the DO3A-derived tetra-chelates, may act as scavengers that will bind to any paramagnetic metal ion that may be decomplexed or released from the DO3A-derived tetra-chelate by binding to the released paramagnetic metal ion in a transmetallation exchange reaction with the weak binding metal ion in the ligating site or by binding the paramagnetic metal ion in the metal-free ligating site, thereby removing the free paramagnetic metal ion from solution. According to various embodiments, the pharmaceutical formulation comprising DO3A-derived tetra-chelates and DO3A-derived tetra-ligands with sub-stoichiometric amounts of paramagnetic metal ions may have concentrations of the DO3A-derived tetra-ligands with sub-stoichiometric amounts of paramagnetic metal ions in the range of 0.01% to 1.25% mol/mol (inclusive), for example in the range of 0.02% to 1% mol/mol (inclusive), more particularly in the range of 0.025% to 0.5% mol/mol (inclusive), this proportion being related to the total concentration of the paramagnetic metal ion in the formulation.

In specific embodiments, the DO3A-derived tetra-chelates with sub-stoichiometric amounts of paramagnetic metal ions may include sub-stoichiometric paramagnetic gadolinium ion ($Gd^{3+}$), such as $Gd_4$-DO3A-derived tetra-chelates with sub-stoichiometric amounts of paramagnetic gadolinium ions. According to these embodiments, the pharmaceutical formulation comprising $Gd_4$-DO3A-derived tetra-chelates further comprise chelates between a DO3A-derived tetra-ligand of general formula (II) and one, two or three $Gd^{3+}$ ions, and/or containing the DO3A-derived tetra-ligand of general formula (II) as a free ligand, or mixtures thereof. In various embodiments, the $Gd_4$-DO3A-derived tetra-ligand comprising sub-stoichiometric amounts of paramagnetic gadolinium ions and/or the free DO3A-derived tetra-ligand may include sub-stoichiometric or stoichiometric amounts, respectively, of one or more weak binding metal ions bound in the gadolinium-free ligating sites.

More specifically a sub-stoichiometric chelate between the DO3A-derived tetra-ligand of formula (II-a),

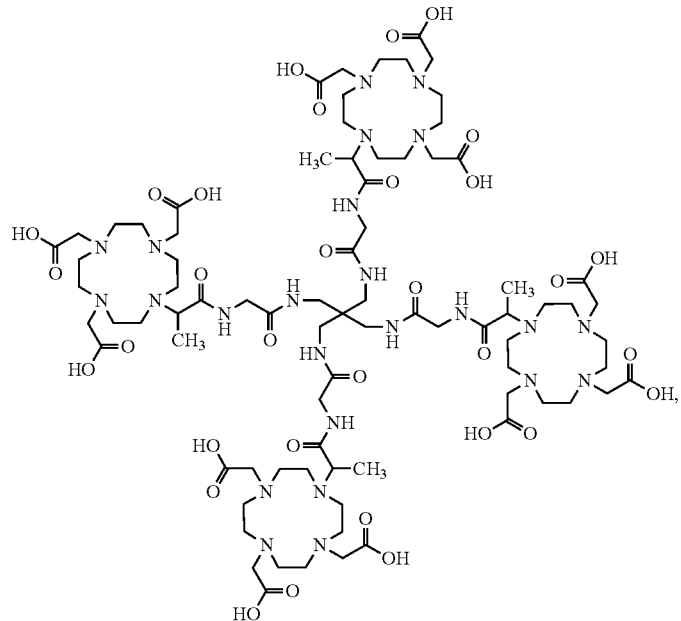

(II-a)

and three Gd³⁺ ions is the Gd₃-DO3A-derived chelate of formula (Gd₃-II-a),

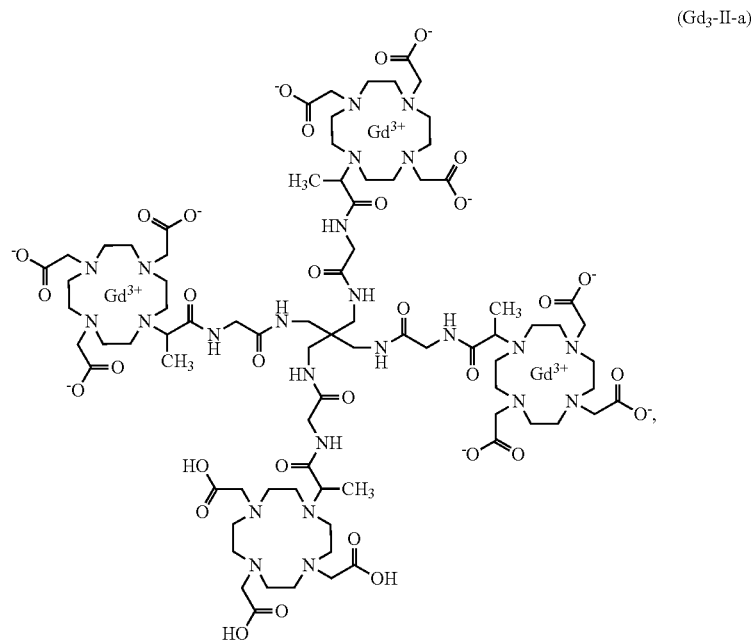

(Gd₃-II-a)

a sub-stoichiometric chelate between the DO3A-derived tetra-ligand of formula (II-a) and two Gd³⁺ ions is the Gd₂-DO3A-derived chelate of formula (Gd₂-II-a),

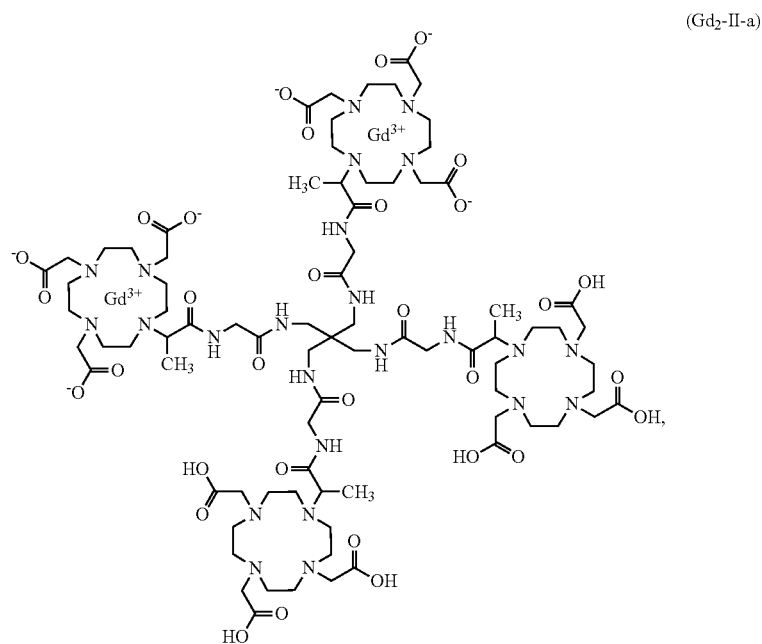

(Gd₂-II-a)

and a sub-stoichiometric chelate between the DO3A-derived tetra-ligand of formula (II-a) and one Gd³⁺ ion is the Gd-DO3A-derived chelate of formula (Gd-II-a),

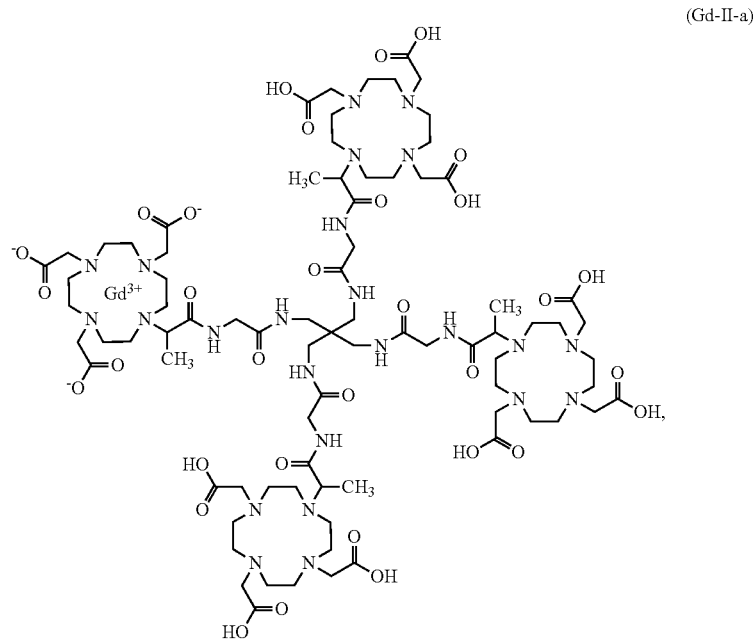
(Gd-II-a)

In specific embodiments, the DO3A-derived tetra-chelates with sub-stoichiometric amounts of gadolinium ions ($Gd^{3+}$) are $Gd_3$-DO3A-derived chelate of formula ($Gd_3$-II-a), $Gd_2$-DO3A-derived chelate of formula ($Gd_2$-II-a), Gd-DO3A-derived chelate of formula (Gd-II-a), or DO3A-derived tetra-ligand of formula (II-a), or mixtures thereof.

More specifically a sub-stoichiometric chelate between the DO3A-derived tetra-ligand of formula (II-b),

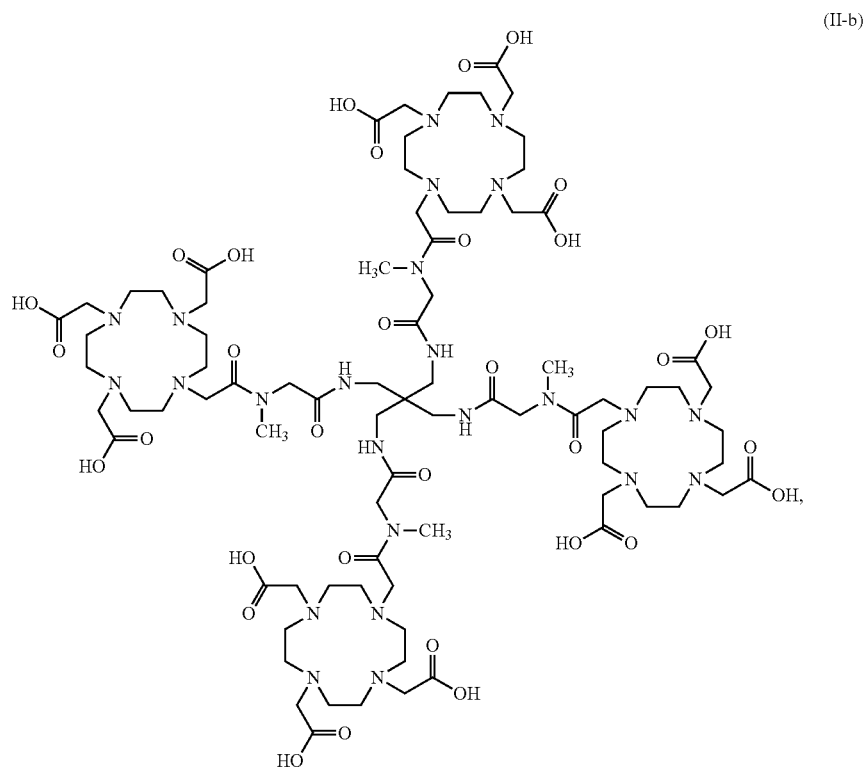 [SMILES: CN(CC(=O)NCC(CNC(=O)CN(C)C(=O)CN1CCN(CC(=O)O)CCN(CC(=O)O)CCN(CC(=O)O)CC1)(CNC(=O)CN(C)C(=O)CN1CCN(CC(=O)O)CCN(CC(=O)O)CCN(CC(=O)O)CC1)CNC(=O)CN(C)C(=O)CN1CCN(CC(=O)O)CCN(CC(=O)O)CCN(CC(=O)O)CC1)C(=O)CN1CCN(CC(=O)O)CCN(CC(=O)O)CCN(CC(=O)O)CC1]
(II-b)

and three $Gd^{3+}$ ions is the $Gd_3$-DO3A-derived chelate of formula ($Gd_3$-II-b), (Gd₃-II-b)
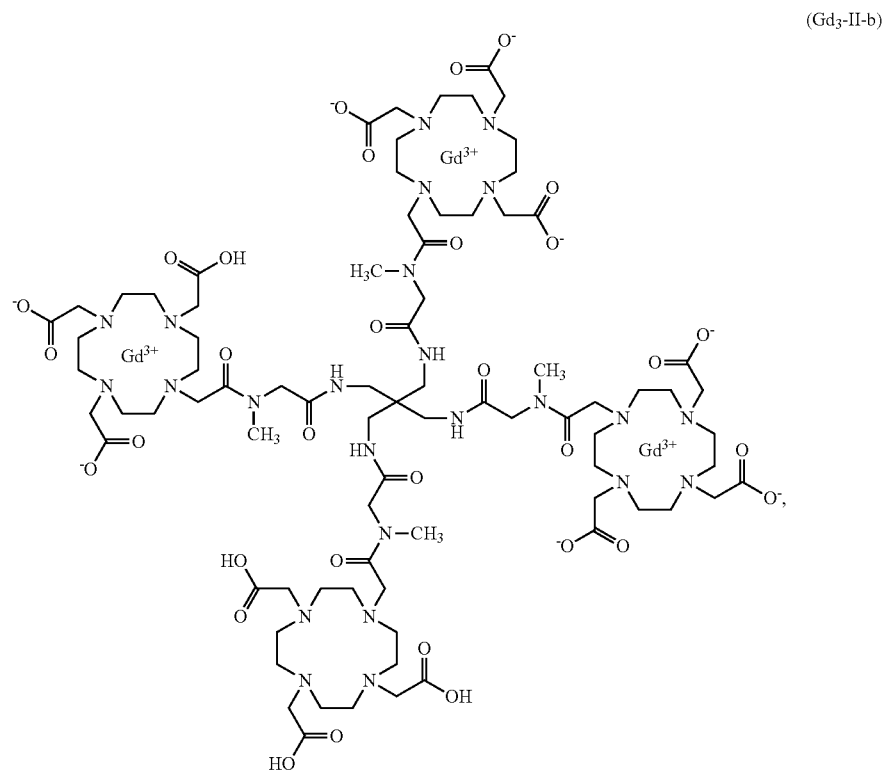
a sub-stoichiometric chelate between the DO3A-derived tetra-ligand of formula (II-b) and two Gd³⁺ ions is the Gd₂-DO3A-derived chelate of formula (Gd₂-II-b),
(Gd₂-II-b)
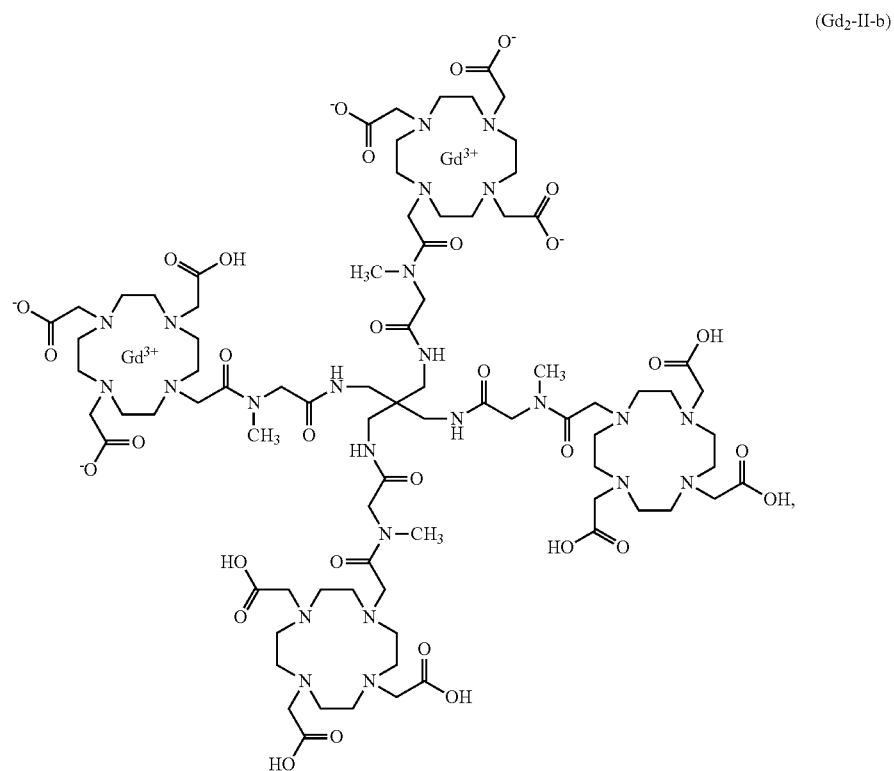

and a sub-stoichiometric chelate between the DO3A-derived tetra-ligand of formula (II-b) and one Gd³⁺ ion is the Gd-DO3A-derived chelate of formula (Gd-II-b),

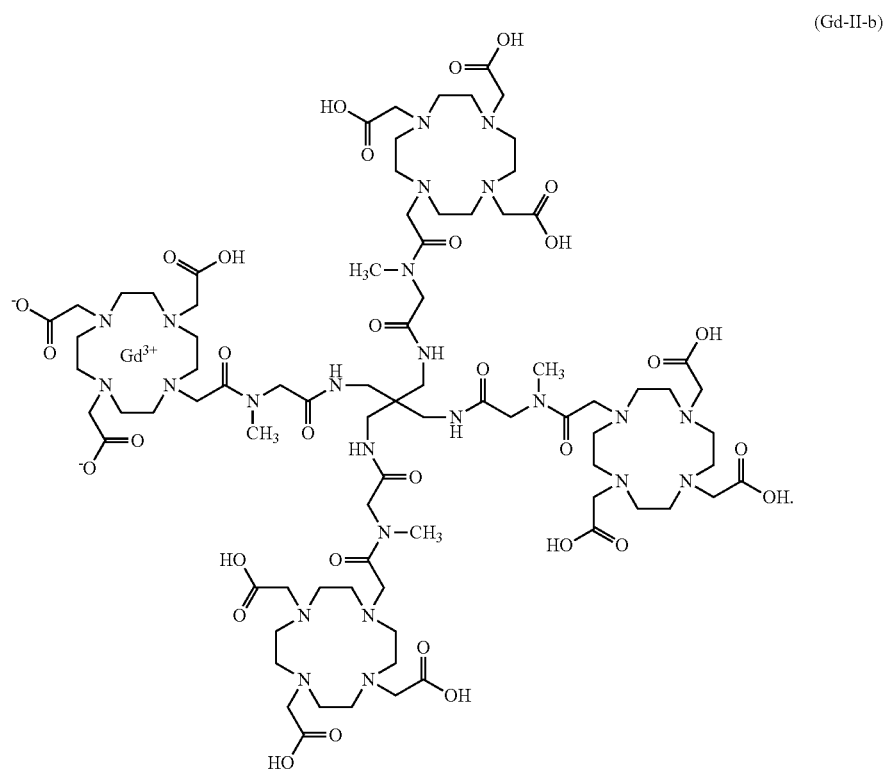

(Gd-II-b)

In specific embodiments, the DO3A-derived tetra-chelates with sub-stoichiometric amounts of gadolinium ions (Gd³⁺) are Gd₃-DO3A-derived chelate of formula (Gd₃-II-b), Gd₂-DO3A-derived chelate of formula (Gd₂-II-b), Gd-DO3A-derived chelate of formula (Gd-II-b), or DO3A-derived tetra-ligand of formula (II-b), or mixtures thereof.

More specifically a sub-stoichiometric chelate between the DO3A-derived tetra-ligand of formula (II-c),

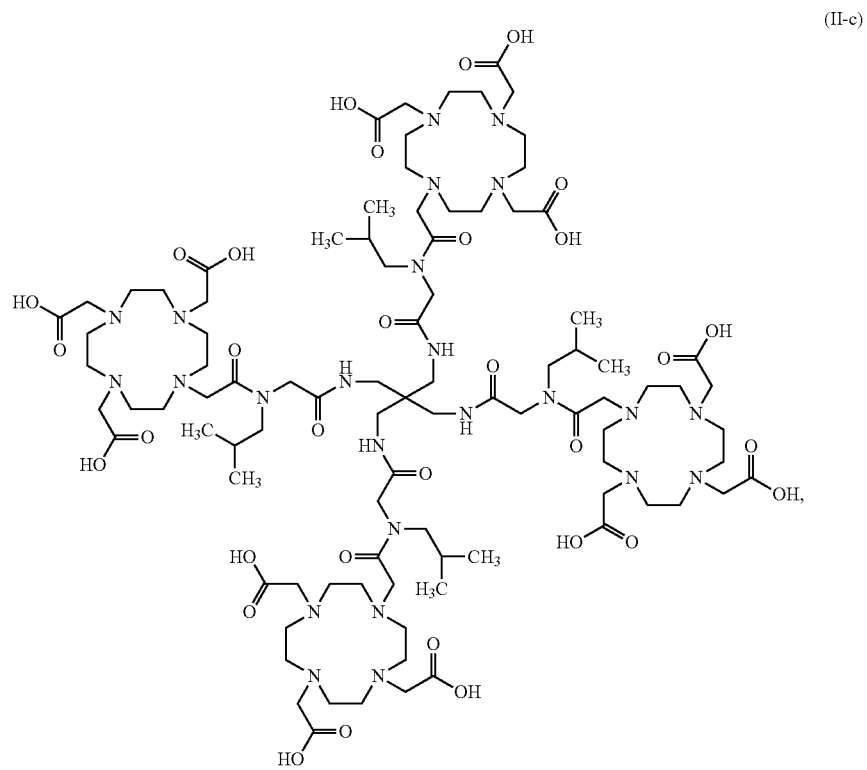 [SMILES: CC(C)CN(CC(=O)NCC(CNC(=O)CN(CC(C)C)C(=O)CN1CCN(CC(=O)O)CCN(CC(=O)O)CCN(CC(=O)O)CC1)(CNC(=O)CN(CC(C)C)C(=O)CN1CCN(CC(=O)O)CCN(CC(=O)O)CCN(CC(=O)O)CC1)CNC(=O)CN(CC(C)C)C(=O)CN1CCN(CC(=O)O)CCN(CC(=O)O)CCN(CC(=O)O)CC1)C(=O)CN1CCN(CC(=O)O)CCN(CC(=O)O)CCN(CC(=O)O)CC1]
(II-c)
and three Gd³⁺ ions is the Gd₃-DO3A-derived chelate of formula (Gd₃-II-c),
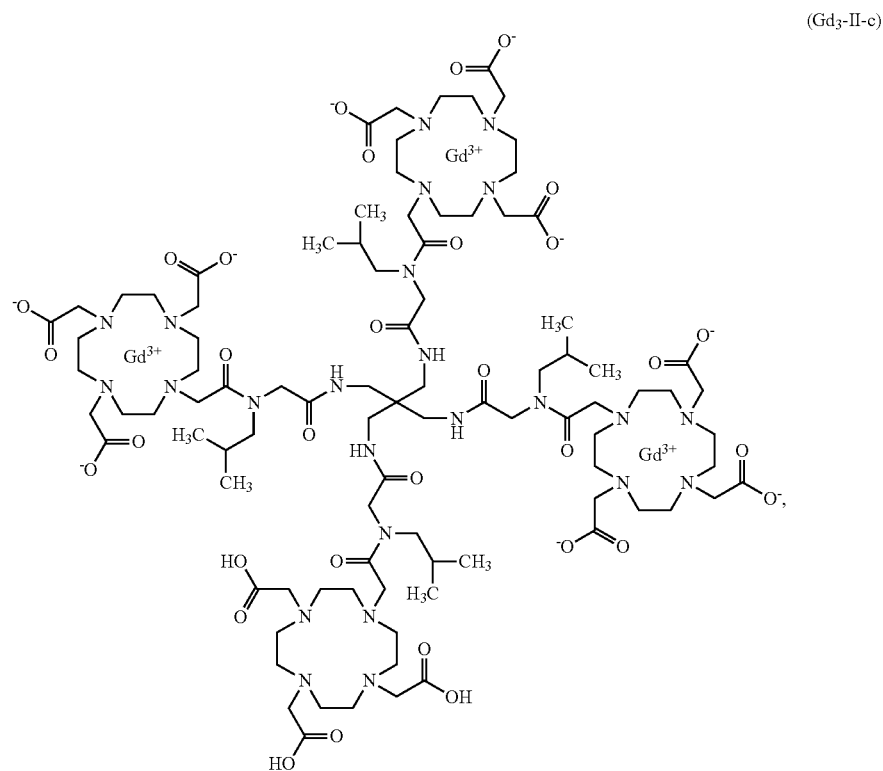
(Gd₃-II-c)

a sub-stoichiometric chelate between the DO3A-derived tetra-ligand of formula (II-c) and two $Gd^{3+}$ ions is the $Gd_2$-DO3A-derived chelate of formula ($Gd_2$-II-c),
($Gd_2$-II-c)
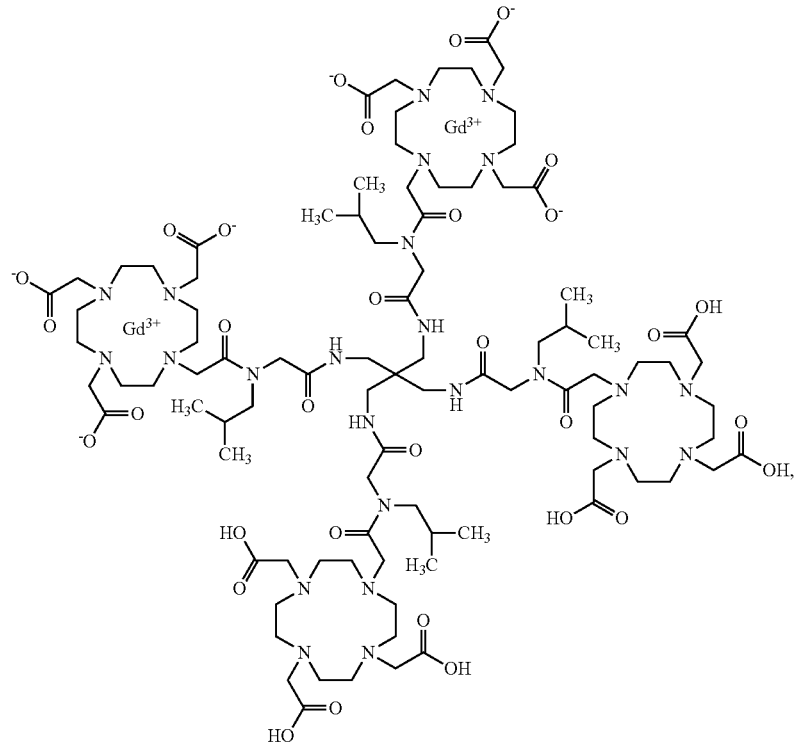
and a sub-stoichiometric chelate between the DO3A-derived tetra-ligand of formula (II-c) and one $Gd^{3+}$ ion is the Gd-DO3A-derived chelate of formula (Gd-II-c),
(Gd-II-c)
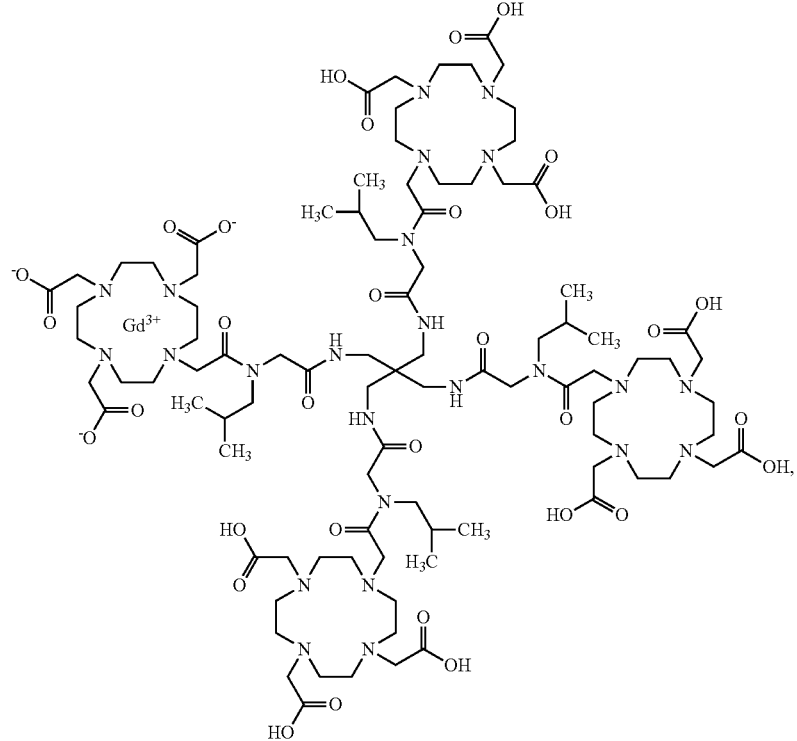

In specific embodiments, the DO3A-derived tetra-chelates with sub-stoichiometric amounts of gadolinium ions ($Gd^{3+}$) are $Gd_3$-DO3A-derived chelate of formula ($Gd_3$-II-c), $Gd_2$-DO3A-derived chelate of formula ($Gd_2$-II-c), Gd-DO3A-derived chelate of formula (Gd-II-c), or DO3A-derived tetra-ligand of formula (II-c), or mixtures thereof.

The formulation according to the present disclosure exhibits stability over time such that the concentration of free paramagnetic metal ions remains essentially zero (below the detection limit of sensitive analytical methods). In various embodiments, the concentration of free paramagnetic metal ions M remains less than or equal to 2 ppm (m/v), i.e. in the range of 0 to 2 ppm (m/v) (inclusive), over a period of at least 6 months, at 25° C. and 40° C. Accelerated storage condition (6 months at 40° C.) is considered to be an adequate condition for accelerated stress conditions for pharmaceutical contrast formulations.

In accordance with a seventeenth embodiment of the first aspect, the present disclosure covers a liquid pharmaceutical formulation, supra, characterized in that it has a concentration of a free paramagnetic metal ion M of less than or equal to 5 ppm (m/v), i.e. in a range of 0 to 5 ppm (m/v) (inclusive), particularly less than or equal to 2 ppm (m/v), i.e. in a range of 0 to 2 ppm (m/v) (inclusive), and more particularly less than or equal to 0.5 ppm (m/v), i.e. in a range of 0 to 0.5 ppm (m/v) (inclusive).

In accordance with a eighteenth embodiment of the first aspect, the present disclosure covers a liquid pharmaceutical formulation, supra, characterized in that it comprises at least one compound capable of forming a chelate with a free paramagnetic metal ion M contained in the composition of Formula (I). Such compounds, also called "metal scavenging compounds" are described in detail herein. According to various embodiments, the compound capable of forming a chelate with a free paramagnetic metal ion M may have a concentration in the formulation in a range of 0.002% to 5% mol/mol (inclusive), particularly in a range of 0.01% to 1% mol/mol (inclusive), more particularly in a range of 0.05% to 0.5% mol/mol (inclusive), measured as a proportion relative to the total paramagnetic metal ion, such as $Gd^{3+}$ concentration in the formulation.

In accordance with a nineteenth embodiment of the first aspect, the present disclosure covers a liquid pharmaceutical formulation, supra, characterized in that it comprises one or more compounds capable of forming a complex with the free paramagnetic metal ion M, which compounds may be selected from Ca-BT-DO3A (Calcobutrol), Ca-DOTA, Ca-HP-DO3A and Ca-DTPA or from the respective free chelating ligands, or salts thereof with alkaline metals, alkaline earth metals, weak binding transition metals, or organic bases.

In accordance with a twentieth embodiment of the first aspect, the present disclosure covers a liquid pharmaceutical formulation, supra, characterized in that it comprises a compound capable of forming a complex with the free paramagnetic metal ion M, which compound is Ca-BT-DO3A (Calcobutrol).

In accordance with a twenty-first embodiment of the first aspect, the present disclosure covers a liquid pharmaceutical formulation, supra, characterized in that it comprises a compound capable of forming a chelate with the free paramagnetic metal ion M, which compound is Ca-BT-DO3A (Calcobutrol), preferably in the range of 0.002% to 5% mol/mol (inclusive), measured as a proportion relative to a total paramagnetic metal ion concentration, such as $Gd^{3+}$ concentration in the formulation.

In accordance with an twenty-second embodiment of the first aspect, the proportion of Ca-BT-DO3A is in a range of 0.002% to 5% mol/mol (inclusive), for example in a range of 0.002% to 1% mol/mol (inclusive), particularly in a range of 0.01% to 1% mol/mol (inclusive), more particularly in a range of 0.05% to 0.5% mol/mol (inclusive), this proportion being related to the total paramagnetic metal ion concentration, such as $Gd^{3+}$, in said formulation.

In accordance with a twenty-third embodiment of the first aspect, the present disclosure covers a liquid pharmaceutical formulation, supra, characterized in that the formulation comprises compounds capable of forming complexes with the free paramagnetic metal ion M, which compounds are DO3A-derived tetra-chelates with sub-stoichiometric amounts of paramagnetic metal ions, as defined supra, or salts thereof with $Ca^{2+}$ ions, $Na^+$ ions, $Zn^{2+}$ ions, $Mg^{2+}$ ions, and/or meglumine ions.

In accordance with a twenty-fourth embodiment of the first aspect, the present disclosure covers a liquid pharmaceutical formulation, supra, characterized in that the formulation comprises compounds capable of forming complexes with the free paramagnetic metal ion M, which compounds are DO3A-derived tetra-chelates with sub-stoichiometric amounts of $Gd^{3+}$ ions, as defined supra, or salts thereof with $Ca^{2+}$ ions, $Na^+$ ions, $Zn^{2+}$ ions, $Mg^{2+}$ ions and/or meglumine ions.

In accordance with a twenty-fifth embodiment of the first aspect, the proportion of DO3A-derived tetra-chelates with sub-stoichiometric amounts of $Gd^{3+}$ ions is in a range of 0.002% to 5% mol/mol (inclusive) [with reference to the total molar Gd-concentration].

In accordance with a twenty-sixth embodiment of the first aspect, the present disclosure covers a liquid pharmaceutical formulation, supra, characterized in that it comprises compounds capable of forming a chelate with the free paramagnetic metal ion M, which compounds are DO3A-derived tetra-chelates with sub-stoichiometric amounts of $Gd^{3+}$ ions, which are selected from Gd₃-DO3A-derived chelate of formula (Gd₃-II-a),
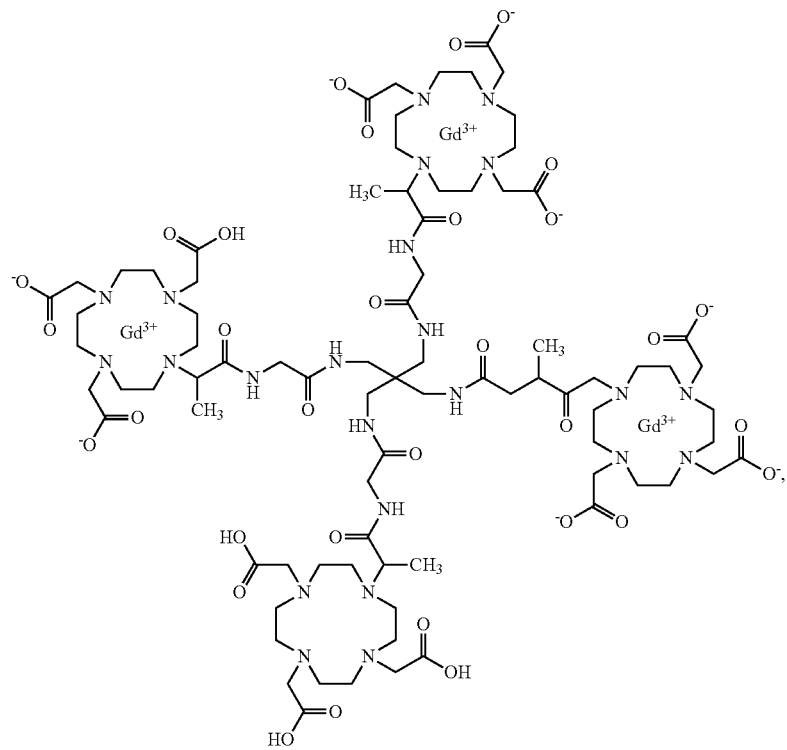
Gd₂-DO3A-derived chelate of formula (Gd₂-II-a),
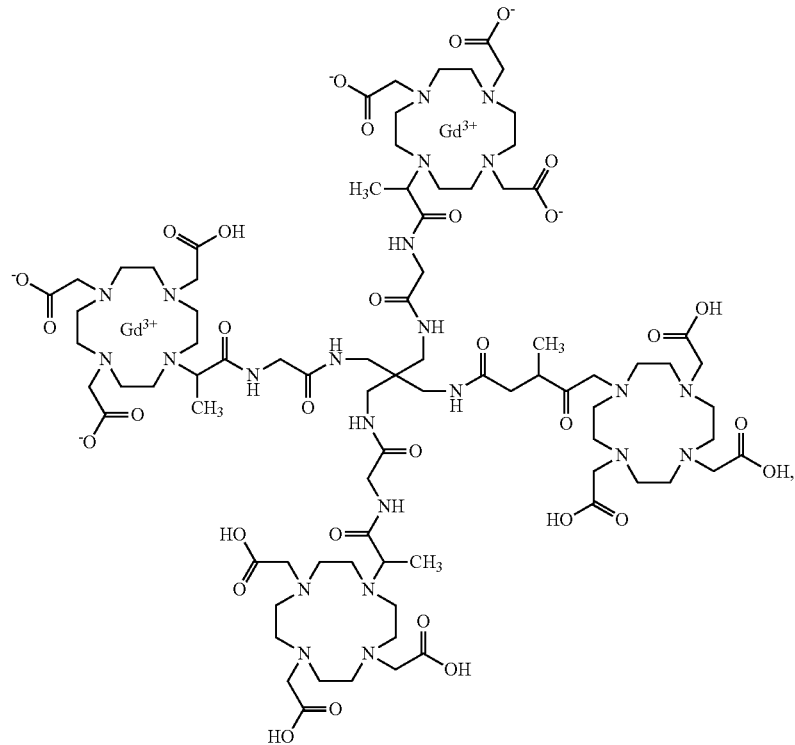

Gd-DO3A-derived chelate of formula (Gd-II-a),
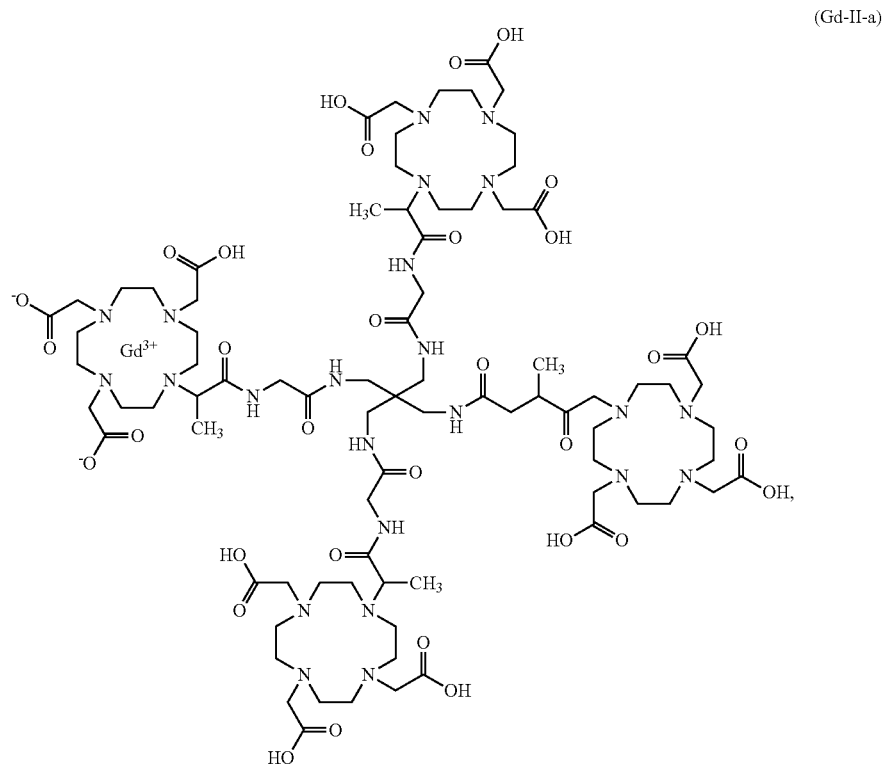
and
DO3A-derived tetra-ligand of formula (II-a),
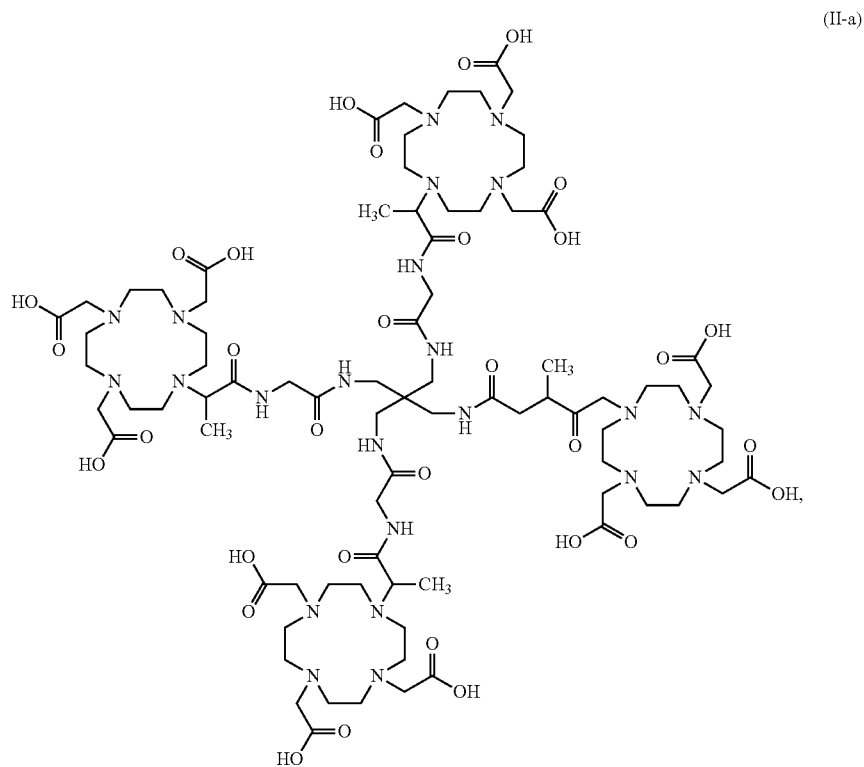 [SMILES: CC(CC(=O)NCC(CNC(=O)CNC(=O)C(C)N1CCN(CC(=O)O)CCN(CC(=O)O)CCN(CC(=O)O)CC1)(CNC(=O)CNC(=O)C(C)N1CCN(CC(=O)O)CCN(CC(=O)O)CCN(CC(=O)O)CC1)CNC(=O)CNC(=O)C(C)N1CCN(CC(=O)O)CCN(CC(=O)O)CCN(CC(=O)O)CC1)C(=O)CN1CCN(CC(=O)O)CCN(CC(=O)O)CCN(CC(=O)O)CC1]

or stereoisomers, tautomers or salts thereof, or mixtures of same, preferably in the range of 0.01 to 1.25 mol % [with reference to the total molar Gd-concentration].

In accordance with a twenty-seventh embodiment of the first aspect, the present disclosure covers a liquid pharmaceutical formulation, supra, characterized in that it comprises compounds capable of forming a chelate with the free paramagnetic metal ion M, which compounds are DO3A-derived tetra-chelates with sub-stoichiometric amounts of $Gd^{3+}$ ions, which are selected from $Gd_3$-DO3A-derived chelate of formula ($Gd_3$-II-b),

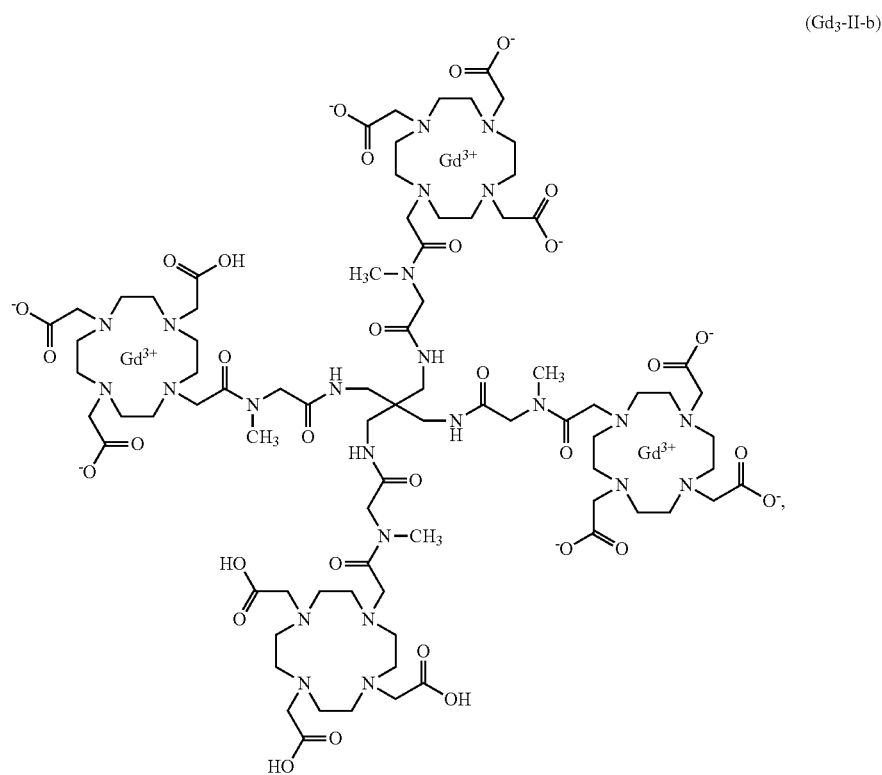

Gd$_2$-DO3A-derived chelate of formula (Gd$_2$-II-b),
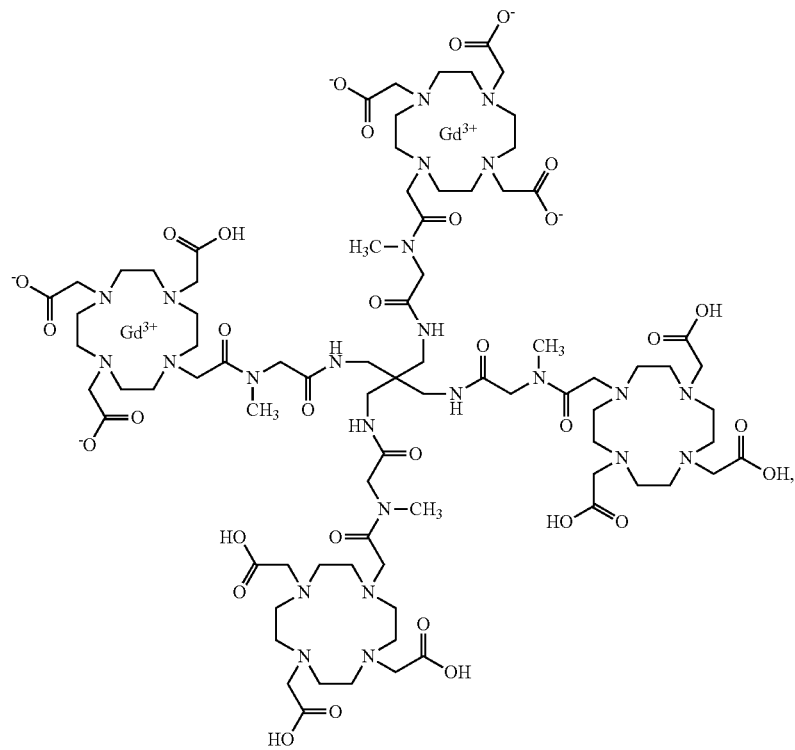
(Gd$_3$-II-b)
Gd-DO3A-derived chelate of formula (Gd-II-b),
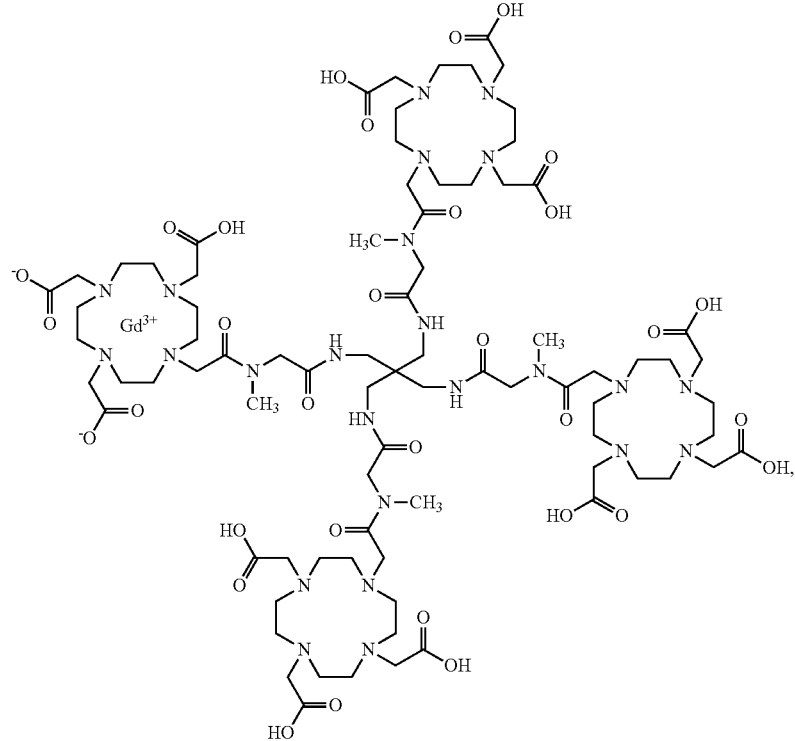
(Gd-II-b)

and
DO3A-derived tetra-ligand of formula (II-b),

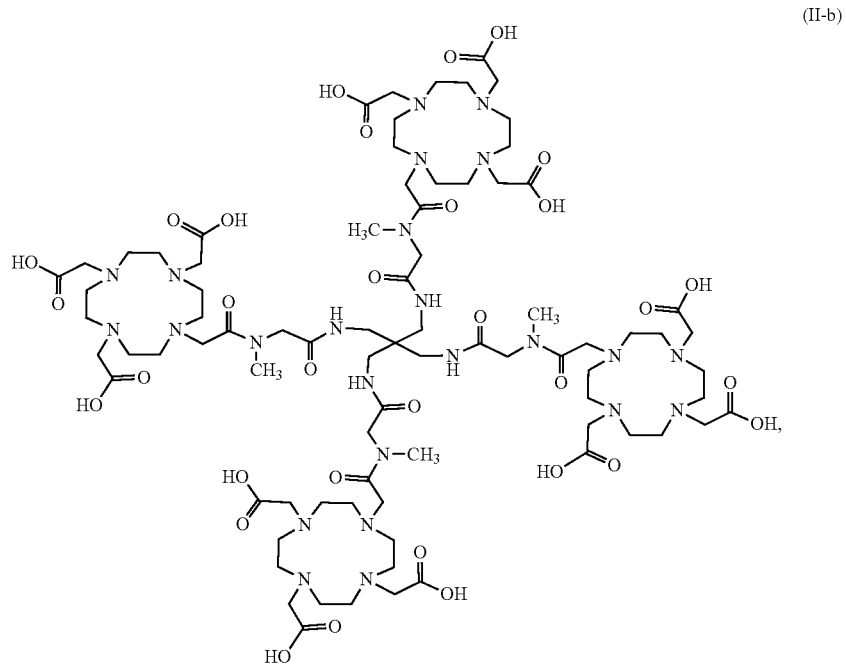 [SMILES: CN(CC(=O)NCC(CNC(=O)CN(C)C(=O)CN1CCN(CC(=O)O)CCN(CC(=O)O)CCN(CC(=O)O)CC1)(CNC(=O)CN(C)C(=O)CN1CCN(CC(=O)O)CCN(CC(=O)O)CCN(CC(=O)O)CC1)CNC(=O)CN(C)C(=O)CN1CCN(CC(=O)O)CCN(CC(=O)O)CCN(CC(=O)O)CC1)C(=O)CN1CCN(CC(=O)O)CCN(CC(=O)O)CCN(CC(=O)O)CC1]

(II-b)

or stereoisomers, tautomers or salts thereof, or mixtures of same,
preferably in the range of of 0.01 to 1.25 mol % [with reference to the total molar Gd-concentration].

In accordance with a twenty-eighth embodiment of the first aspect, the present disclosure covers a liquid pharmaceutical formulation, supra, characterized in that it comprises compounds capable of forming a chelate with the free paramagnetic metal ion M, which compounds are DO3A-derived tetra-chelates with sub-stoichiometric amounts of $Gd^{3+}$ ions, which are selected from
$Gd_3$-DO3A-derived chelate of formula ($Gd_3$-II-c),

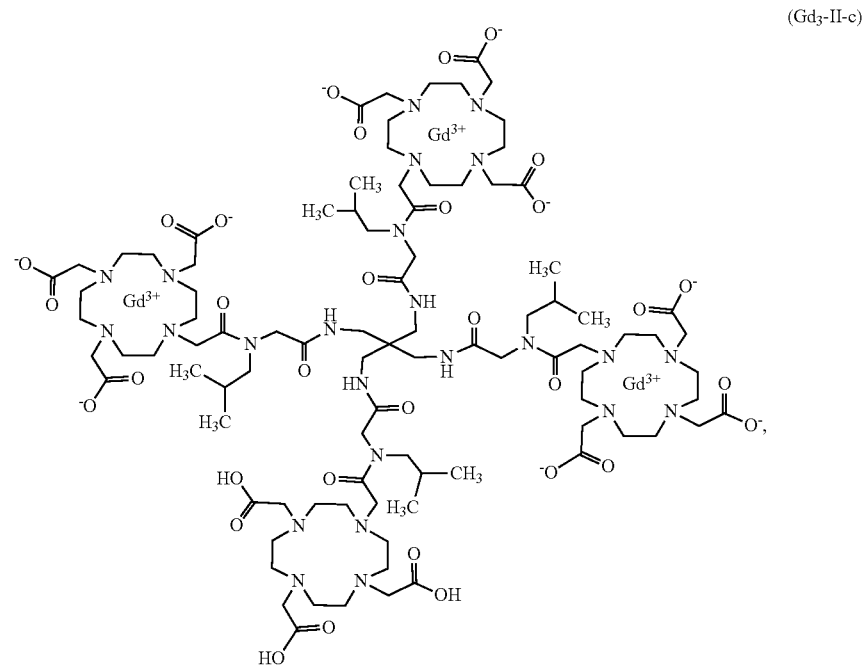

($Gd_3$-II-c)

Gd$_2$-DO3A-derived chelate of formula (Gd$_2$-II-c),
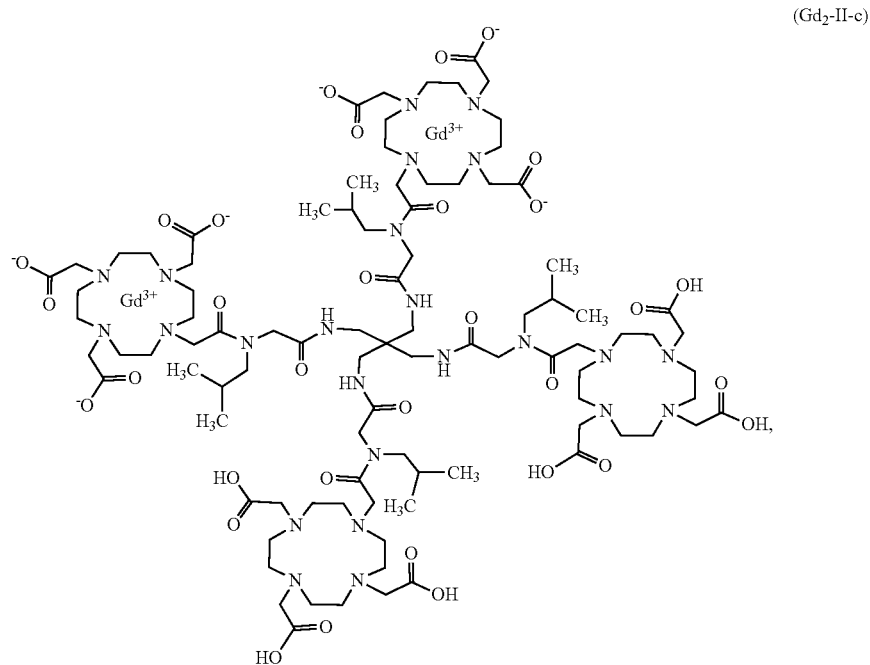
(Gd$_2$-II-c)
Gd-DO3A-derived chelate of formula (Gd-II-c),
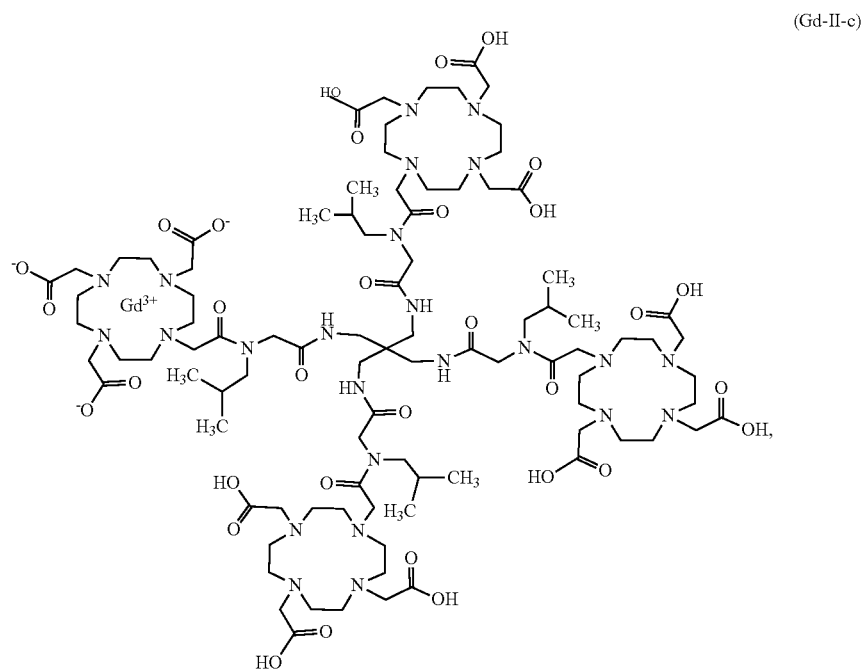
(Gd-II-c)

and
DO3A-derived tetra-ligand of formula (II-c),

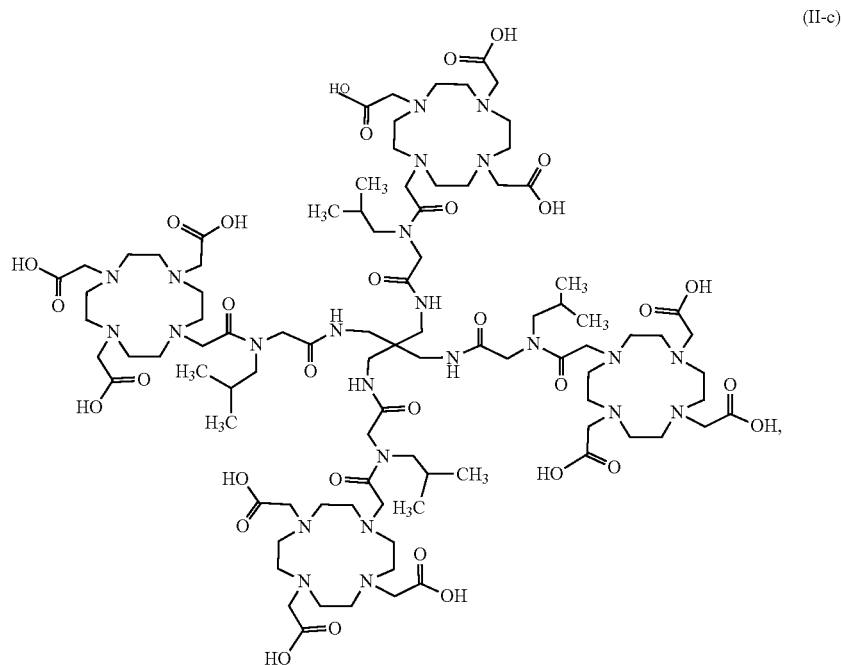 [SMILES: CC(C)CN(CC(=O)NCC(CNC(=O)CN(CC(C)C)C(=O)CN1CCN(CC(=O)O)CCN(CC(=O)O)CCN(CC(=O)O)CC1)(CNC(=O)CN(CC(C)C)C(=O)CN1CCN(CC(=O)O)CCN(CC(=O)O)CCN(CC(=O)O)CC1)CNC(=O)CN(CC(C)C)C(=O)CN1CCN(CC(=O)O)CCN(CC(=O)O)CCN(CC(=O)O)CC1)C(=O)CN1CCN(CC(=O)O)CCN(CC(=O)O)CCN(CC(=O)O)CC1]

(II-c)

or stereoisomers, tautomers or salts thereof, or mixtures of same, preferably in the range of 0.01 to 1.25 mol % [with reference to the total molar Gd-concentration].

In accordance with a twenty-ninth embodiment of the first aspect, the present disclosure covers a liquid pharmaceutical formulation comprising a DO3A-derived tetra-chelate of general formula (I):

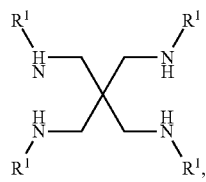

(I)

in which
$R^1$ represents a group selected from:

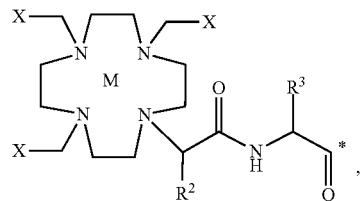

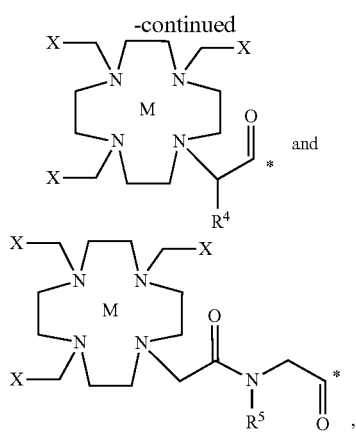

-continued in which group * indicates the point of attachment of said group with the rest of the molecule, $R^2$, $R^3$, and $R^4$ independently of each other represents a hydrogen atom or a group selected from:

$C_1$-$C_6$-alkyl, $C_3$-$C_6$-cycloalkyl, ($C_1$-$C_2$-alkoxy)-($C_2$-$C_3$-alkyl)-, and phenyl, wherein said $C_1$-$C_6$-alkyl group is optionally substituted, identically or differently, with a phenyl substituent, which phenyl substituent is optionally substituted, one, two, or three times, identically or differently, with a halogen atom or a group selected from:

$C_1$-$C_3$-alkyl, $C_1$-$C_3$-haloalkyl, and $C_1$-$C_3$-alkoxy, and wherein said phenyl group is optionally substituted, one, two, or three times, identically or differently, with a halogen atom or a group selected from:

$C_1$-$C_3$-alkyl, $C_1$-$C_3$-haloalkyl, and $C_1$-$C_3$-alkoxy,

R⁵ represents a group selected from:
  $C_1$-$C_6$-alkyl, $C_3$-$C_6$-cycloalkyl, ($C_1$-$C_2$-alkoxy)-($C_2$-$C_3$-alkyl)-, and phenyl,
    wherein said $C_1$-$C_6$-alkyl group is optionally substituted, identically or differently, with a phenyl substituent, which phenyl substituent is optionally substituted, one, two, or three times, identically or differently, with a halogen atom or a group selected from:
      $C_1$-$C_3$-alkyl, $C_1$-$C_3$-haloalkyl, and $C_1$-$C_3$-alkoxy, and
    wherein said phenyl group is optionally substituted, one, two, or three times, identically or differently, with a halogen atom or a group selected from:
      $C_1$-$C_3$-alkyl, $C_1$-$C_3$-haloalkyl, and $C_1$-$C_3$-alkoxy,
X represents a group C(=O)O⁻, and
M represents an ion of a paramagnetic metal,
or a stereoisomer, a tautomer, a salt thereof, or a mixture of same,
said formulation further comprising
  a sub-stoichiometric chelate, as described herein, in a concentration fraction of 0.01 to 1.25 mol % [with reference to the total molar concentration of the paramagnetic metal], wherein the sub-stoichiometric chelate is selected from one or more of $M_3$-DO3A-derived chelate, $M_2$-DO3A-derived chelate, M-DO3A-derived chelate, and the DO3A-derived tetra-ligand, or mixtures thereof or stereoisomers, tautomers, salts thereof, or a mixture of any thereof,
    wherein the one, two or three DO3A ligands of said sub-stoichiometric chelates, which are not complexed with ions of paramagnetic metals, and the four DO3A ligands of the DO3A-derived tetra-ligand, may be present as complexes or salts with $Ca^{2+}$ ions, $Na^+$ ions, $Zn^{2+}$ ions, $Mg^{2+}$ ions, or meglumine ions or as free carboxylic acids,
  a pharmaceutically acceptable solvent, and
  optionally comprising a buffer,
wherein the DO3A-derived tetra-chelate of general formula (I) has a concentration in the formulation in a range of 1 mmol paramagnetic metal ion/L to 1000 mmol paramagnetic metal ion/L (inclusive), particularly in a range of 60 to 750 mmol paramagnetic metal ion/L (inclusive), particularly in a range of 70 to 700 mmol paramagnetic metal ion/L (inclusive), particularly in a range of 80 to 650 mmol paramagnetic metal ion/L (inclusive), particularly in a range of 90 to 600 mmol paramagnetic metal ion/L (inclusive), particularly in a range of 100 to 500 mmol paramagnetic metal ion/L (inclusive), particularly in a range of 150 to 450 mmol paramagnetic metal ion/L (inclusive), more particularly in a range of 200 to 400 mmol paramagnetic metal ion/L (inclusive), and even more particularly in a range of 250 to 350 mmol paramagnetic metal ion/L (inclusive).

In accordance with a thirties embodiment of the first aspect, the present disclosure covers a liquid pharmaceutical formulation comprising a DO3A-derived tetra-chelate of general formula (I):

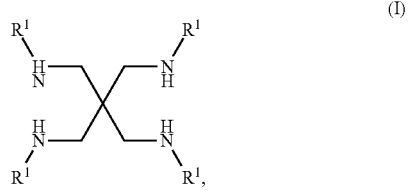
(I)

in which
R¹ represents a group selected from:

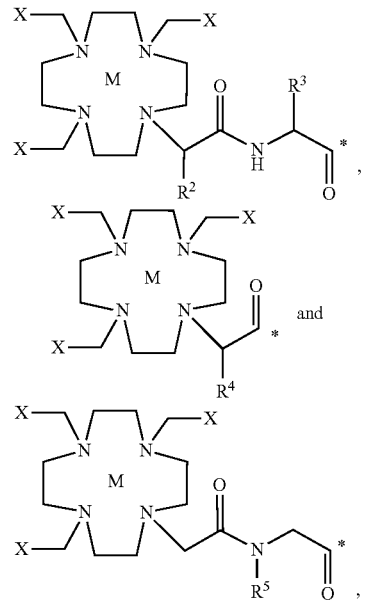

in which group * indicates the point of attachment of said group with the rest of the molecule,
R², R³, and R⁴ independently of each other represents a hydrogen atom or a group selected from:
  $C_1$-$C_6$-alkyl, $C_3$-$C_6$-cycloalkyl, ($C_1$-$C_2$-alkoxy)-($C_2$-$C_3$-alkyl)-, and phenyl,
    wherein said $C_1$-$C_6$-alkyl group is optionally substituted, identically or differently, with a phenyl substituent, which phenyl substituent is optionally substituted, one, two, or three times, identically or differently, with a halogen atom or a group selected from:
      $C_1$-$C_3$-alkyl, $C_1$-$C_3$-haloalkyl, and $C_1$-$C_3$-alkoxy, and
    wherein said phenyl group is optionally substituted, one, two, or three times, identically or differently, with a halogen atom or a group selected from:
      $C_1$-$C_3$-alkyl, $C_1$-$C_3$-haloalkyl, and $C_1$-$C_3$-alkoxy,
R⁵ represents a group selected from:
  $C_1$-$C_6$-alkyl, $C_3$-$C_6$-cycloalkyl, ($C_1$-$C_2$-alkoxy)-($C_2$-$C_3$-alkyl)-, and phenyl,
    wherein said $C_1$-$C_6$-alkyl group is optionally substituted, identically or differently, with a phenyl substituent, which phenyl substituent is optionally substituted, one, two, or three times, identically or differently, with a halogen atom or a group selected from:
      $C_1$-$C_3$-alkyl, $C_1$-$C_3$-haloalkyl, and $C_1$-$C_3$-alkoxy, and
    wherein said phenyl group is optionally substituted, one, two, or three times, identically or differently, with a halogen atom or a group selected from:
      $C_1$-$C_3$-alkyl, $C_1$-$C_3$-haloalkyl, and $C_1$-$C_3$-alkoxy,
X represents a group C(=O)O⁻, and
each M represents a $Gd^{3+}$ ion,
or a stereoisomer, a tautomer, a salt thereof, or a mixture of same, said formulation further comprising
  a sub-stoichiometric chelate, as described herein, in a concentration fraction of 0.01 to 1.25 mol % [with reference to the total molar Gd-concentration], wherein the sub-stoichiometric chelate is selected from one or more of $Gd_3$-DO3A-derived chelate, $Gd_2$-DO3A-derived chelate, Gd-DO3A-derived chelate, and the DO3A-derived tetra-ligand, or mixtures thereof or stereoisomers, tautomers, salts thereof, or a mixture of any thereof,
    wherein the one, two or three DO3A ligands of said sub-stoichiometric chelates, which are not complexed with $Gd^{3+}$ ions, and the four DO3A ligands of the DO3A-derived tetra-ligand, may be present as complexes or salts with $Ca^{2+}$ ions, $Na^+$ ions, $Zn^{2+}$ ions, $Mg^{2+}$ ions, or meglumine ions or as free carboxylic acids,
  a pharmaceutically acceptable solvent, and
  optionally comprising a buffer,
wherein the DO3A-derived tetra-chelate of general formula (I) has a concentration in the formulation in a range of 1 mmol $Gd^{3+}$/L to 1000 mmol $Gd^{3+}$/L (inclusive), particularly in a range of 60 to 750 mmol $Gd^{3+}$/L (inclusive), particularly in a range of 70 to 700 mmol $Gd^{3+}$/L (inclusive), particularly in a range of 80 to 650 mmol $Gd^{3+}$/L (inclusive), particularly in a range of 90 to 600 mmol $Gd^{3+}$/L (inclusive), particularly in a range of 100 to 500 mmol $Gd^{3+}$/L (inclusive), particularly in a range of 150 to 450 mmol $Gd^{3+}$/L (inclusive), more particularly in a range of 200 to 400 mmol $Gd^{3+}$/L (inclusive), and even more particularly in a range of 250 to 350 mmol $Gd^{3+}$/L (inclusive).

Owing in particular to the binding of free paramagnetic metal by BT-DO3A (Butrol) or any other free ligand such as DOTA (1,4,7,10-tetraazacyclododecane tetraacetic acid), DTPA (diethylenetriamine pentaacetic acid), and HP-DO3A (2-hydroxypropyl-1,4,7,10-tetraazacyclododecane triacetic acid), according to certain embodiments, the formulation which is the subject of one or more of the various embodiments of the present disclosure may also comprise a complex between BT-DO3A or any other free ligand and a weak binding metal, optionally including meglumine or other cationic agent, particularly in the range of 0.002% to 0.5% mol/mol (inclusive), particularly in the range of 0.01% to 0.5% mol/mol (inclusive), this proportion being related to the total paramagnetic metal ion concentration, such as $Gd^{3+}$ concentration, in said formulation. Particularly, the complex between BT-DO3A or any other free ligand and a paramagnetic metal ion is a paramagnetic metal chelate. The nature of the metal chelated by BT-DO3A or any other free ligand is predominantly the same as that of the paramagnetic metal chelated by the chelating ligand of the complex of formula (I). However, the formulation according to various embodiments of the disclosure may also comprise a small proportion of free BT-DO3A and/or a complex between BT-DO3A and a metal other than the one chelated by the chelating ligand of the complex of formula (I). The formulation can thus also comprise a complex between BT-DO3A and an ion of any metal that can be extracted from the containers, for example from a surface of a glass, plastic, or metal reaction or storage container, in which the formulation is prepared and/or stored, for example iron, copper, and/or magnesium ion.

Liquid pharmaceutical formulations comprising $Gd_4$-DO3A-derived tetra chelates of general formula (I), as defined supra, display a high relaxivity, which is a measure for the efficiency in MRI imaging procedures, and an improved mass efficiency (cost of industrial production).

According to various embodiments, the formulations may display relaxivity values for $r_1$ in the range of 10 to 14 L $mmol^{-1}$ $s^{-1}$ $Gd^{-1}$ (at 1.41 T, human plasma). The observed relaxivities may range from 2-3 fold higher than those associated with formulations comprising conventional MRI contrast agents, in particular gadobutrol and gadopentetate dimeglumine. The DO3A-derived tetra chelates of general formula (I) are highly suitable for high magnetic field imaging (for example for fields of 3 Tesla). The high relaxivities observed with the pharmaceutical formulations comprising the $Gd_4$-DO3A-derived tetra chelates may allow for improved image quality at lower dosages of paramagnetic metal concentrations. Further, in certain embodiments, lower dosing for the contrast agent may allow for formulations having reduced molar concentrations of the contrast agent in the pharmaceutically acceptable solvent. According to these embodiments, formulations with reduced molar concentrations of the contrast agent may display reduced viscosities compared to conventional MRI contrast agent formulations having higher molar concentrations of contrast agent. Formulations with reduced viscosities may allow for easier administration of equivalent amounts of paramagnetic metal ion with better mixing characteristics with co-administered saline solutions and without significant fluid flow fluctuations, for example when transitioning from injection of high viscosity contrast agent formulation to lower viscosity saline solutions.

The $Gd_4$-DO3A-derived tetra chelates of general formula (I) exhibit several functional characteristics which are particularly outstanding by themselves or in any combination:

In particular, said DO3A-derived tetra chelates according to the various embodiments of the present disclosure have been found to exhibit one or more of:
  a high relaxivity
  a favorable pharmacokinetic profile
  a fast and complete excretion
  a high stability
  a high solubility
  the potential for a significant dose reduction and the potential for whole body imaging.

The compounds described in EP 1931673B1 and Fries P. et al., Invest. Radiol., 2015 December; 50(12):835-42 are having an average hydration number of above 1 (q>1). The increase of the number of inner sphere water molecules is known to increase the relaxivities but it is also known to decrease the stability of the Gd-chelates (Caravan P., Chem. Soc. Rev., 2006, 35, 512-523; Raymond et al, Bioconjugate Chem., 2005, 16, 3-8).

The compounds according to various embodiments of the present disclosure have only one water molecule directly coordinated to the gadolinium within the complex and have a very high stability (q=1).

The viscosity of the formulations of various embodiments of the current disclosure has been found to be only slightly higher than for sodium chloride solution. In certain embodiments of the present disclosure the osmolality of the formulation may be similar to isotonic sodium chloride solution or blood plasma (275 to 295 mOsm/kg, Pediatr. Nephrol. 2018 Sep. 13); i.e. in the range of 200 to 400 mOsm/kg (inclusive), particularly in the range of 250 to 350 mOsm/kg (inclusive), and is considered low compared to other conventional MRI contrast agents. Isotonic formulations for intravenous administration of contrast agents may be of advantage by not having a significant effect on the distribution of water between intracellular and extracellular spaces compared to non-isotonic solutions, such as hypo- or hypertonic solutions. A comparison of the viscosity and osmolality of embodiments of the present formulations and other conventional MRI contrast agents is presented in Table 1. The combination of low viscosity and the isotonicity with blood of the various embodiments of the formulation of the current disclosure leads to a good local tolerance of the intravenous bolus application and allows a convenient and reproducible application through a long and thin catheter during hand injection (less pressure required) and more consistent flow profiles, for example during fluid flow transitions between contrast agent and saline.

TABLE 1

Viscosities and osmolalities of a formulation containing the $Gd_4$-DO3A-derived tetra-chelate of formula (I-a) and of marketed contrast media:

| Product | Viscosity 20° C. [mPas] | Viscosity 37° C. [mPas] | Osmolality [mOsm/kg] |
|---|---|---|---|
| 0.9% (m/v) sodium chloride | 1.03* | 0.74* | 287** |
| Formulation containing $Gd_4$-DO3A-derived tetra-chelate of formula (I-a) | 1.87* | 1.22* | 294* |
| Gadovist ® 1.0 | 8.86*** | 4.96*** | 1603*** |
| Dotarem ® | 3.4[#] | 2.4[#] | 1350[#] |
| ProHance ® | 2.0[##] | 1.3[##] | 630[##] |
| Magnevist ® | 4.9[##] | 2.9[##] | 1960[##] |
| Omniscan ® | 2.0[##] | 1.4[##] | 789[##] |
| OptiMARK ® | 3.1[##] | 2.0[##] | 1110[##] |
| MultiHance ® | 9.2[##] | 5.3[##] | 1970[##] |

*Experimental Section, Example 3
**Pediatr. Nephrol. 2018 Sep. 13
***Fachinformation des Arzneimittel-Kompendium der Schweiz ®
[#]Highlights of Prescribing Information (https://www.accessdata.fda.gov/drugsatfda_docs/label/2017/204781s001lbl.pdf)
[##]J. Magn. Res. Imaging, 25, 884-899, 2007

In accordance with a thirty-first embodiment of the first aspect, the pH of the formulations may be in a range of 4.5 to 8.5 (inclusive), particularly in a range of 6.6 to 8.0 (inclusive), more particularly in a range of 6.9 to 7.9 (inclusive), more particularly in a range of 7.2 to 7.6. more particularly wherein the pH is 7.4. Formulations having a pH within these ranges make it possible in particular to have an isohydric solution in comparison to in vivo conditions (pH 7.4).

In accordance with a thirty-second embodiment of the first aspect, the formulations according to various embodiments of the present disclosure may be buffered, i.e. it comprises at least one buffer chosen from buffers established for the pH range of 4.5 to 8.5 (inclusive), which buffers are chosen from citrate, lactate, acetate, tartrate, malate, maleate, phosphate, succinate, ascorbate, carbonate, trometamol (TRIS, 2-amino-2-(hydroxymethyl)propane-1,3-diol), HEPES (2-[4-(2-hydroxyethyl)-1-piperazine]ethanesulfonic acid) and MES (2-morpholinoethanesulfonic acid) and mixtures thereof, and particularly the buffer is trometamol.

Process for Preparing a Pharmaceutical Formulation of the Contrast Agent

In accordance with a second aspect, the present disclosure covers a process for preparing a liquid pharmaceutical formulation according to the present disclosure, which process comprises the following steps:
a) Providing a pharmaceutically acceptable solvent;
b) Optionally dissolving a buffer, thereby obtaining a buffered solution and optionally adjusting the pH of the solution to a pH in a range of 7.6 to 8.2 (inclusive);
c) Optionally dissolving a compound capable of forming a chelate with any free paramagnetic metal ion M;
d) Dissolving a DO3A-derived tetra-chelate of formula (I) as defined supra, in sufficient amount to produce a final solution having a formulation having a concentration of DO3A-derived tetra-chelate of formula (I) in a range of 1 to 1000 mmol paramagnetic metal ion/L (inclusive), wherein the ion of the paramagnetic metal is not $Gd^{3+}$; and in sufficient amount to produce a final solution having a formulation having a concentration of the DO3A-derived tetra-chelate of formula (I) in a range of 60 to 750 mmol paramagnetic metal ion/L (inclusive), wherein the ion of the paramagnetic metal can also be $Gd^{3+}$, particularly in a range of 70 to 700 mmol paramagnetic metal ion/L (inclusive), particularly in a range of 80 to 650 mmol paramagnetic metal ion/L (inclusive), particularly in a range of 90 to 600 mmol paramagnetic metal ion/L (inclusive), particularly in a range of 100 to 500 mmol paramagnetic metal ion/L (inclusive), particularly in a range of 150 to 450 mmol paramagnetic metal ion/L (inclusive), more particularly in a range of 200 to 400 mmol paramagnetic metal ion/L (inclusive), and even more particularly in a range of 250 to 350 mmol paramagnetic metal ion/L (inclusive).
e) Optionally dissolving an isotonicity agent in the solution;
f) Optionally adjusting the pH of the solution to a pH in a range of 4.5 to 8.5 (inclusive);
g) Optionally adjusting the concentration of said chelate of said formula (I) by addition of an additional amount of the pharmaceutically acceptable solvent; and
h) Optionally sterilizing the solution.

In accordance with a second embodiment of the second aspect, the present disclosure covers a process for preparing a formulation according to various embodiments of the present disclosure, which process comprises the following steps:
a) Providing a pharmaceutically acceptable solvent;
b) Optionally dissolving a buffer, thereby obtaining a buffered solution and optionally adjusting the pH of the solution to a pH in a range of 7.6 to 8.2 (inclusive);
c) Dissolving a compound capable of forming a chelate with any free paramagnetic metal ion M;
d) Dissolving a DO3A-derived tetra-chelate of formula (I) as defined supra, in sufficient amount to produce a final solution having a formulation having a concentration of the DO3A-derived tetra-chelate of formula (I) in a range of 1 to 1000 mmol paramagnetic metal ion/L (inclusive), particularly in a range of 60 to 750 mmol paramagnetic metal ion/L (inclusive), particularly in a range of 70 to 700 mmol paramagnetic metal ion/L (inclusive), particularly in a range of 80 to 650 mmol paramagnetic metal ion/L (inclusive), particularly in a range of 90 to 600 mmol paramagnetic metal ion/L (inclusive), particularly in a range of 100 to 500 mmol paramagnetic metal ion/L (inclusive), particularly in a range of 150 to 450 mmol paramagnetic metal ion/L (inclusive), more particularly in a range of 200 to 400 mmol paramagnetic metal ion/L (inclusive), and even more particularly in a range of 250 to 350 mmol paramagnetic metal ion/L (inclusive);
e) Optionally dissolving an isotonicity agent in the solution;
f) Optionally adjusting the pH of the solution to a pH in a range of 4.5 to 8.5 (inclusive);
g) Optionally adjusting the concentration of said chelate of said formula (I) by addition of an additional amount of the pharmaceutically acceptable solvent; and
h) Optionally sterilizing the solution.

According to the various embodiments, the order of steps b), c), d) and e) is interchangeable. That is, when performing the method, the lettered identifiers (i.e., a), b), c), etc.) are not intended to indicate a specific order of conducting the steps of the method.

According to various embodiments, the order of steps f) and g) is interchangeable.

The term "pharmaceutically acceptable solvent" is intended to include solvents which are suitable with parenteral application, i.e. with intravenous injection. Particularly, this solvent may be water for injection, or a saline solution, more particularly water for injection.

The term "buffer solution" is intended to mean a solution in a pharmaceutically acceptable solvent which comprises a buffer established for a pH range 4.5 to 8.5 (inclusive), particularly a range of 6.6 to 8.0 (inclusive), more particularly a range of 6.9 to 7.9 (inclusive), more particularly a range of 7.2 to 7.6. Even more particularly the pH is adjusted to a value of 7.4. The buffer used in step b) is chosen from citrate, lactate, acetate, tartrate, malate, maleate, phosphate, succinate, ascorbate, carbonate, trometamol (TRIS, 2-amino-2-(hydroxymethyl)propane-1,3-diol), HEPES (2-[4-(2-hydroxyethyl)-1-piperazine]ethanesulfonic acid), and MES (2-morpholinoethanesulfonic acid) and mixtures thereof, and particularly the buffer is trometamol.

The adjustment of the pH, for example in step b), may be carried out by adding one of the buffers mentioned above and/or raising the pH by adding an aqueous solution of a base (e.g., sodium hydroxide or meglumine) or lowering the pH by adding an aqueous solution of an acid (e.g., hydrochloric acid).

The compound capable of forming a chelate with any free paramagnetic metal ion M added in step c) is chosen from Ca-BT-DO3A (Calcobutrol), Ca-DOTA, Ca-HP-DO3A and Ca-DTPA or from the respective free ligands, or salts thereof with alkaline metals, alkaline earth metals, weakly bound transition metals or organic bases. Particularly the compound capable of forming a complex with any free paramagnetic metal ion M is Ca-BT-DO3A (Calcobutrol), preferably in a range of 0.002% to 5% mol/mol (inclusive), measured as a proportion relative to the total Gd concentration in the formulation.

The step c) of addition of Ca-BT-DO3A is advantageously carried out at a temperature range of 15 to 60° C. (inclusive), preferably 15 to 40° C. (inclusive).

The DO3A-derived tetra-chelate of formula (I) added in step d) is preferably a $Gd_4$-DO3A-derived tetra-chelate, particularly selected from the chelates of formulae (I-a), (I-b) and (I-c), as defined supra, more particularly the DO3A-derived tetra-chelate of formula (I) is the $Gd_4$-DO3A-derived tetra-chelate of formula (I-a), as defined supra.

The DO3A-derived tetra-chelate of formula (I) is added in step d) at a temperature range of 15 to 60° C. (inclusive), particularly 15 to 40° C. (inclusive), in sufficient amount to produce a final solution having a liquid pharmaceutical formulation having a concentration of DO3A-derived tetra-chelate of formula (I) in a range of 1 to 1000 mmol paramagnetic metal ion/L (inclusive) wherein the paramagnetic metal ion is not $Gd^{3+}$, or when a compound capable of forming a complex with any free paramagnetic metal ion M is added in step c) the paramagnetic metal ion can be $Gd^{3+}$; and in sufficient amount to produce a final solution having a liquid pharmaceutical formulation having a concentration of DO3A-derived tetra-chelate of formula (I) in a range of 60 to 750 mmol paramagnetic metal ion/L (inclusive), wherein the paramagnetic metal ion can also be $Gd^{3+}$, particularly in a range of 70 to 700 mmol paramagnetic metal ion/L (inclusive), particularly in a range of 80 to 650 mmol paramagnetic metal ion/L (inclusive), particularly in a range of 90 to 600 mmol paramagnetic metal ion/L (inclusive), particularly in a range of 100 to 500 mmol paramagnetic metal ion/L (inclusive), particularly in a range of 150 to 450 mmol paramagnetic metal ion/L (inclusive), more particularly in a range of 200 to 400 mmol paramagnetic metal ion/L (inclusive), and even more particularly in a range of 250 to 350 mmol paramagnetic metal ion/L (inclusive).

The fact, that the mixing step d) can be performed without heating is of advantage, because chemical reactions/decomposition which would result in potentially toxic products are avoided.

The isotonicity agent added in step e) particularly is sodium chloride.

The amount of sodium chloride added in step e) is added in order to produce a formulation, which preferably is isotonic to blood plasma.

The pH of the solution in step f) is adjusted to a pH in a range of pH 4.5 to 8.5 (inclusive), particularly in a range of 6.6 to 8.0 (inclusive), more particularly in a range of 6.9 to 7.9 (inclusive), more particularly in a range of 7.2 to 7.6. Even more particularly the pH is adjusted to a value of 7.4.

Step f) of adjustment of the pH is particularly carried out by adding one of the buffers mentioned above and/or by adding an aqueous solution of a base (e.g. sodium hydroxide or meglumine) or an aqueous solution of an acid (e.g. hydrochloric acid).

Step g) of adjustment of the concentration of said chelate of said formula (I), is particularly carried out after measurement of the density of the formulation, by addition of a pharmaceutically acceptable solvent. The target concentration of chelate of formula (I) in the formulation is in a range of 1 to 1000 mmol paramagnetic metal ion/L (inclusive) wherein the ion of the paramagnetic metal is not $Gd^{3+}$, or when a compound capable of forming a complex with any free paramagnetic metal ion M is added in step c) the paramagnetic metal ion can be $Gd^{3+}$; and in sufficient amount to produce a final solution having a liquid pharmaceutical formulation having a concentration of DO3A-derived tetra-chelate of formula (I) in a range of 60 to 750 mmol paramagnetic metal ion/L (inclusive), wherein the ion of the paramagnetic metal can also be $Gd^{3+}$, particularly in a range of 70 to 700 mmol paramagnetic metal ion/L (inclusive), particularly in a range of 80 to 650 mmol paramagnetic metal ion/L (inclusive), particularly in a range of 90 to 600 mmol paramagnetic metal ion/L (inclusive), particularly in a range of 100 to 500 mmol paramagnetic metal ion/L (inclusive), particularly in a range of 150 to 450 mmol paramagnetic metal ion/L (inclusive), more particularly in a range of 200 to 400 mmol paramagnetic metal ion/L (inclusive), and even more particularly in a range of 250 to 350 mmol paramagnetic metal ion/L (inclusive).

The step g) of adjustment of the concentration of the chelate of formula (I) as defined supra is particularly a step of adjustment of the volume by adding pharmaceutically acceptable solvent so as to adjust the density of the liquid formulation to a density in a range of 1.0 to 1.3 $g \cdot cm^{-3}$ (inclusive), particularly in a range of 1.0 to 1.2 $g \cdot cm^{-3}$, more particularly to a density in a range of 1.075 to 1.125 $g \cdot cm^{-3}$.

Step h) of sterilization of the formulation is carried out according to methods known to those skilled in the art.

In accordance with a third embodiment of the second aspect, the present disclosure covers a process for preparing a liquid pharmaceutical formulation, wherein the step of dissolving the DO3A-derived tetra-chelate of formula (I) comprises:

dissolving a DO3A-derived tetra-chelate of formula (I) as defined supra, in a pharmaceutically acceptable solvent or an aqueous buffer to provide a first solution, wherein the DO3A-derived tetra-chelate of formula (I) is dissolved in sufficient amount to produce a liquid pharmaceutical formulation having a concentration of the DO3A-derived tetra-chelate of formula (I) in a range of 1 to 1000 mmol paramagnetic metal ion/L (inclusive), wherein the ion of the paramagnetic metal is not $Gd^{3+}$; and in a range of 60 to 750 mmol paramagnetic metal ion/L (inclusive), wherein the ion of the paramagnetic metal can also be $Gd^{3+}$, particularly in a range of 70 to 700 mmol paramagnetic metal ion/L (inclusive), particularly in a range of 80 to 650 mmol paramagnetic metal ion/L (inclusive), particularly in a range of 90 to 600 mmol paramagnetic metal ion/L (inclusive), particularly in a range of 100 to 500 mmol paramagnetic metal ion/L (inclusive), particularly in a range of 150 to 450 mmol paramagnetic metal ion/L (inclusive), more particularly in a range of 200 to 400 mmol paramagnetic metal ion/L (inclusive), and even more particularly in a range of 250 to 350 mmol paramagnetic metal ion/L (inclusive).

In accordance with a fourth embodiment of the second aspect, the present disclosure covers a process for preparing a formulation according to the present disclosure, wherein the process comprises:
dissolving an amount of the compound capable of forming a chelate with free paramagnetic metal ion M in the range of 0.002% to 5% mol/mol (inclusive) with reference to the total concentration of the paramagnetic metal ion in the formulation in the pharmaceutically acceptable solvent or an aqueous buffer solution to provide a first solution;
dissolving the DO3A-derived tetra-chelate of formula (I) as defined supra, in the first solution in sufficient amount to produce a final solution having a liquid pharmaceutical formulation having a concentration of the DO3A-derived tetra-chelate of formula (I) in a range of 1 mmol paramagnetic metal ion/L to 1000 mmol paramagnetic metal ion/L (inclusive), particularly in a range of 60 to 750 mmol paramagnetic metal ion/L (inclusive), particularly in a range of 70 to 700 mmol paramagnetic metal ion/L (inclusive), particularly in a range of 80 to 650 mmol paramagnetic metal ion/L (inclusive), particularly a the range of 90 to 600 mmol paramagnetic metal ion/L (inclusive), particularly in a range of 100 to 500 mmol paramagnetic metal ion/L (inclusive), particularly in a range of 150 to 450 mmol paramagnetic metal ion/L (inclusive), more particularly in a range of 200 to 400 mmol paramagnetic metal ion/L (inclusive), and even more particularly in a range of 250 to 350 mmol paramagnetic metal ion/L (inclusive).

In accordance with a fifth embodiment of the second aspect, the present disclosure covers a process for preparing a liquid pharmaceutical formulation, wherein the step of dissolving the DO3A-derived tetra-chelate of formula (I) comprises:
dissolving the $Gd_4$-DO3A-derived tetra-chelate of formula (I) as defined supra, in a pharmaceutically acceptable solvent or an aqueous buffer to provide a first solution, wherein the $Gd_4$-DO3A-derived tetra-chelate of formula (I) is dissolved in sufficient amount to produce a liquid pharmaceutical formulation having a concentration of the $Gd_4$-DO3A-derived tetra-chelate of formula (I) in a range of 60 to 750 mmol $Gd^{3+}$/L (inclusive), particularly in a range of 70 to 700 mmol $Gd^{3+}$/L (inclusive), particularly in a range of 80 to 650 mmol $Gd^{3+}$/L (inclusive), particularly in a range of 90 to 600 mmol $Gd^{3+}$/L (inclusive), particularly in a range of 100 to 500 mmol $Gd^{3+}$/L (inclusive), particularly in a range of 150 to 450 mmol $Gd^{3+}$/L (inclusive), more particularly in a range of 200 to 400 mmol $Gd^{3+}$/L (inclusive), and even more particularly in a range of 250 to 350 mmol $Gd^{3+}$/L (inclusive).

In accordance with a sixth embodiment of the second aspect, the present disclosure covers a process for preparing a formulation according to the present disclosure, wherein the process comprises:
dissolving an amount of a compound capable of forming a complex with free paramagnetic metal ion M in a range of 0.002% to 5% mol/mol (inclusive) with reference to the total concentration of the paramagnetic metal ion in the formulation in a pharmaceutically acceptable solvent or an aqueous buffer solution to provide a first solution;
dissolving a $Gd_4$-DO3A-derived tetra-chelate of formula (I) as defined supra, in sufficient amount to produce a final solution having a liquid pharmaceutical formulation having a concentration of the DO3A-derived tetra-chelate of formula (I) in the range of 1 mmol $Gd^{3+}$/L to 1000 mmol $Gd^{3+}$/L (inclusive), particularly in the range of 60 to 750 mmol $Gd^{3+}$/L (inclusive), particularly in the range of 70 to 700 mmol $Gd^{3+}$/L (inclusive), particularly in the range of 80 to 650 mmol $Gd^{3+}$/L (inclusive), particularly in the range of 90 to 600 mmol $Gd^{3+}$/L (inclusive), particularly in the range of 100 to 500 mmol $Gd^{3+}$/L (inclusive), particularly in the range of 150 to 450 mmol $Gd^{3+}$/L (inclusive), more particularly in the range of 200 to 400 mmol $Gd^{3+}$/L (inclusive), and even more particularly in the range of 250 to 350 mmol $Gd^{3+}$/L (inclusive).

In accordance with a seventh embodiment of the second aspect, the present disclosure covers a process for preparing a formulation according to the present disclosure, wherein the process comprises:
dissolving an amount of Ca-BT-DO3A in the range of 0.002% to 5% mol/mol (inclusive) with reference to the total concentration of the paramagnetic metal ion in the formulation in a pharmaceutically acceptable solvent or an aqueous buffer solution to provide a first solution;
dissolving a $Gd_4$-DO3A-derived tetra-chelate of formula (I) as defined supra, in sufficient amount to produce a final solution having a liquid pharmaceutical formulation having a concentration of the $Gd_4$-DO3A-derived tetra-chelate of formula (I) in the range of 1 mmol $Gd^{3+}$/L to 1000 mmol $Gd^{3+}$/L (inclusive), particularly in the range of 60 to 750 mmol $Gd^{3+}$/L (inclusive), particularly in the range of 70 to 700 mmol $Gd^{3+}$/L (inclusive), particularly in the range of 80 to 650 mmol $Gd^{3+}$/L (inclusive), particularly in the range of 90 to 600 mmol $Gd^{3+}$/L (inclusive), particularly in the range of 100 to 500 mmol $Gd^{3+}$/L (inclusive), particularly in the range of 150 to 450 mmol $Gd^{3+}$/L (inclusive), more particularly in the range of 200 to 400 mmol $Gd^{3+}$/L In accordance with an eighth embodiment of the second aspect, the present disclosure covers a process for preparing a liquid pharmaceutical formulation, wherein the step of dissolving the DO3A-derived tetra-chelate of formula (I) comprises:

dissolving a $Gd_4$-DO3A-derived tetra-chelate of formula (I-a) as defined supra, in the pharmaceutically acceptable solvent or an aqueous buffer to provide a first solution, wherein the $Gd_4$-DO3A-derived tetra-chelate of formula (I-a) is dissolved in sufficient amount to produce a liquid pharmaceutical formulation having a concentration of the $Gd_4$-DO3A-derived tetra-chelate of formula (I-a) in the range of 60 to 750 mmol $Gd^{3+}$/L (inclusive), particularly in a range of 70 to 700 mmol $Gd^{3+}$/L (inclusive), particularly in a range of 80 to 650 mmol $Gd^{3+}$/L (inclusive), particularly in a range of 90 to 600 mmol $Gd^{3+}$/L (inclusive), particularly in a range of 100 to 500 mmol $Gd^{3+}$/L (inclusive), particularly in a range of 150 to 450 mmol $Gd^{3+}$/L (inclusive), more particularly in a range of 200 to 400 mmol $Gd^{3+}$/L (inclusive), and even more particularly in a range of 250 to 350 mmol $Gd^{3+}$/L (inclusive).

In accordance with a ninth embodiment of the second aspect, the present disclosure covers a process for preparing a formulation according to the present disclosure, wherein the process comprises:

dissolving an amount of a compound capable of forming a complex with free paramagnetic metal ion M in a range of 0.002% to 5% mol/mol (inclusive) with reference to the total concentration of the paramagnetic metal ion in the formulation in the pharmaceutically acceptable solvent or an aqueous buffer solution to provide a first solution;

dissolving a $Gd_4$-DO3A-derived tetra-chelate of formula (I-a) as defined supra, in the first solution in sufficient amount to produce a final solution having a liquid pharmaceutical formulation having a concentration of the $Gd_4$-DO3A-derived tetra-chelate of formula (I-a) in a range of 1 mmol $Gd^{3+}$/L to 1000 mmol $Gd^{3+}$/L (inclusive), particularly in a range of 60 to 750 mmol $Gd^{3+}$/L (inclusive), particularly in a range of 70 to 700 mmol $Gd^{3+}$/L (inclusive), particularly in a range of 80 to 650 mmol $Gd^{3+}$/L (inclusive), particularly in a range of 90 to 600 mmol $Gd^{3+}$/L (inclusive), particularly in a range of 100 to 500 mmol $Gd^{3+}$/L (inclusive), particularly in a range of 150 to 450 mmol $Gd^{3+}$/L (inclusive), more particularly in a range of 200 to 400 mmol $Gd^{3+}$/L (inclusive), and even more particularly in a range of 250 to 350 mmol $Gd^{3+}$/L (inclusive).

In accordance with a tenth embodiment of the second aspect, the present disclosure covers a process for preparing a formulation according to the present disclosure, wherein the process comprises:

dissolving an amount of Ca-BT-DO3A in a range of 0.002% to 5% mol/mol (inclusive) with reference to the total concentration of the paramagnetic metal ion in the formulation in the pharmaceutically acceptable solvent or an aqueous buffer solution to provide a first solution;

dissolving a $Gd_4$-DO3A-derived tetra-chelate of formula (I-a) as defined supra, in the first solution in sufficient amount to produce a final solution having a liquid pharmaceutical formulation having a concentration of the $Gd_4$-DO3A-derived tetra-chelate of formula (I-a) in a range of 1 mmol $Gd^{3+}$/L to 1000 mmol $Gd^{3+}$/L (inclusive), particularly in a range of 60 to 750 mmol $Gd^{3+}$/L (inclusive), particularly in a range of 70 to 700 mmol $Gd^{3+}$/L (inclusive), particularly in a range of 80 to 650 mmol $Gd^{3+}$/L (inclusive), particularly in a range of 90 to 600 mmol $Gd^{3+}$/L (inclusive), particularly in a range of 100 to 500 mmol $Gd^{3+}$/L (inclusive), particularly in a range of 150 to 450 mmol $Gd^{3+}$/L (inclusive), more particularly in a range of 200 to 400 mmol $Gd^{3+}$/L (inclusive), and even more particularly in a range of 250 to 350 mmol $Gd^{3+}$/L (inclusive).

In accordance with a eleventh embodiment of the second aspect, the present disclosure covers a process for preparing a formulation according to the present disclosure, wherein the process further comprises:

adjusting the pH of the contrast solution to a pH in the range of 4.5 to 8.5 (inclusive), particularly in the range of 6.6 to 8.0, (inclusive), more particularly in the range of 6.9 to 7.9 (inclusive), more particularly in the range of 7.2 to 7.6, more particularly adjusting the pH to 7.4.

In accordance with a twelfth embodiment of the second aspect, the process comprises the steps a) and d), and optionally any of the steps b), c), e), f), g) and h) or combinations thereof, said steps being as previously defined.

In accordance with a third aspect, the present disclosure covers a liquid pharmaceutical formulation obtained according to the process for preparing a formulation according to the various embodiments of the present disclosure.

Use of the Formulations and Contrast Media

In accordance with a fourth aspect, the present disclosure covers the use of a formulation according to the present disclosure for medical imaging, or for diagnostic monitoring of the efficacy of a therapeutic treatment, comprising the administration of a pharmaceutically acceptable amount of a pharmaceutical formulation as described above.

Embodiments of the present disclosure thus relate to a contrast medium for medical imaging, comprising such a liquid pharmaceutical formulation.

In accordance with a second embodiment of the fourth aspect, the present disclosure covers the use of a formulation according to the present disclosure or the contrast media previously described for contrast-enhanced MRI sequences for all body regions. Applications for the formulation according to the present disclosure include cardiovascular, oncological and inflammatory indications for different body regions.

In accordance with a third embodiment of the fourth aspect, the present disclosure covers the use of a formulation according to the present disclosure or the contrast media previously described for the detection and characterization of CNS lesions, lesions of liver and abdomen, lesion in kidney and pelvis, in MR-angiography, as well as for indications in other organs/regions (i.e. tongue, head and neck, cardiovascular system, breast, chest, extremities, joints).

In accordance with a fourth embodiment of the fourth aspect, the present disclosure covers the use of the formulations or the contrast media previously described in the diagnosis of diseases, in particular cancerous, inflammatory, neurological or vascular diseases.

The various embodiments of the present disclosure also relate to said formulations or said contrast media which were previously described, for the use thereof in an imaging method, in particular a method as described below.

In accordance with a fifth aspect, the present disclosure relates to a method for imaging the whole body of an individual, or imaging a part of the body, comprising a step of obtaining one or more images of the whole body or of a part of the body of an individual by means of a medical imaging technique, in which the whole body or the part of the body of the individual comprises the formulation as described supra, in which the image contrast of one or more images is associated with the presence of the DO3A-derived tetra-chelate of general formula (I).

According to another embodiment, the imaging method according to the present disclosure comprises a prior step of injection or of administration of the formulation of the contrast medium to the individual, preferably a parenteral administration, preferably an intravenous, an intra-arterial or an intra-articular injection.

In the medical imaging methods defined above, the images are preferably obtained by Magnetic Resonance Imaging (MRI).

For a diagnosis by MRI, the intravenous administration by injection is typically carried out at a dose in the range of 0.01 to 0.3 mmol Gd/kg body weight (inclusive). The pharmaceutically acceptable dose will depend on the route of administration, and also on the patient and in particular on the nature of the disorder to be studied.

For an intravenous injection and observation by MRI, the concentration of the formulation is typically in the range of 1 to 1000 mmol Gd/L (inclusive), and the dose administered to the patient according to his or her weight will be, as appropriate, in the range of 0.01 to 0.3 mmol Gd/kg body weight (inclusive) and preferably in the range of 0.01 to 0.1 mmol Gd/kg body weight.

Among the advantageous diagnostic indications, mention will be made of the indications already clinically used, and the indications for which the diagnostic outcome are improved by the use of contrast agents.

In accordance with a sixth aspect, the present disclosure covers DO3A-derived tetra-chelates with sub-stoichiometric amounts of gadolinium ions ($Gd^{3+}$), which are selected from the group consisting of:

$Gd_3$-DO3A-derived chelate of formula ($Gd_3$-II-a),

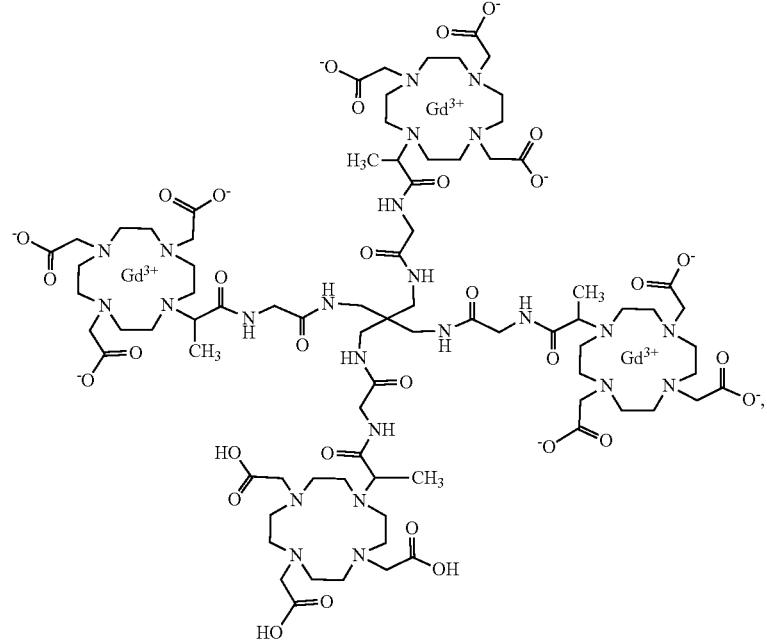

$Gd_2$-DO3A-derived chelate of formula ($Gd_2$-II-a),

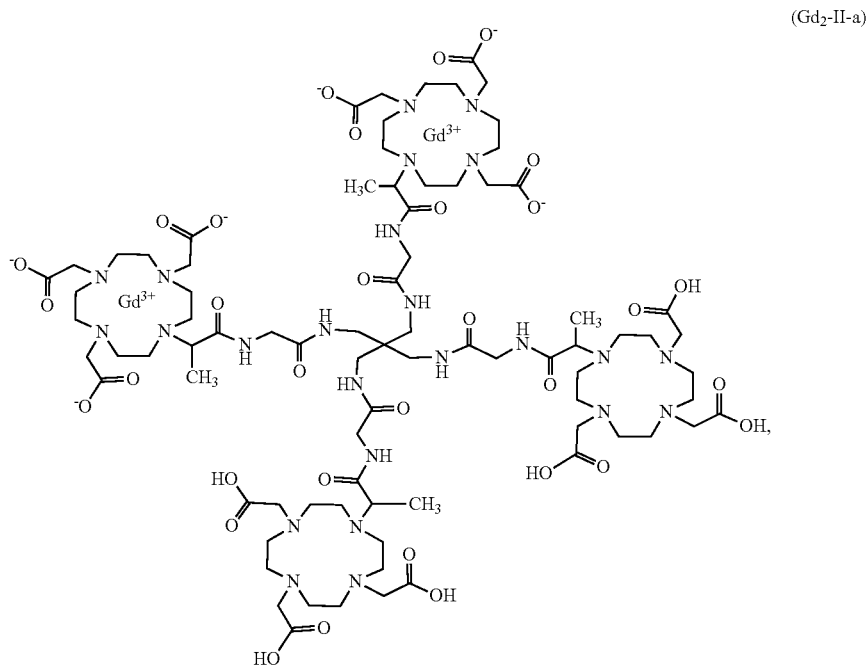

and
Gd-DO3A-derived chelate of formula (Gd-II-a),

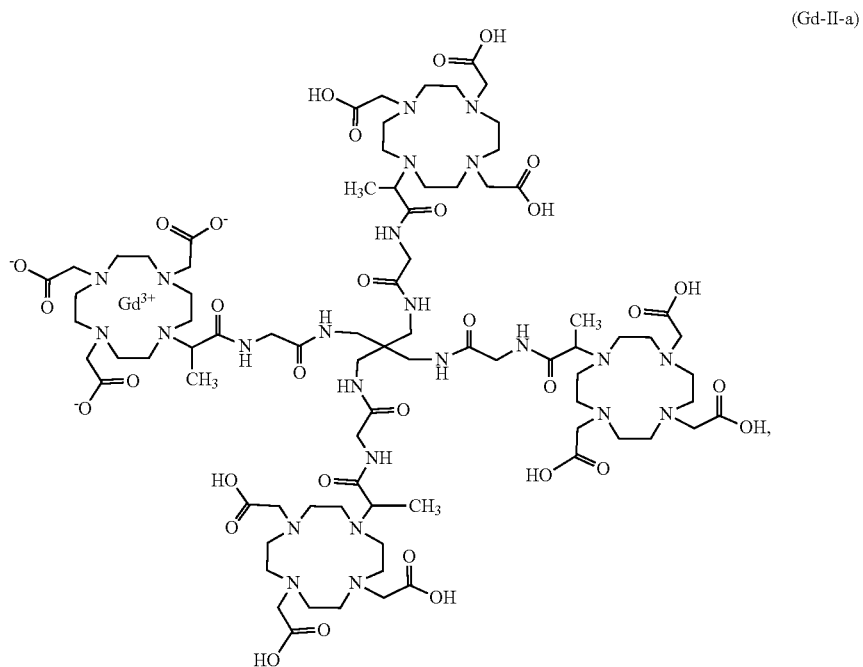

or a stereoisomer, a tautomer or a salt thereof, or a mixture of same.

In accordance with a second embodiment of the sixth aspect, the present disclosure covers DO3A-derived tetra-chelates with sub-stoichiometric amounts of gadolinium ions ($Gd^{3+}$), which are selected from the group consisting of:

Gd$_2$-DO3A-derived chelate of formula (Gd$_2$-II-a), (Gd$_2$-II-a)

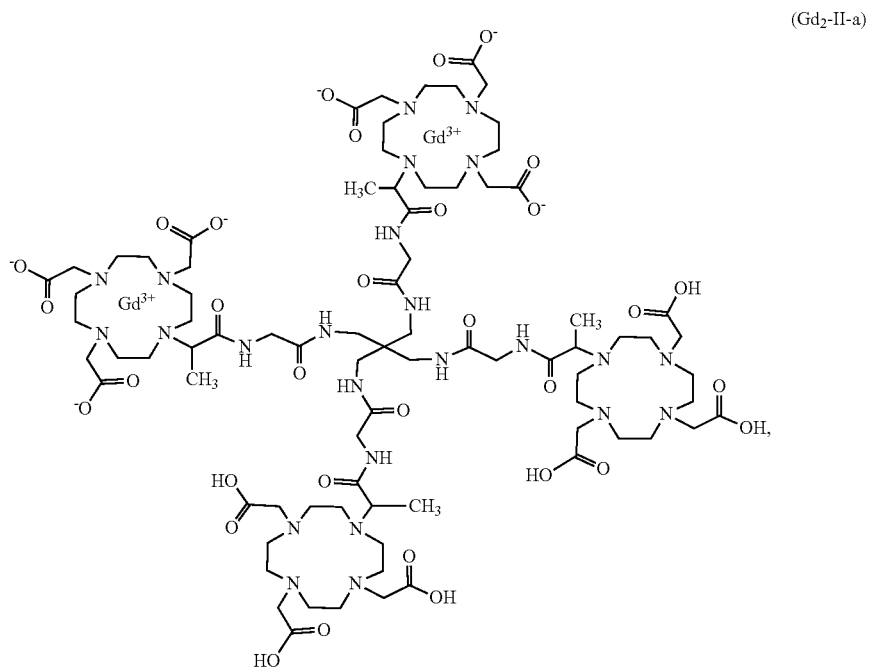

and
Gd-DO3A-derived chelate of formula (Gd-II-a), (Gd-II-a)

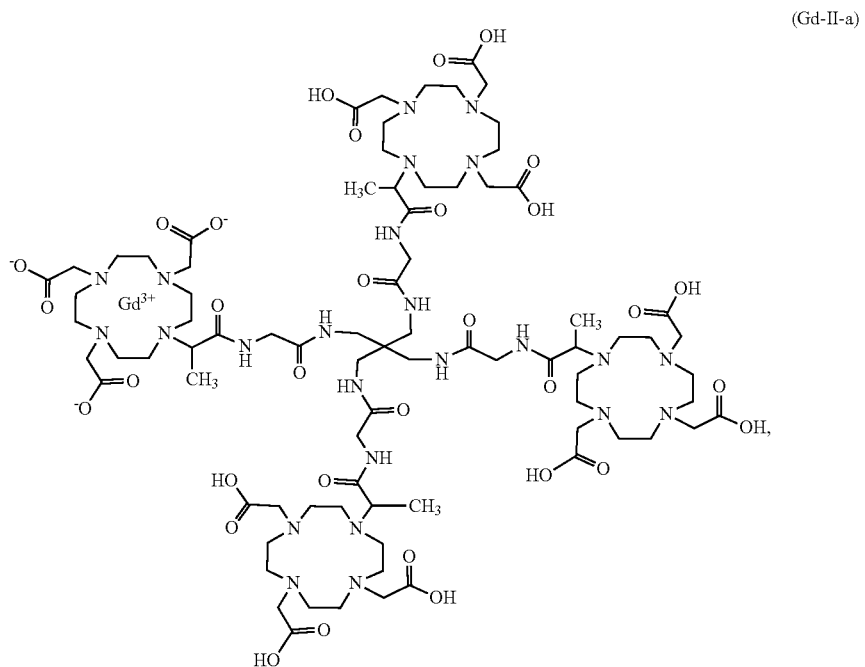

or a stereoisomer, a tautomer or a salt thereof, or a mixture of same.

In accordance with a variant of the sixth aspect, the present disclosure covers DO3A-derived tetra-chelates with sub-stoichiometric amounts of gadolinium ions (Gd$^{3+}$), which are selected from the group consisting of:

Gd₃-DO3A-derived chelate of formula (Gd₃-II-b),
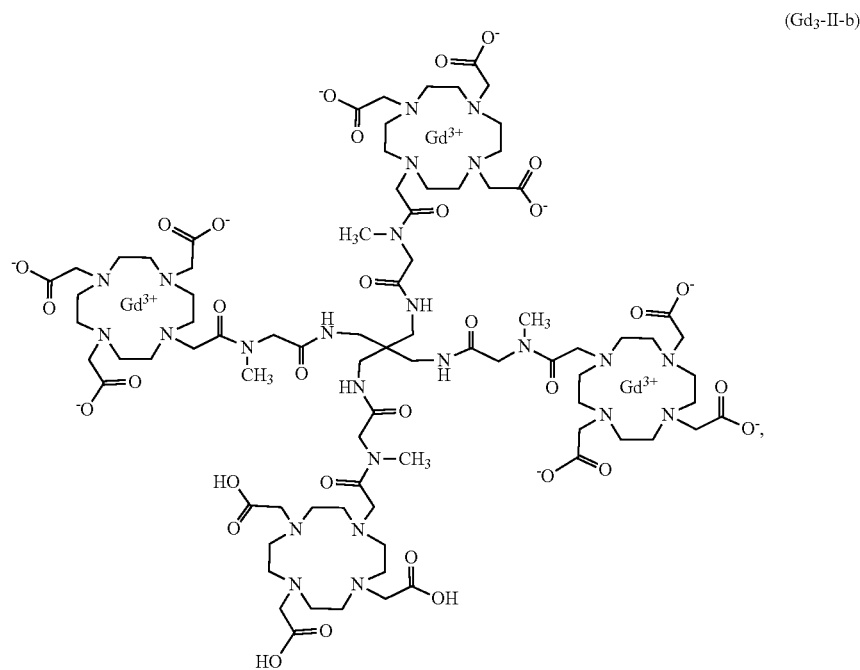
(Gd₃-II-b)
Gd₂-DO3A-derived chelate of formula (Gd₂-II-b),
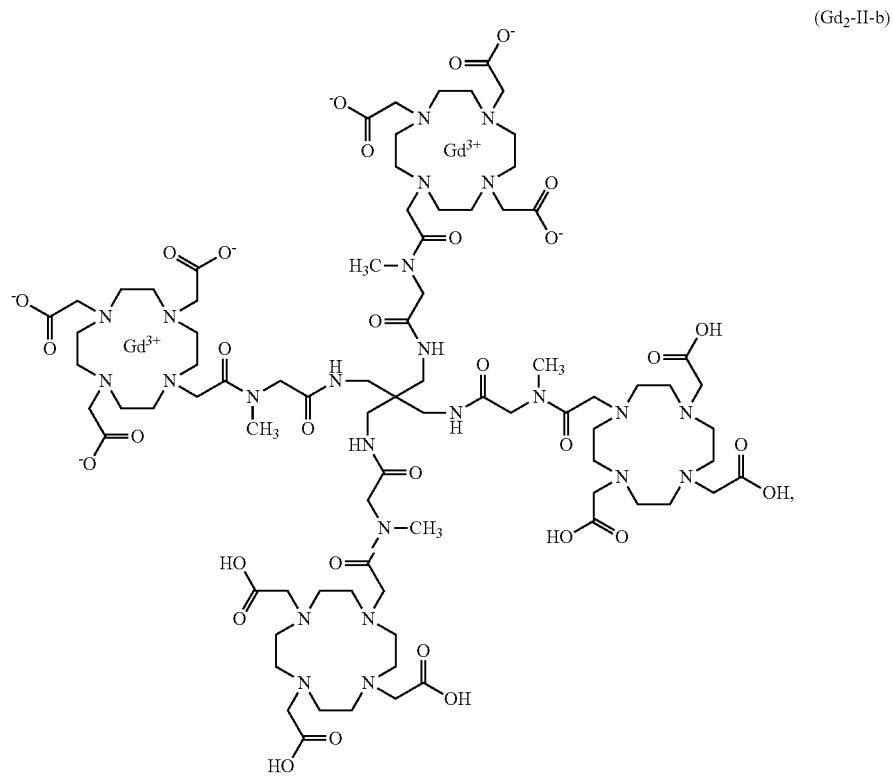
(Gd₂-II-b)

Gd-DO3A-derived chelate of formula (Gd-II-b),
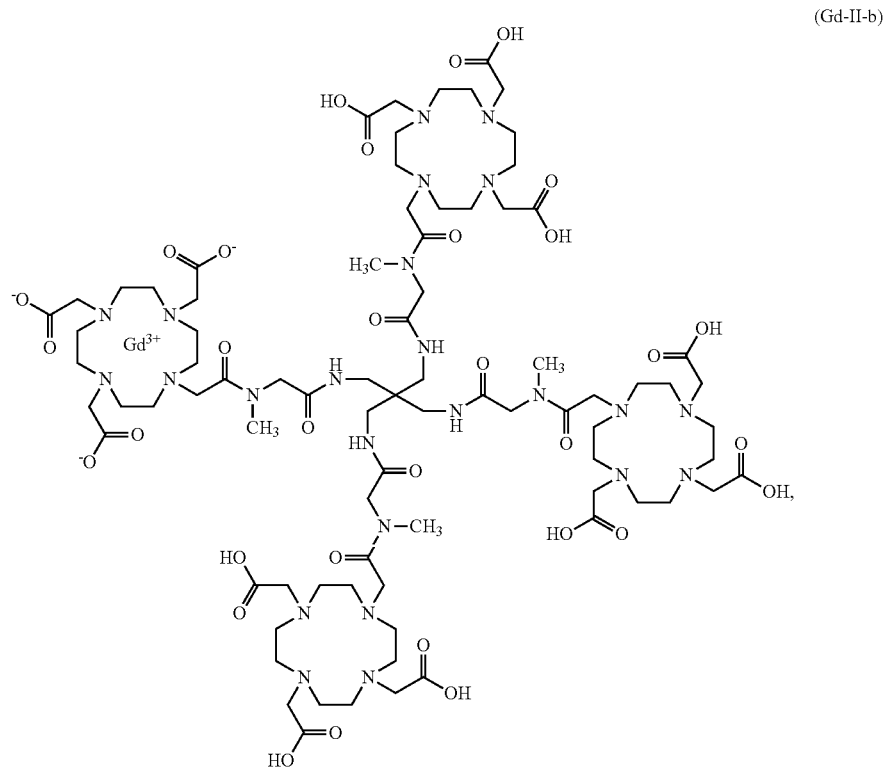
and
Gd DO3A-derived tetra-ligand of formula (II-b),
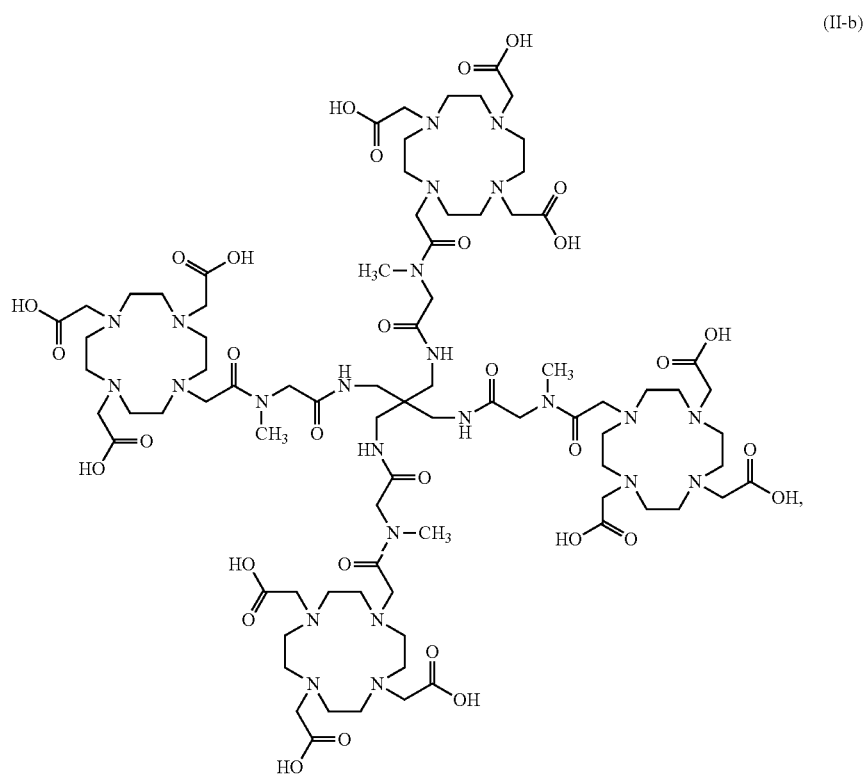 [SMILES: CN(CC(=O)NCC(CNC(=O)CN(C)C(=O)CN1CCN(CC(=O)O)CCN(CC(=O)O)CCN(CC(=O)O)CC1)(CNC(=O)CN(C)C(=O)CN1CCN(CC(=O)O)CCN(CC(=O)O)CCN(CC(=O)O)CC1)CNC(=O)CN(C)C(=O)CN1CCN(CC(=O)O)CCN(CC(=O)O)CCN(CC(=O)O)CC1)C(=O)CN1CCN(CC(=O)O)CCN(CC(=O)O)CCN(CC(=O)O)CC1]

or a stereoisomer, a tautomer or a salt thereof, or a mixture of same.

In accordance with another variant of the sixth aspect, the present disclosure covers DO3A-derived tetra-chelates with sub-stoichiometric amounts of gadolinium ions (Gd³⁺), which are selected from the group consisting of:

Gd$_3$-DO3A-derived chelate of formula (Gd$_3$-II-c),

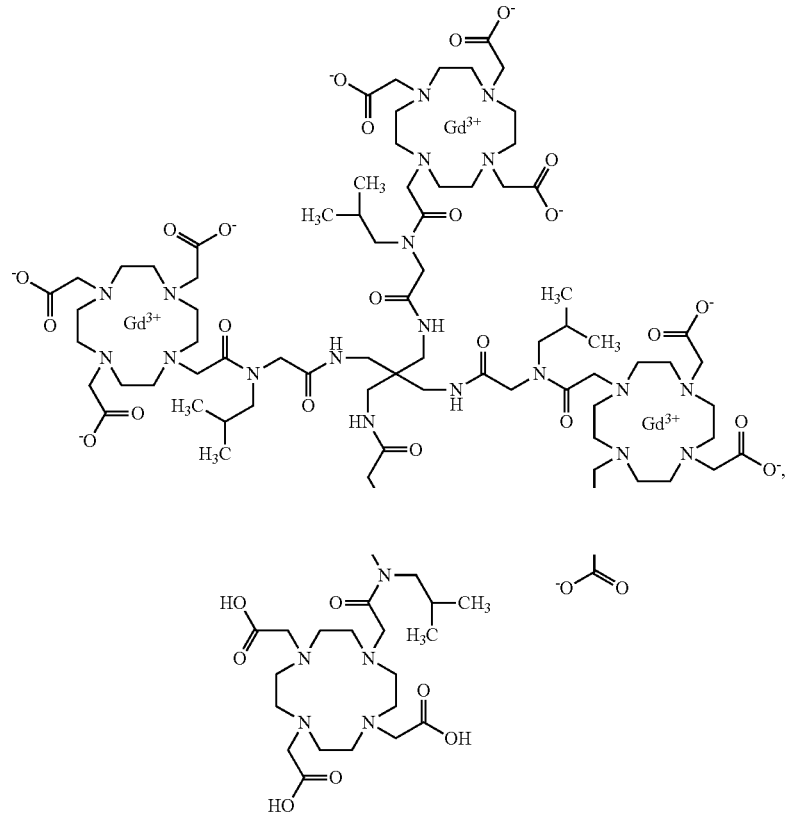

Gd$_2$-DO3A-derived chelate of formula (Gd$_2$-II-c),

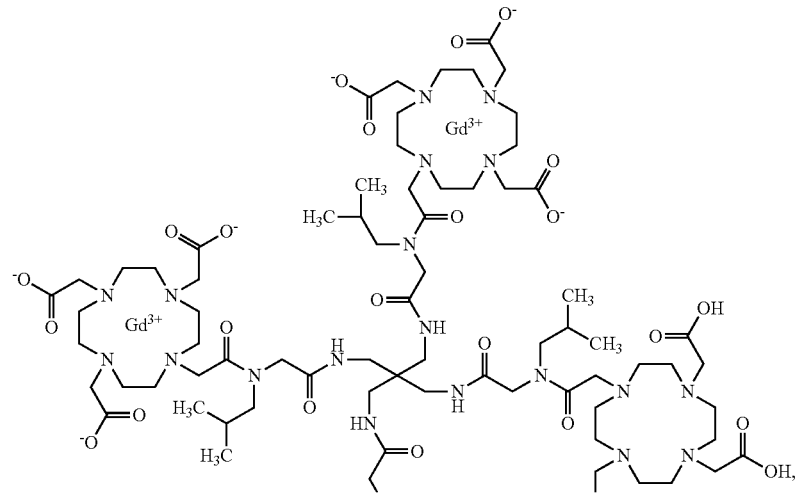

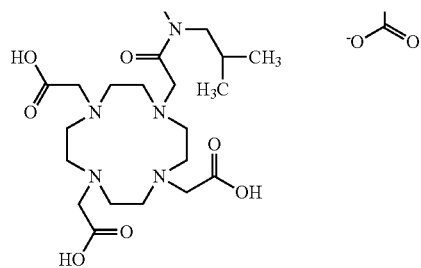
Gd-DO3A-derived chelate of formula (Gd-II-c),
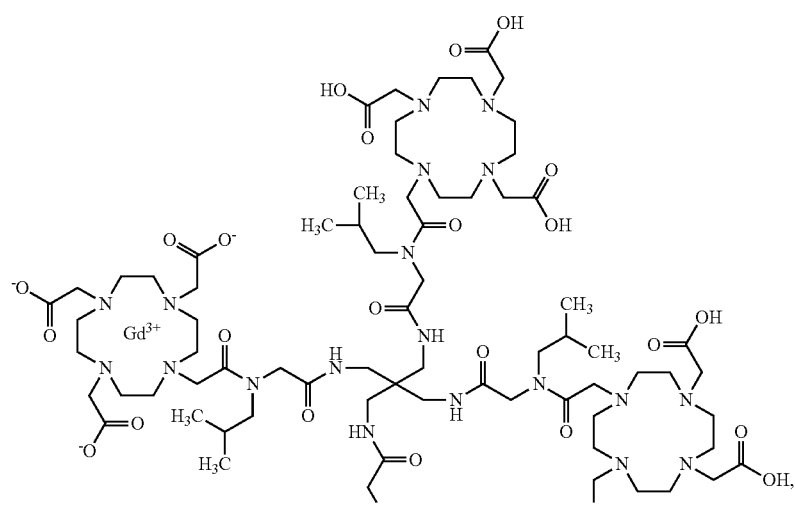
(Gd-II-c)
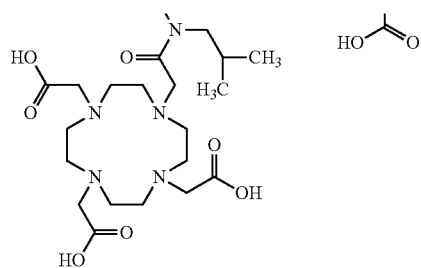

and
DO3A-derived tetra-ligand of formula (II-c),

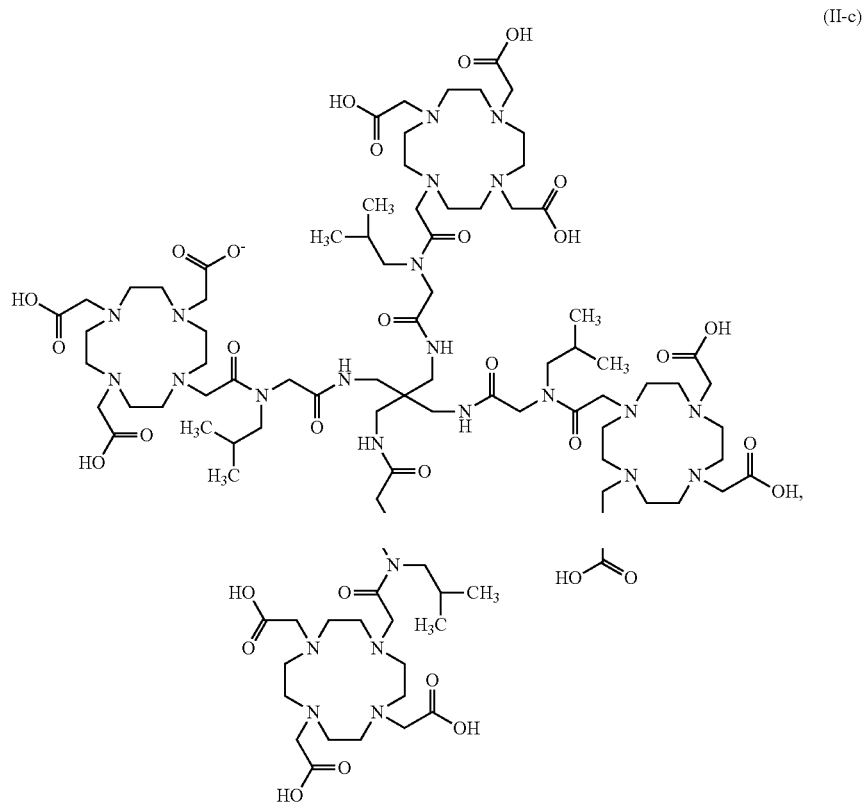

(II-c)

or a stereoisomer, a tautomer or a salt thereof, or a mixture of same.

In accordance with a seventh aspect, the present disclosure covers the use of DO3A-derived tetra-chelates with sub-stoichiometric amounts of gadolinium ions ($Gd^{3+}$), which are selected from the group consisting of:

$Gd_3$-DO3A-derived chelate of formula ($Gd_3$-II-a),

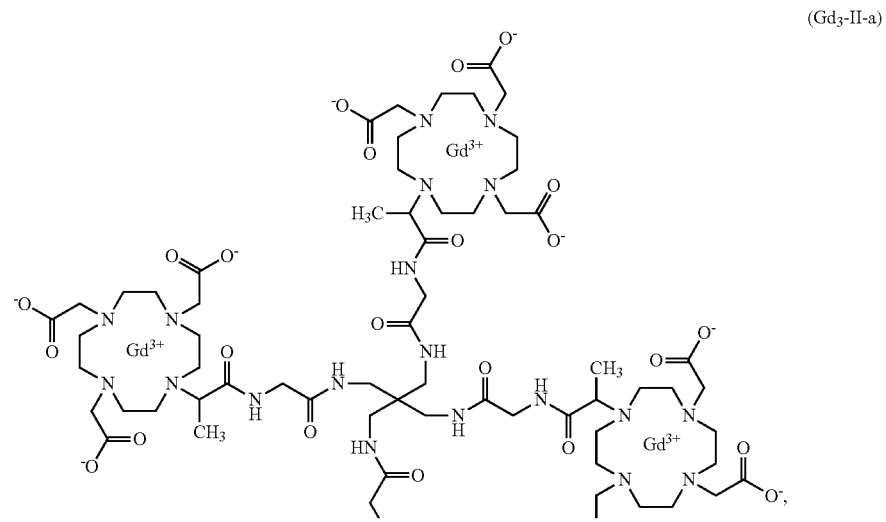

($Gd_3$-II-a)

-continued
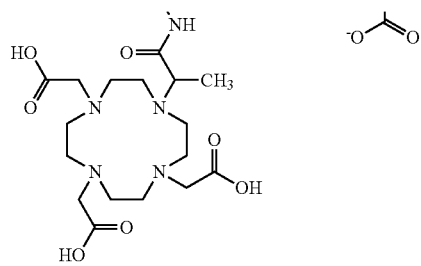
Gd$_2$-DO3A-derived chelate of formula (Gd$_2$-II-a),
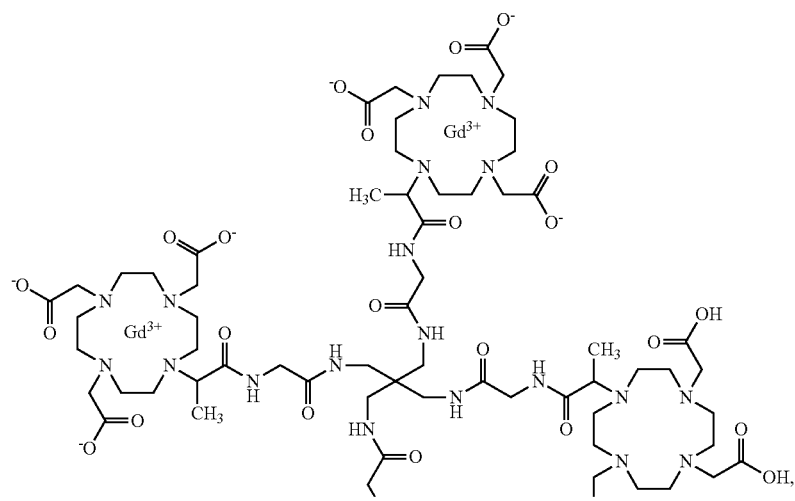
(Gd$_2$-II-a)
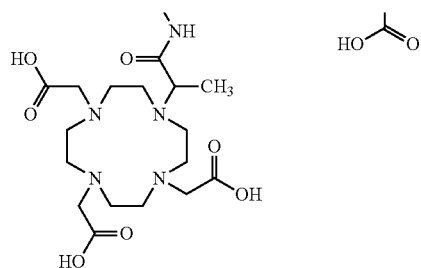

Gd-DO3A-derived chelate of formula (Gd-II-a),
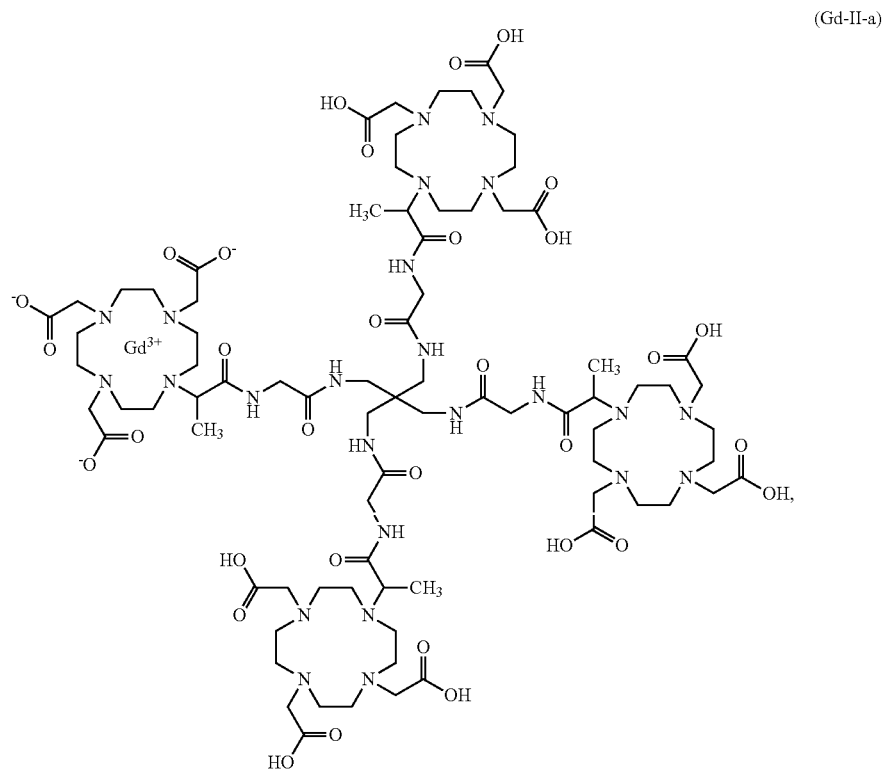
(Gd-II-a)
and DO3A-derived tetra-ligand of formula (II-a),
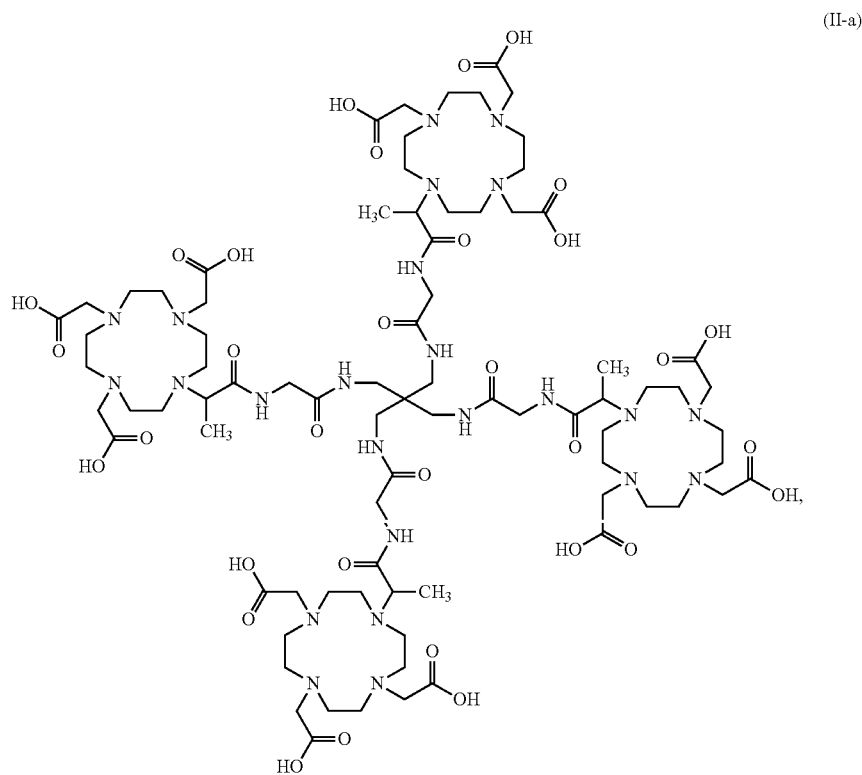
(II-a)

or a stereoisomer, a tautomer or a salt thereof, or a mixture of same, for the manufacture of contrast agents for magnetic resonance imaging.

In accordance with a second embodiment of the seventh aspect, the present disclosure covers the use of DO3A-derived tetra-chelates with sub-stoichiometric amounts of gadolinium ions ($Gd^{3+}$), which are selected from the group consisting of:

$Gd_2$-DO3A-derived chelate of formula ($Gd_2$-II-a),

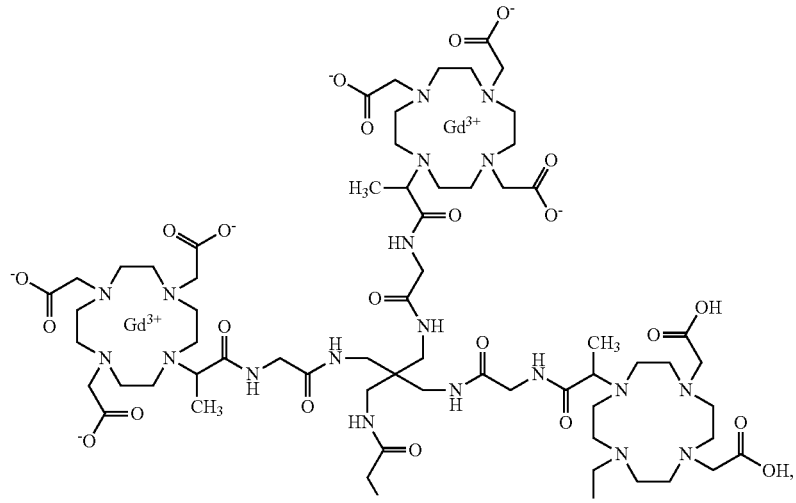

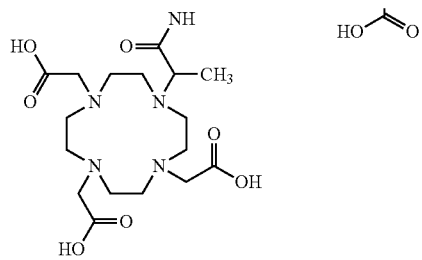

Gd-DO3A-derived chelate of formula (Gd-II-a),

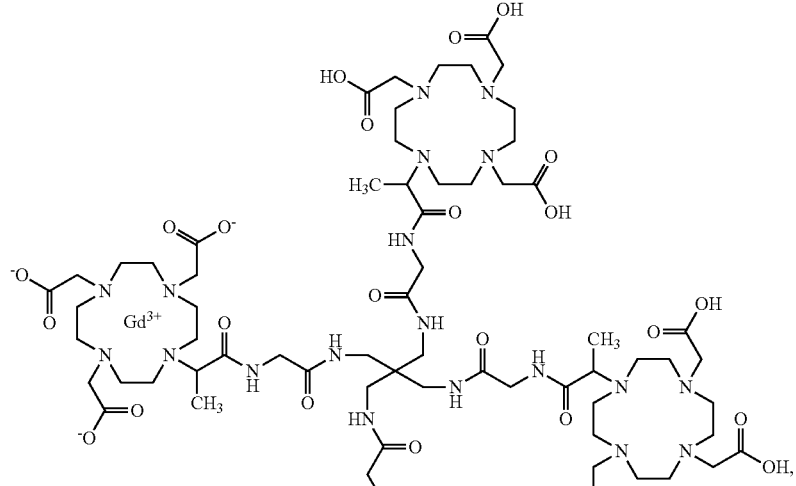

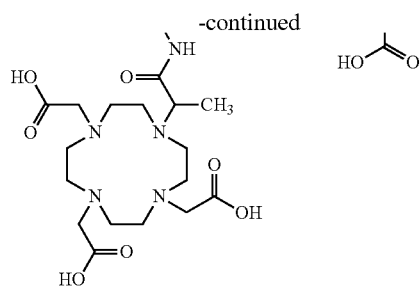

and DO3A-derived tetra-ligand of formula (II-a), (II-a)

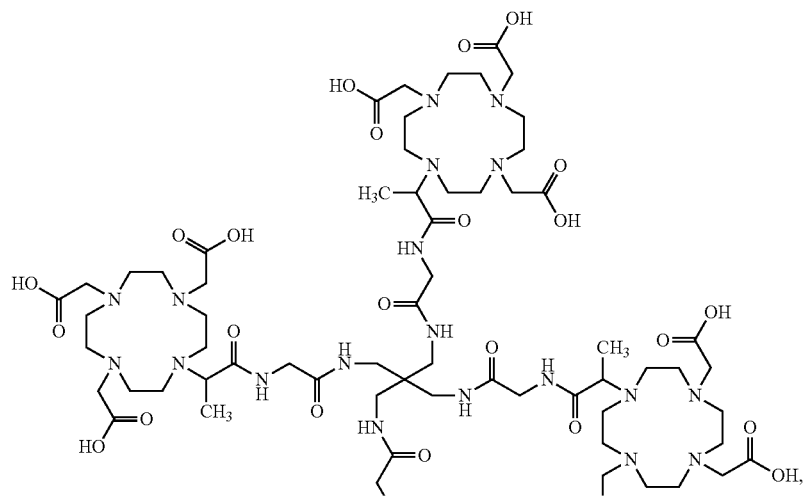

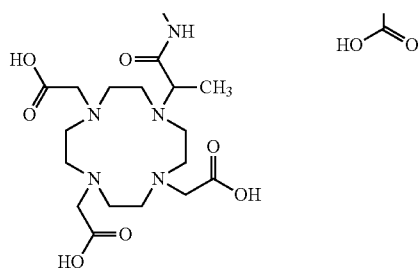

or a stereoisomer, a tautomer or a salt thereof, or a mixture of same, for the manufacture of contrast agents for magnetic resonance imaging.

In accordance with a variant of the seventh aspect, the present disclosure covers the use of DO3A-derived tetra-chelates with sub-stoichiometric amounts of gadolinium ions ($Gd^{3+}$), which are selected from the group consisting of:

Gd₃-DO3A-derived chelate of formula (Gd₃-II-b),
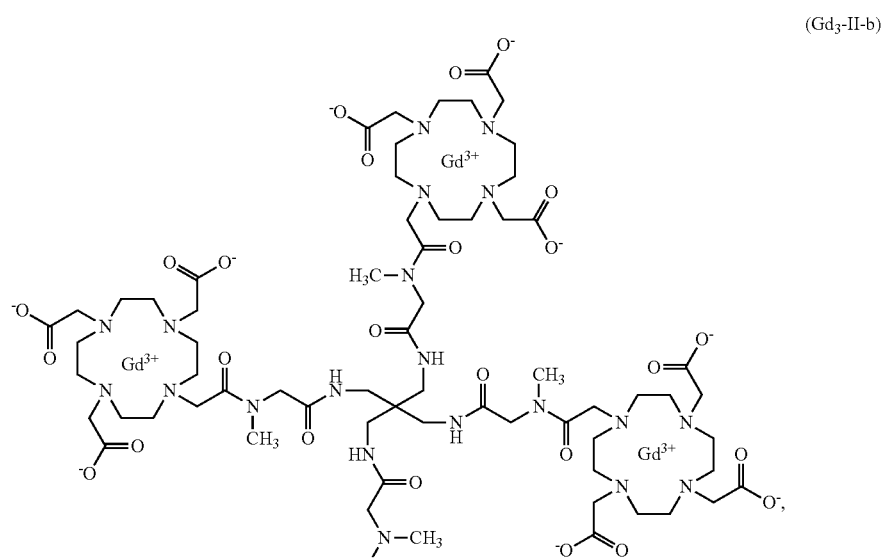
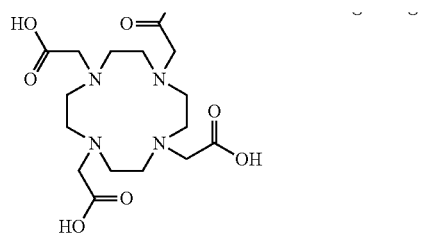
Gd₂-DO3A-derived chelate of formula (Gd₂-II-b), Gd-DO3A-derived chelate of formula (Gd-II-b),
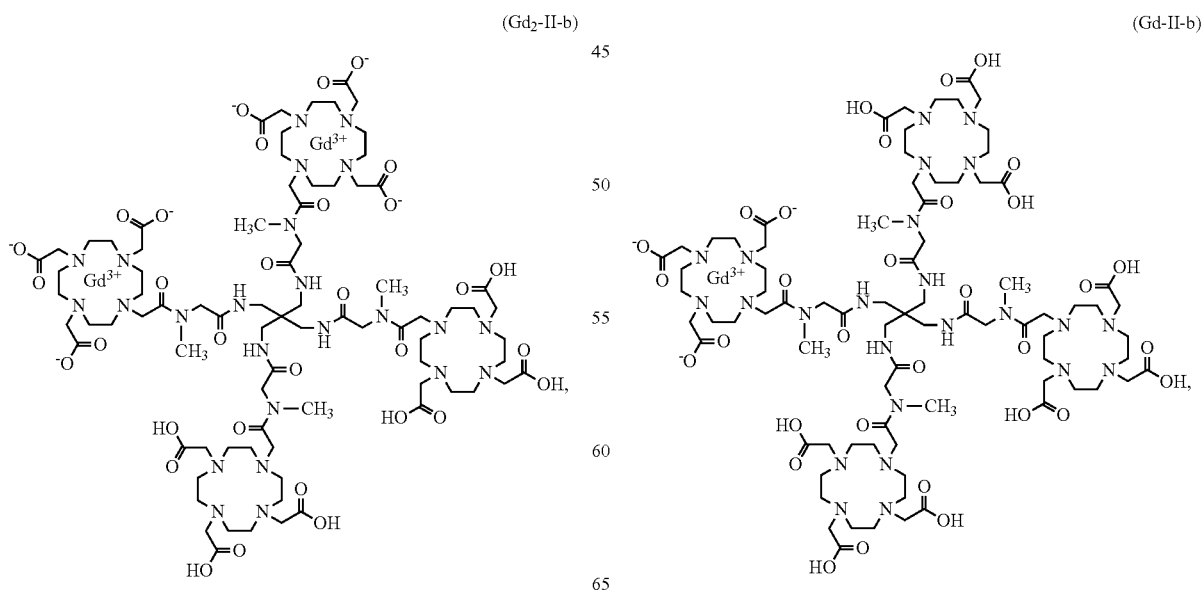

and

Gd DO3A-derived tetra-ligand of formula (II-b), (II-b)

Gd₂-DO3A-derived chelate of formula (Gd₂-II-c),

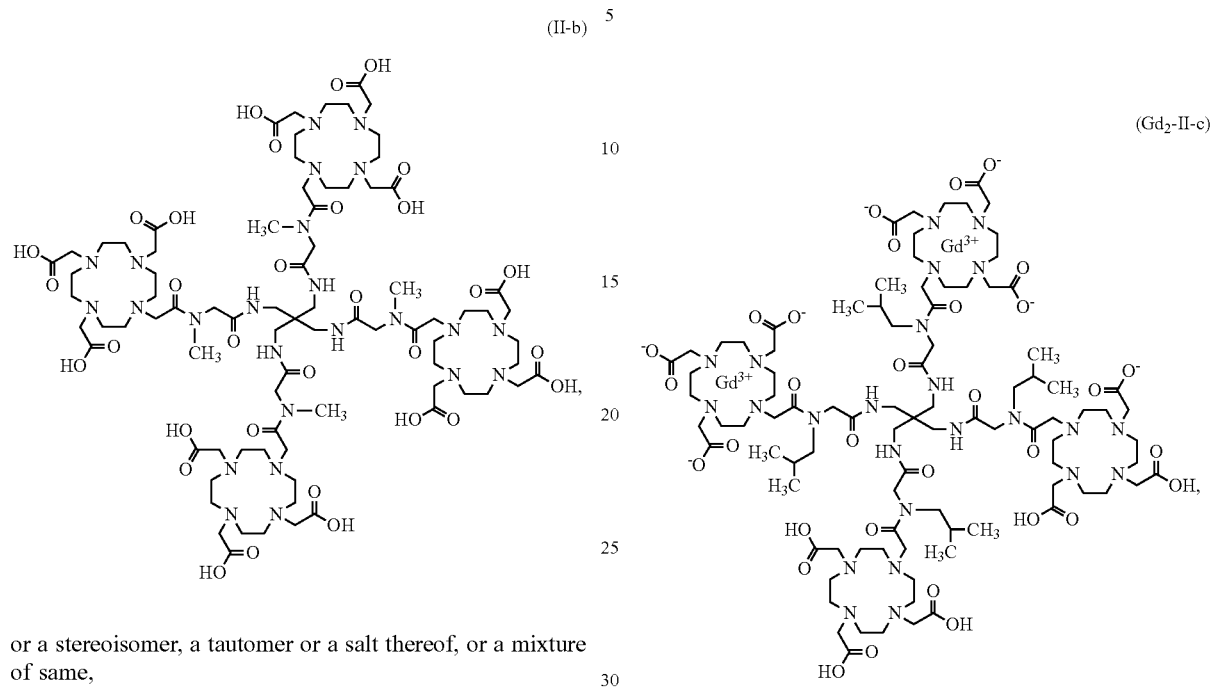

or a stereoisomer, a tautomer or a salt thereof, or a mixture of same, for the manufacture of contrast agents for magnetic resonance imaging.

In accordance with another variant of the seventh aspect, the present disclosure covers the use of DO3A-derived tetra-chelates with sub-stoichiometric amounts of gadolinium ions ($Gd^{3+}$), which are selected from the group consisting of:

Gd₃-DO3A-derived chelate of formula (Gd₃-II-c),

Gd-DO3A-derived chelate of formula (Gd-II-c),

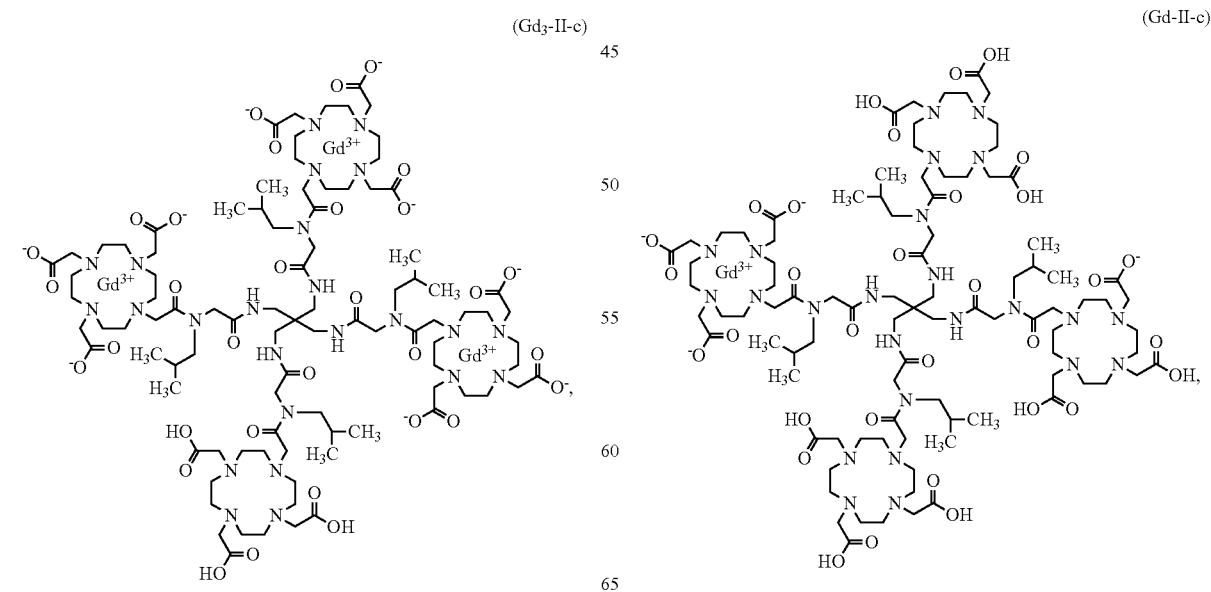

and
DO3A-derived tetra-ligand of formula (II-c),

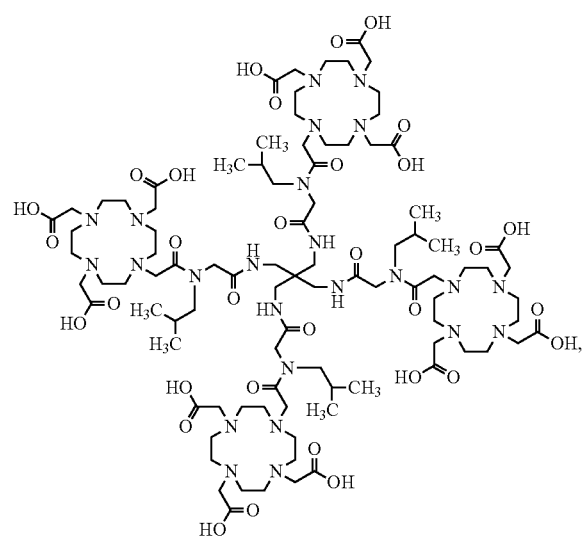

(II-c)

or a stereoisomer, a tautomer or a salt thereof, or a mixture of same,
for the manufacture of contrast agents for magnetic resonance imaging.

The various embodiments of the present disclosure will be illustrated by means of the non-limiting examples which follow.

EXPERIMENTAL SECTION

Example 1—Production of a Liquid Pharmaceutical Formulation Containing the $Gd_4$-DO3A-Derived Tetra-Chelate of Formula (I-a) and Ca-BT-DO3A (Calcobutrol)

The process for producing a liquid pharmaceutical formulation was carried out according to the following steps:
a) A manufacturing vessel was charged with 720.5 g water for injections and 1.217 g trometamol was dissolved while stirring. The pH of the solution obtained in step a) was adjusted to a pH of 7.6 to 8.2 by decreasing the pH by adding a 0.1 N solution of hydrochloric acid.
b) 0.147 g [i.e. 0.1% mol/mol related to the total Gd concentration] of Ca-BT-DO3A was added and dissolved while stirring.
c) 193.4 g (i.e. 0.075 M) of the $Gd_4$-DO3A-derived tetra-chelate of formula (I-a) was added to the solution obtained in step b) and dissolved while stirring.
d) 4.4 g of sodium chloride was added to the solution obtained in step c) and dissolved while stirring.
e) The pH of the solution obtained in step d) was adjusted to a pH of 7.2 to 7.6 by decreasing the pH by adding a 0.1 N solution of hydrochloric acid. The density of the solution was adjusted to a target value of 1.0998 g/mL by adding water. The solution was then filtered through a sterile filter with 0.2 μm pore size and placed in a container, which was subjected to sterilization at 121° C. for at least 15 minutes to yield the liquid pharmaceutical formulation.

By the procedure described above, the following formulation was obtained:

TABLE 2

Proportions in the formulation of $Gd_4$-DO3A-derived tetra-chelate of formula (I-a)

| Ingredients | Proportions in the formulation |
| --- | --- |
| $Gd_4$-DO3A-derived tetra-chelate of formula (I-a) | 193.4 g (0.3 mol Gd/L) |
| Ca-BT-DO3A | 0.147 g (0.3 mmol/L, i.e. 0.1% mol/mol vs Gd) |
| trometamol | 10 mmol/L |
| sodium chloride | 4.4 g |
| HCl | quantum satis, pH 7.4 ± 0.5 |
| water for injection | quantum satis 1 L |
| | (final volume of formulation = 1 L) |

The assaying of free gadolinium was carried out by colorimetry with Xylenol Orange. Xylenol Orange forms, with the free gadolinium, a colored complex having a specific absorbance (Barge et. al. Contrast Media & Molecular Imaging, 2006; 1; 184). Testing was conducted in comparison to a solution of gadolinium sulfate containing 2 ppm (m/v) of gadolinium. The final formulation contained less than or equal to 2 ppm (m/v) free gadolinium.

Example 2—Stability and Osmolality

Stability studies and measurements of osmolality were carried out with the formulation obtained as described in example 1.

Measurements, over the course of time, of the concentration of the $Gd_4$-DO3A-derived tetra-chelate of formula (I-a), free gadolinium and osmolality were carried out.

TABLE 3

Stability and Osmolality

| | Storage duration [months] | 2-8° C./ — | 25° C./ 60% RH | 30° C./ 75% RH | 40° C./ 75% RH |
|---|---|---|---|---|---|
| concentration of Gd4-DO3A-derived tetra-chelate of formula (I-a) [g/L] | Initial | 187.7 | 187.7 | 187.7 | 187.7 |
| | 1 | Not tested | Not tested | Not tested | 187.7 |
| | 3 | Not tested | Not tested | Not tested | 193.0 |
| | 6 | 193.2 | 194.5 | Not tested | 194.9 |
| | 9 | Not tested | Not tested | 192.1 | Not tested |
| | 12 | Not tested | Not tested | 194.2 | Not tested |
| | 18 | Not tested | Not tested | 192.7 | Not tested |
| amount of free gadolinium [ppm (m/v)] | Initial | <2 | <2 | <2 | <2 |
| | 1 | Not tested | Not tested | Not tested | <2 |
| | 3 | Not tested | Not tested | Not tested | <2 |
| | 6 | <2 | <2 | Not tested | <2 |
| | 9 | Not tested | Not tested | <2 | Not tested |
| | 12 | Not tested | Not tested | <2 | Not tested |
| | 18 | Not tested | Not tested | <2 | Not tested |
| osmolality of $Gd_4$-DO3A-derived tetra-chelate of formula (I-a) [mOsm/kg] | Initial | 294 | 294 | 294 | 294 |
| | 1 | Not tested | Not tested | Not tested | 288 |
| | 3 | Not tested | Not tested | Not tested | 283 |
| | 6 | 283 | 284 | Not tested | 283 |
| | 9 | Not tested | Not tested | 282 | Not tested |
| | 12 | Not tested | 296 | 306 | Not tested |
| | 18 | Not tested | Not tested | 280 | Not tested |

Quantification of the $Gd_4$-DO3A-derived tetra-chelate of formula (I-a) was conducted by HPLC-UV against external standard solutions. Osmolality was determined using an automated vapor pressure osmometer.

The assaying of free gadolinium was carried out by colorimetry with Xylenol Orange. Xylenol Orange forms, with the free gadolinium, a colored complex having a specific absorbance (Barge et. al. Contrast Media & Molecular Imaging, 2006; 1; 184). Testing was conducted in comparison to a solution of gadolinium sulfate containing 2 ppm (m/v) of gadolinium.

The amount of $Gd_4$-DO3A-derived tetra-chelate of formula (I-a) remained stable after six months at 25° C. (long term stability) and also after six months at 40° C. (accelerated storage conditions). Free gadolinium was lower than or equal to 2 ppm (m/v) in the formulation. The formulation was isotonic with blood plasma.

Example 3—Viscosity

Viscosity measurements were carried out with the formulation obtained as described in example 1, at 20'C and 37° C.

TABLE 4

Viscosity

| Product | Viscosity 20° C. [mPas] | Viscosity 37° C. [mPas] |
|---|---|---|
| Formulation containing the $Gd_4$-DO3A-derived tetra-chelate of formula (I-a), as described in example 1 | 1.87 | 1.22 |

TABLE 4-continued

Viscosity

| Product | Viscosity 20° C. [mPas] | Viscosity 37° C. [mPas] |
|---|---|---|
| 0.9% (m/v) sodium chloride | 1.03 | 0.74 |
| Gadovist ® 1.0 | 8.86* | 4.96* |

*Fachinformation des Arzneimittel-Kompendium der Schweiz ®

Viscosities were determined using a microfluidic viscosimeter (m-VROC, RheoSense). The viscosities were only slightly higher than for isotonic sodium chloride solution but significantly lower than Gadovist® 1.0 and can be considered low.

Example 4—Synthesis of DO3A-Derived Tetra-Ligand of Formula (II-a), Gd-DO3A-Derived Chelate (Gd-II-a), $Gd_2$-DO3A-Derived Chelate ($Gd_2$-II-a)

[4,10-bis(carboxylatomethyl)-7-{3,6,12,15-tetraoxo-16-[4,7,10-tris-(carboxylatomethyl)-1,4,7,10-tetraazacyclododecan-1-yl]-9,9-bis({[({2-[4,7,10-tris-(carboxylatomethyl)-1,4,7,10-tetraazacyclododecan-1-yl]propanoyl}amino)acetyl]amino}methyl)-4,7,11,14-tetraazaheptadecan-2-yl}-1,4,7,10-tetraazacyclododecan-1-yl]acetic acid (II-a)

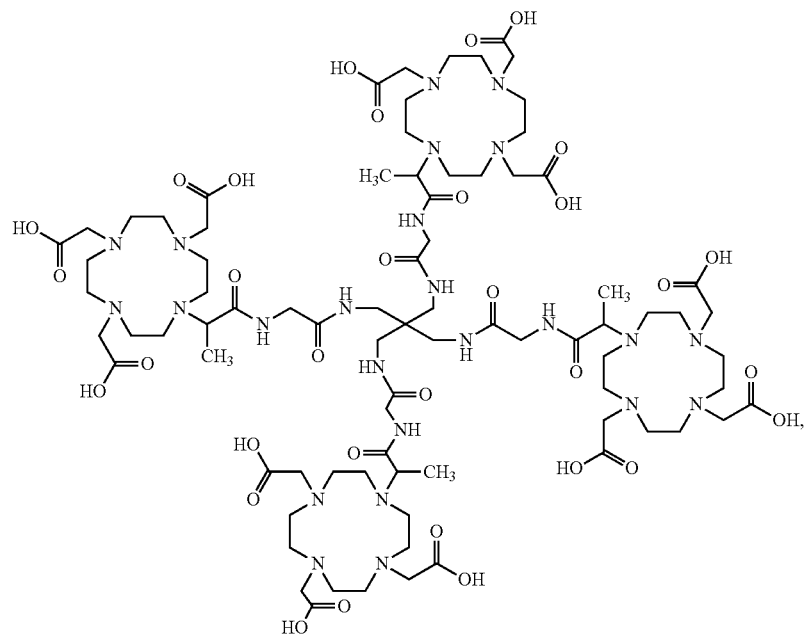
(II-a)
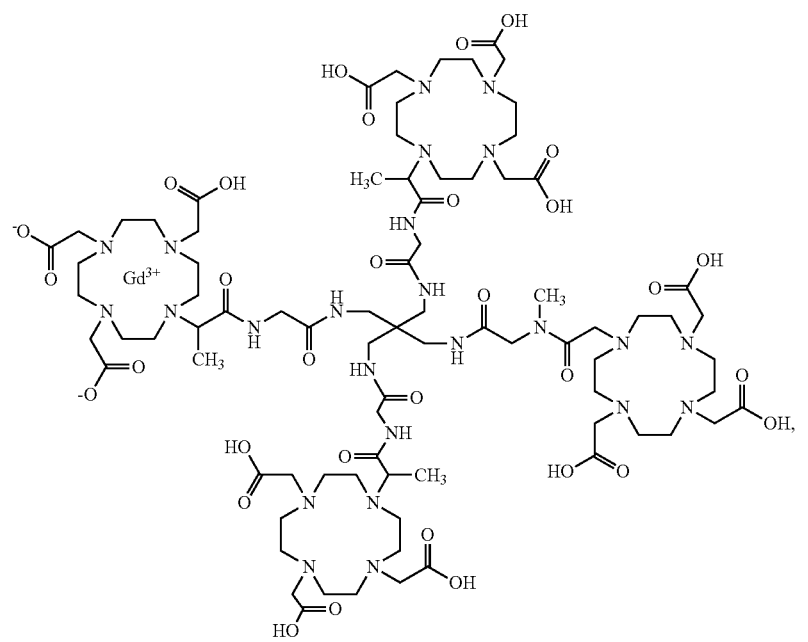
(Gd-II-a)

-continued (Gd₂-II-a)

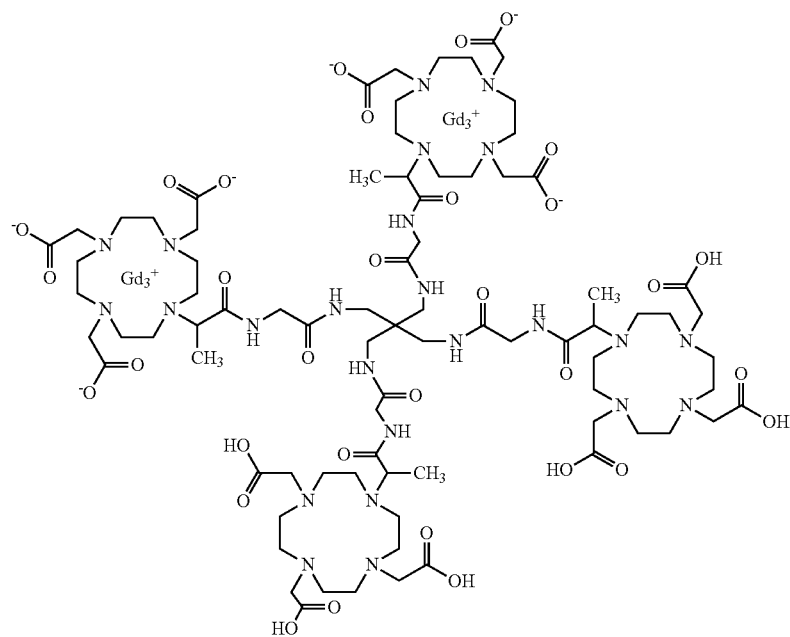

A solution of Gd₄-DO3A-derived tetra-chelate of formula (I-a), tetragadolinium [4,10-bis(carboxylatomethyl)-7-{3,6,12,15-tetraoxo-16-[4,7,10-tris(carboxylatomethyl)-1,4,7,10-tetra-azacyclododecan-1-yl]-9,9-bis({[({2-[4,7,10-tris(carboxylatomethyl)-1,4,7,10-tetraazacyclo-dodecan-1-yl]propanoyl}amino)acetyl]amino}methyl)-4,7,11,14-tetraazaheptadecan-2-yl}-1,4,7,10-tetraazacyclododecan-1-yl]acetate (WO 2016193190, Example 3; 1.00 eq., 5.60 g, 2.12 mmol) in water (470 mL) was treated with oxalic acid dihydrate (16.0 eq., 4.29 g, 34.0 mmol) and stirred at 100° C. for 6 hours. The cooled reaction mixture was filtrated (Microfilter PTFE 1.2 μm) and lyophilized. The obtained crude material was dissolved in water (200 mL) and the pH adjusted to 4.5 by addition of aqueous sodium hydroxide solution (2 M). The obtained solution was ultrafiltrated with water (18×100 mL) using an 1 kDa membrane and the final retentate was lyophilized yielding 2.98 g solid white powder which was analyzed using ¹H-NMR and HPLC.

¹H-NMR:

(400 MHz, D₂O): δ [ppm]: 1.18-1.20 (m, 12H), 2.60-2.75 (m, 7H), 2.87-3.54 (m, 85H), 3.67-3.95 (m, 31H), 4.03 (q, 5H).

HPLC:

Instrument: Agilent 1290 HPLC-ESI-MS G6130; column: Hypercarb (Thermo) 5 μm, 100×4.6 mm; Eluent A: water+ 0.1% formic acid, eluent B: acetonitrile+0.1% formic acid; gradient: 0-7 min 0-50% B, 7-8 min 100% B; flow rate 1 mL/min; temperature: 60° C.; injection: 20 μL; DAD scan: 200-300 nm; ESI-MS.

TABLE 5

| | HPLC | | | | | |
|---|---|---|---|---|---|---|
| Compound | Retention Time [min] | Relative amount [% peak area] | Amount component [g] | Amount Gd-free DO3A moieties [mmol] | Molecular weight [g/mol] | MS (ES⁺ and ES⁻) |
| II-a | 4.0 | 0.596 | 1.77 | 5.41 | 1961 | m/z (z = 2) = +982 (M + 2H)²⁺; m/z (z = 3) = +655 (M + 3H)³⁺ |
| Gd-II-a | 4.6 | 0.313 | 0.93 | 1.32 | 2116 | m/z (z = 3) = +706 (M + 3H)³⁺; m/z (z = −2) = −1057 (M − 2H)²⁻ |
| Gd₂-II-a | 5.5 | 0.091 | 0.27 | 0.32 | 2271 | m/z (z = 3) = +758 (M + 3H)³⁺; m/z (z = −2) = −1134 (M − 2H)²⁻ |
| total | — | 1.00 | 2.98 | 6.96 | — | — |

The MS revealed that the preparation contained the title compound (II-a) along with Gd-DO3A-derived chelate of formula (Gd-II-a) and Gd$_2$-DO3A-derived chelate of formula (Gd$_2$-II-a) in a ratio of (II-a):(Gd-II-a):(Gd$_2$-II-a)= 59.6:31.3:9.1, based on the relative peak area at 200 nm.

The amount of each component was calculated from the % peak area (% PA) and the total weight (w) of the compound: % PA*w.

The total molar amount of Gd free DO3A moieties in the compound was calculated for each component based on their number of Gd ions per tetramer (nGd), their amount (a) and molecular weight (mw): (4−nGd)*a/mw.

Example 5—Preparation of a Formulation for Injection of DO3A-Derived Tetra-Chelate of Formula (I-a) with a Defined Excess of Free DO3A Moieties (Present in Sub-Stoichiometric Chelates), Using the Mixture of Compounds of Example 4

29.8 g of Gd$_4$-DO3A-derived tetra-chelate of formula (I-a), water content 4.5% w/w, were dissolved in 115 mL of 10 mM Tris-HCl buffer, pH 7.4 in water for injection. The pH of the solution was adjusted to 7.4 using dilute aqueous sodium hydroxide and hydrochloric acid. The concentration was measured with ICP-OES: 334 mmol Gd/L. The volume of the solution was determined by weighing and under consideration of the density of the solution (1.10 g/mL): 132 mL. The solution contains 44.1 mmol Gd.

0.018 g of the mixture of compounds described in Example 4, equivalent to 0.044 mmol of free DO3A moieties, was added (0.018 g*6.96 mmol/2.98 g=0.044 mmol). The volume was adjusted to 176 mL with Tris-HCL buffer, pH 7.4.

The osmolality of the formulation was measured and an appropriate amount of sodium chloride was added to obtain 312 mOsm/kg which is isotonic to human blood.

Finally the solution was filtered through 0.22 μm in glass bottles which were sealed and steam autoclaved. A final measurement of the Gd-concentration confirmed 252 mmol Gd/L.

As a result an isotonic injection with 252 mmol Gd/L and an excess of 0.1 mol % of free ligand based on the total concentration of Gd and on free DO3A moieties was prepared (0.044 mmol/44.1 mmol=0.1 mol %).

The viscosity of the injection, as determined with a rolling ball viscometer (Paar) at 37° C., was 1.2 mPas.

The invention claimed is:

1. A liquid pharmaceutical formulation comprising a DO3A -derived tetra-chelate of general formula (I):

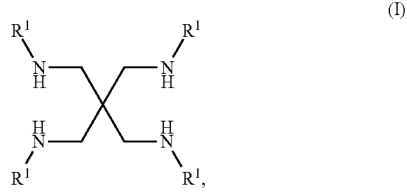

(I)

wherein
$R^1$ represents a group selected from:

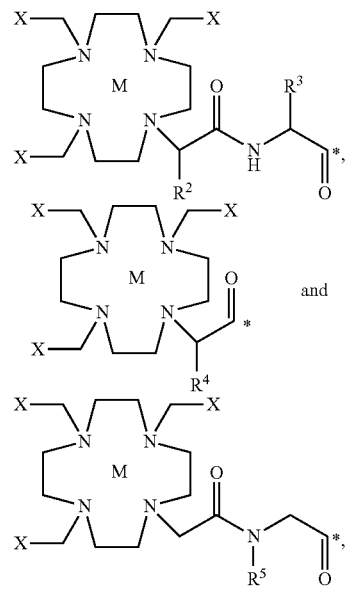

wherein group * indicates the point of attachment of the group with the rest of the molecule, $R^2$, $R^3$, and $R^4$ independently of each other represents a hydrogen atom or a group selected from: $C_1$-$C_6$-alkyl, $C_3$-$C_6$-cycloalkyl, ($C_1$-$C_2$-alkoxy)-($C_2$-$C_3$-alkyl)-, and phenyl, wherein the $C_1$-$C_6$-alkyl group is optionally substituted, identically or differently, with a phenyl substituent, wherein the phenyl substituent is optionally substituted, one, two or three times, identically or differently, with a group selected from a halogen atom, $C_1$-$C_3$-alkyl, $C_1$-$C_3$-haloalkyl, and $C_1$-$C_3$-alkoxy, and wherein the phenyl group is optionally substituted, one, two or three times, identically or differently, with a group selected from a halogen atom, $C_1$-$C_3$-alkyl, $C_1$-$C_3$-haloalkyl, and $C_1$-$C_3$-alkoxy, $R^5$ represents a group selected from:

$C_1$-$C_6$-alkyl, $C_3$-$C_6$-cycloalkyl, ($C_1$-$C_2$-alkoxy)-($C_2$-$C_3$-alkyl)- and phenyl, wherein the $C_1$-$C_6$-alkyl group is optionally substituted, identically or differently, with a phenyl substituent, wherein the phenyl substituent is optionally substituted, one, two or three times, identically or differently, with a group selected from a halogen atom, $C_1$-$C_3$-alkyl, $C_1$-$C_3$-haloalkyl, and $C_1$-$C_3$-alkoxy, and wherein the phenyl group is optionally substituted, one, two, or three times, identically or differently, with a group selected from a halogen atom, $C_1$-$C_3$-alkyl, $C_1$-$C_3$-haloalkyl, and $C_1$-$C_3$-alkoxy, X represents a group C(=O)OH or C(=O)O−, and M represents $Gd^{3+}$, or a stereoisomer, a tautomer or a salt thereof, or a mixture of same, wherein the formulation further comprises a pharmaceutically acceptable solvent; and at least one compound capable of forming a chelate with a free paramagnetic metal ion M, wherein the at least one compound is Ca-BT-DO3A (Calcobutrol) in a concentration range of 0.002% to 5% mol/mol (inclusive), measured as a proportion relative to a total concentration of the $Gd^{3-}$ ion in the formulation, wherein the DO3A-derived tetra-chelate has a concentration in the formulation in a range of 60 to 750 mmol paramagnetic $Gd^{3-}$/L (inclusive).

2. The formulation according to claim 1, wherein $R^2$ represents a hydrogen atom or a methyl group, $R^3$ and $R^4$ each represent a hydrogen atom, and $R^5$ represents a group selected from methyl, ethyl, isopropyl, 2-methylpropyl, benzyl, cyclopropyl, cyclopentyl, cyclohexyl, 2-methoxyethyl, 2-ethoxyethyl, and phenyl.

3. The formulation according to claim 1, wherein the DO3A-derived tetra-chelate of formula (I) has a structure selected from a chelate of formulae (I-a), (I-b), and (I-c):

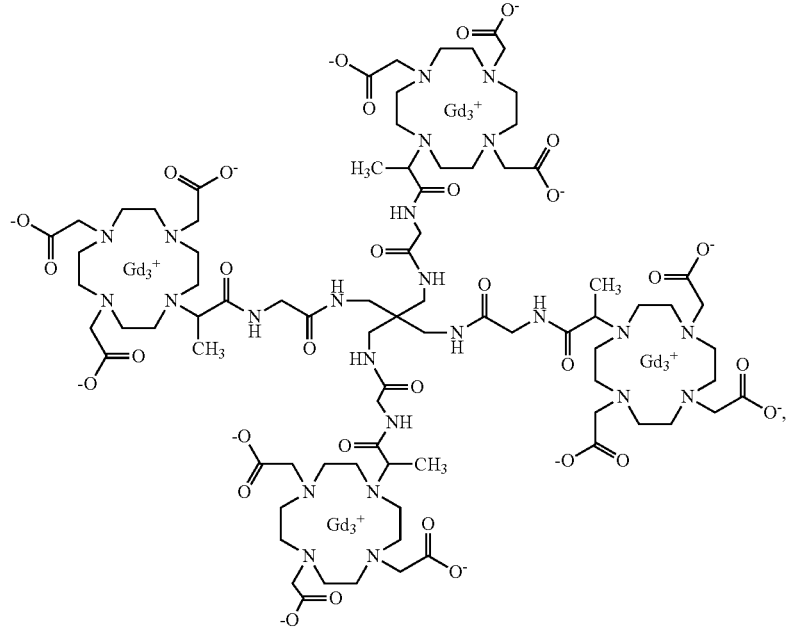

(I-a)

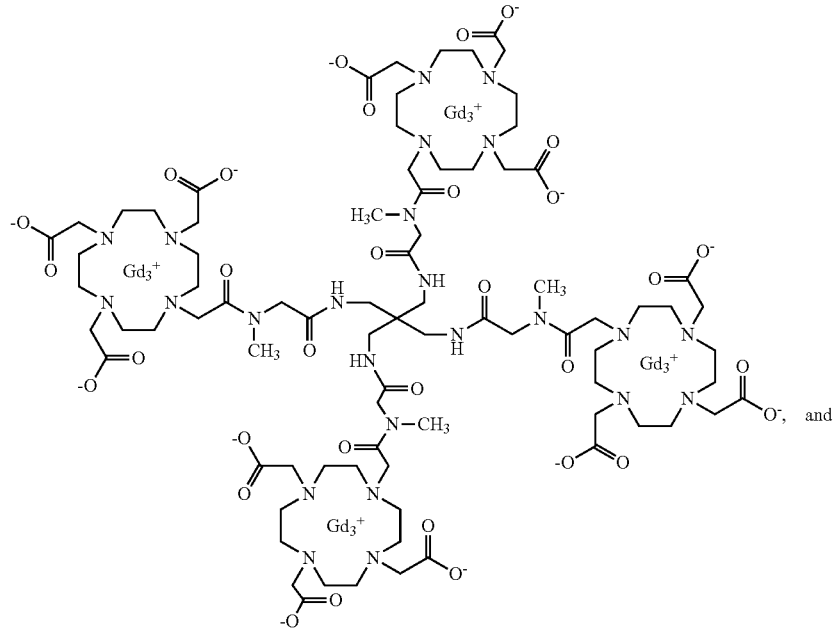

(I-b)

and

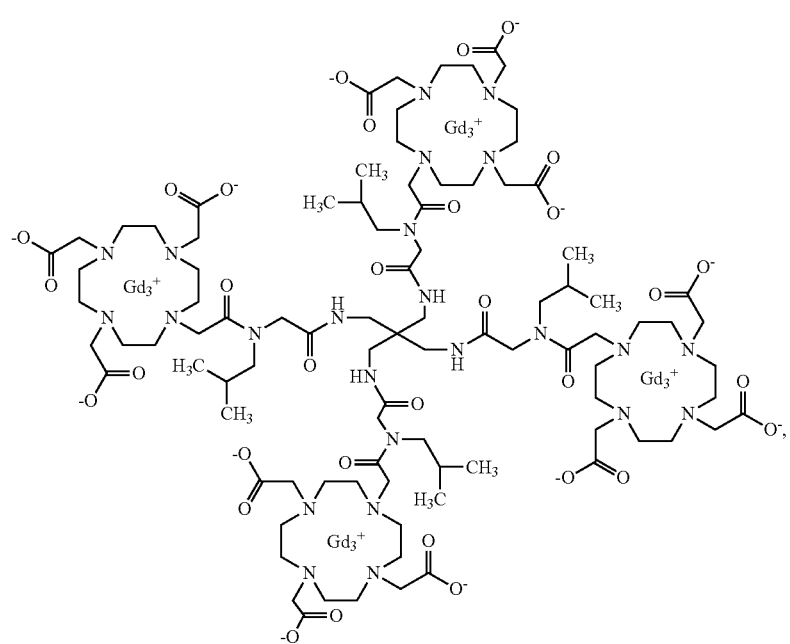

(I-c)

or a stereoisomer, a tautomer or a salt thereof, or a mixture of same.

4. The formulation according to claim 3, wherein the DO3A-derived tetra-chelate of formula (I) has the formula (I-a):

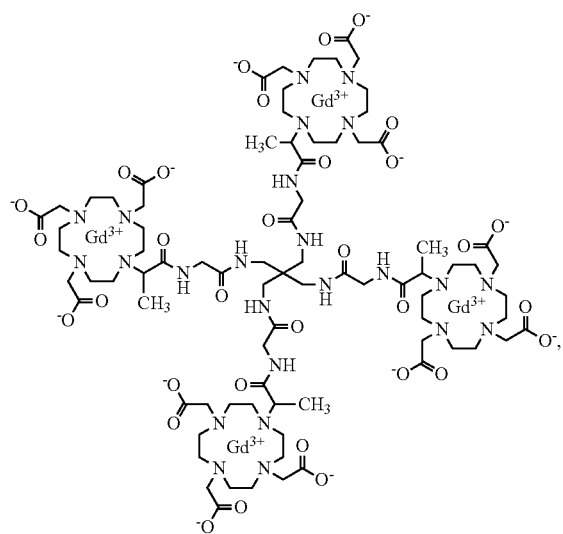

(I-a)

or a stereoisomer, a tautomer or a salt thereof, or a mixture of same.

5. The formulation according to claim 4, wherein the DO3A-derived tetra-chelate of formula (I-a) has a stereochemistry at the chiral carbon of the four methyl substituents selected from the group consisting of RRRR, SSSS, RSSS, RRSS, and RRRS stereoisomers, and racemic and diastereomeric mixtures of any thereof.

6. The formulation according to claim 1, wherein the formulation has a concentration of a free paramagnetic $Gd^{3+}$ of less than or equal to 5 ppm (m/v).

7. The formulation according to claim 1, wherein the formulation has a pH in a range of 4.5 to 8.5 (inclusive).

8. The formulation according to claim 1, further comprising a buffer, wherein the buffer is selected from the group consisting of a citrate buffer, a lactate buffer, an acetate buffer, a tartrate buffer, a malate buffer, a maleate buffer, a phosphate buffer, a succinate buffer, an ascorbate buffer, a carbonate buffer, a trometamol (TRIS, 2-amino-2-(hydroxymethyl)propane-1,3-diol) buffer, an HEPES (2-[4-(2-hydroxyethyl)-1-piperazine] ethanesulfonic acid) buffer, an MES (2-morpholinoethanesulfonic acid) buffer, and mixtures thereof.

9. A process for preparing a liquid pharmaceutical formulation, the process comprising the following steps:

providing a pharmaceutically acceptable solvent;

dissolving a DO3A-derived tetra-chelate of formula (I):

(I)

$$\begin{array}{c} R^1 \\ | \\ HN-CH_2-C-CH_2-NH \\ | \\ CH_2 \quad CH_2 \\ | \quad \quad | \\ HN \quad \quad NH \\ | \quad \quad | \\ R^1 \quad \quad R^1 \end{array}$$

wherein
R¹ represents a group selected from:

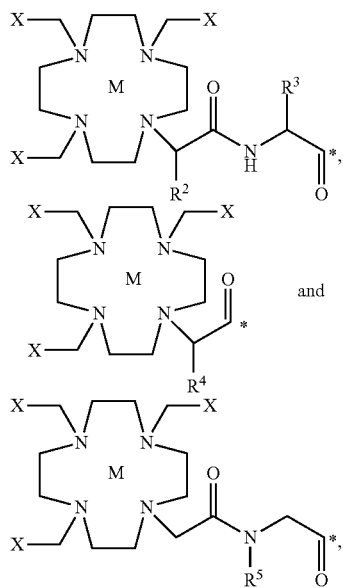

wherein group * indicates the point of attachment of the group with the rest of the molecule, R², R³, and R⁴ independently of each other represents a hydrogen atom or a group selected from: $C_1$-$C_6$-alkyl, $C_3$-$C_6$-cycloalkyl, ($C_1$-$C_2$-alkoxy)-($C_2$-$C_3$-alkyl)-, and phenyl, wherein the $C_1$-$C_6$-alkyl group is optionally substituted, identically or differently, with a phenyl substituent, wherein the phenyl substituent is optionally substituted, one, two or three times, identically or differently, with a group selected from a halogen atom, $C_1$-$C_3$-alkyl, $C_1$-$C_3$-haloalkyl, and $C_1$-$C_3$-alkoxy, and wherein the phenyl group is optionally substituted, one, two or three times, identically or differently, with a group selected from a halogen atom, $C_1$-$C_3$-alkyl, $C_1$-$C_3$-haloalkyl, and $C_1$-$C_3$-alkoxy, R⁵ represents a group selected from:
$C_1$-$C_6$-alkyl, $C_3$-$C_6$-cycloalkyl, ($C_1$-$C_2$-alkoxy)-($C_2$-$C_3$-alkyl)- and phenyl, wherein the $C_1$-$C_6$-alkyl group is optionally substituted, identically or differently, with a phenyl substituent, wherein the phenyl substituent is optionally substituted, one, two or three times, identically or differently, with a group selected from a halogen atom, $C_1$-$C_3$-alkyl, $C_1$-$C_3$-haloalkyl, and $C_1$-$C_3$-alkoxy, and wherein the phenyl group is optionally substituted, one, two, or three times, identically or differently, with a group selected from a halogen atom, $C_1$-$C_3$-alkyl, $C_1$-$C_3$-haloalkyl, and $C_1$-$C_3$-alkoxy, X represents a group C(=O)OH or C(=O) O³¹, and
M represents $Gd^{3+}$;

or a stereoisomer, a tautomer or a salt thereof, or a mixture of same, in the pharmaceutically acceptable solvent in in sufficient amount to produce a solution of the formulation having a concentration of DO3A-derived tetra-chelate of formula (I) in a range of 60 to 750 mmol paramagnetic $Gd^{3-}$ ion/L (inclusive), and dissolving at least one compound capable of forming a chelate with $Gd^{3+}$ in sufficient amount to produce a solution having a concentration in a range of 0.002% to 5% mol/mol (inclusive) with reference to the total concentration of the $Gd^{3+}$ ion, wherein the compound capable of forming a chelate with $Gd^3+$ is Ca-BT-DO3A (Calcobutrol).

10. The process according to claim 9, further comprising one or more additional steps selected from the group consisting of:

dissolving a buffer in the pharmaceutically acceptable solvent or the solution, thereby obtaining a buffered solution and adjusting the pH of the buffered solution to a pH in a range of 7.6 to 8.2 (inclusive);

dissolving the Ca-BT-DO3A (Calcobutrol) in the solution;

dissolving an isotonicity agent in the solution;

adjusting the pH of the solution to a pH in a range of 4.5 to 8.5 (inclusive);

adjusting the concentration of the DO3A-derived tetra-chelate of the formula (I) by addition of an additional amount of the pharmaceutically acceptable solvent; and sterilizing the solution.

11. A process for preparing a liquid pharmaceutical formulation, the process comprising the following steps:
providing a pharmaceutically acceptable solvent;
dissolving Ca-BT-DO3A (Calcobutrol) in the pharmaceutically acceptable solvent; and
dissolving a DO3A-derived tetra-chelate of formula (I):

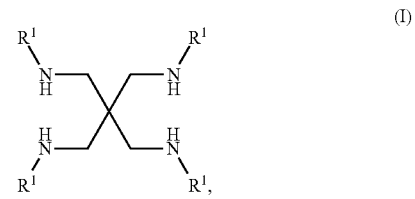

(I)

wherein
R¹ represents a group selected from:

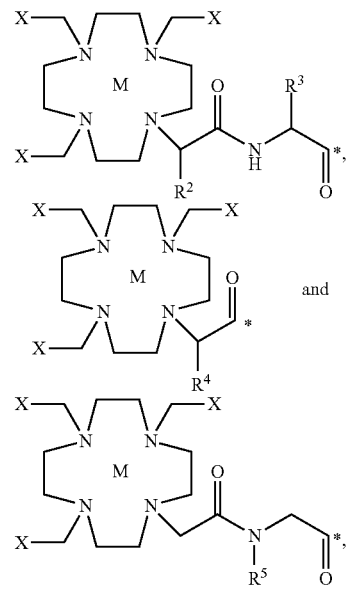

wherein group * indicates the point of attachment of the group with the rest of the molecule, $R^2$, $R^3$, and $R^4$ independently of each other represents a hydrogen atom or a group selected from: $C_1$-$C_6$-alkyl, $C_3$-$C_6$-cycloalkyl, ($C_1$-$C_2$-alkoxy)-($C_2$-$C_3$-alkyl)-, and phenyl, wherein the $C_1$-$C_6$-alkyl group is optionally substituted, identically or differently, with a phenyl substituent, wherein the phenyl substituent is optionally substituted, one, two or three times, identically or differently, with a group selected from a halogen atom, $C_1$-$C_3$-alkyl, $C_1$-$C_3$-haloalkyl, and $C_1$-$C_3$-alkoxy, and wherein the phenyl group is optionally substituted, one, two or three times, identically or differently, with a group selected from a halogen atom, $C_1$-$C_3$-alkyl, $C_1$-$C_3$-haloalkyl, and $C_1$-$C_3$-alkoxy, $R^5$ represents a group selected from:

$C_1$-$C_6$-alkyl, $C_3$-$C_6$-cycloalkyl, ($C_1$-$C_2$-alkoxy)-($C_2$-$C_3$-alkyl)- and phenyl, wherein the $C_1$-$C_6$-alkyl group is optionally substituted, identically or differently, with a phenyl substituent, wherein the phenyl substituent is optionally substituted, one, two or three times, identically or differently, with a group selected from a halogen atom, $C_1$-$C_3$-alkyl, $C_1$-$C_3$-haloalkyl, and $C_1$-$C_3$-alkoxy, and wherein the phenyl group is optionally substituted, one, two, or three times, identically or differently, with a group selected from a halogen atom, $C_1$-$C_3$-alkyl, $C_1$-$C_3$-haloalkyl, and $C_1$-$C_3$-alkoxy, X represents a group C(=O)OH or C(=O)O⁻, and M represents $Gd^{3+}$;

or a stereoisomer, a tautomer or a salt thereof, or a mixture of same, in the pharmaceutically acceptable solvent in sufficient amount to produce a final solution having a formulation having a concentration of the DO3A-derived tetra-chelate of formula (I) in a range of 1 to 1000 mmol $Gd^{3+}$/L (inclusive), and wherein the Ca-BT-DO3A is dissolved in the pharmaceutically acceptable solvent in sufficient amount to produce a solution having a concentration in a range of 0.002% to 5% mol/mol (inclusive) with reference to the total concentration of the $Gd^{3+}$ ion.

12. The process according to claim 11, further comprising:

dissolving an amount of the Ca-BT-DO3A (Calcobutrol) in the range of 0.002% to 5% mol/mol (inclusive) with reference to the total concentration of the $Gd^{3+}$ in the formulation in the pharmaceutically acceptable solvent to form a first solution; and dissolving the DO3A-derived tetra-chelate of formula (I) in the first solution in sufficient amount to produce a final solution having a liquid pharmaceutical formulation having a concentration of the DO3A-derived tetra-chelate of formula (I) in a range of 1 mmol paramagnetic metal ion/L to 1000 mmol $Gd^{3+}$/L (inclusive).

13. The process according to claim 11, wherein the DO3A-derived tetra-chelate of formula (I) is a $Gd_4$-DO3A-derived tetra-chelate having a formula (I-a):

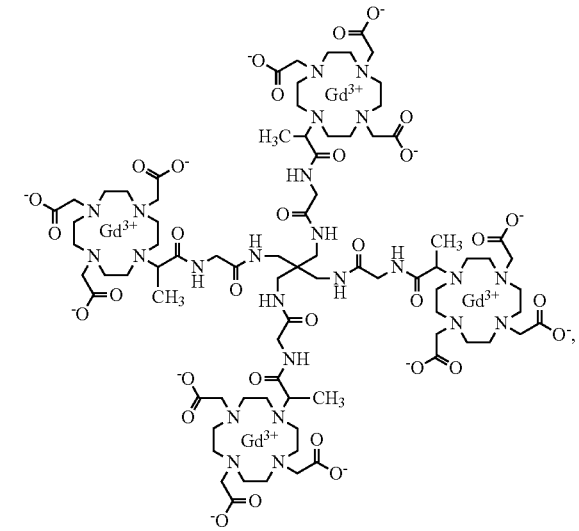

(I-a)

or a stereoisomer, a tautomer or a salt thereof, or a mixture of same, wherein the $Gd_4$-DO3A-derived tetra-chelate of formula (I-a) is dissolved in sufficient amount to produce a liquid pharmaceutical formulation having a concentration of the $Gd_4$-DO3A-derived tetra-chelate of formula (I-a) in the range of 1 mmol $Gd^{3+}$/L to 1000 mmol $Gd^{3+}$/L (inclusive).

14. The process according to claim 12, wherein dissolving an amount of the CaBT-DO3A (Calcobutrol) comprises:

dissolving an amount of the Ca-BT-DO3A in the range of 0.002% to 5% mol/mol (inclusive) with reference to the total concentration of the $Gd^{3+}$ ion in the formulation in the pharmaceutically acceptable solvent or an aqueous buffer solution to provide a first solution.

* * * * *

UNITED STATES PATENT AND TRADEMARK OFFICE
CERTIFICATE OF CORRECTION

PATENT NO. : 11,944,690 B2
APPLICATION NO. : 17/295647
DATED : April 2, 2024
INVENTOR(S) : Holzschuh et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 180 days.

Signed and Sealed this
Eighth Day of October, 2024

Katherine Kelly Vidal
*Director of the United States Patent and Trademark Office*